United States Patent
Kanthasamy et al.

(10) Patent No.: US 11,576,883 B2
(45) Date of Patent: Feb. 14, 2023

(54) L-DOPA MICROBIOME THERAPY

(71) Applicants: Iowa State University Research Foundation, Inc., Ames, IA (US); Board of Regents, The University of Texas System, Austin, TX (US)

(72) Inventors: Anumantha G. Kanthasamy, Ames, IA (US); Ahmed Abdalla, Ames, IA (US); Gregory Phillips, Ames, IA (US); Nicholas Backes, Ames, IA (US); Andrew D. Ellington, Austin, TX (US); Ross Thyer, Houston, TX (US)

(73) Assignees: Iowa State University Research Foundation, Inc., Ames, IA (US); Board of Regents, The University of Texas System, Austin, TX (US)

( * ) Notice: Subject to any disclaimer, the term of this patent is extended or adjusted under 35 U.S.C. 154(b) by 324 days.

(21) Appl. No.: 16/287,437

(22) Filed: Feb. 27, 2019

(65) Prior Publication Data
US 2019/0262298 A1 Aug. 29, 2019

Related U.S. Application Data

(60) Provisional application No. 62/785,980, filed on Dec. 28, 2018, provisional application No. 62/635,983, filed on Feb. 27, 2018.

(51) Int. Cl.
| | |
|---|---|
| *A61K 31/198* | (2006.01) |
| *C12N 9/02* | (2006.01) |
| *A61P 25/28* | (2006.01) |
| *A61P 25/24* | (2006.01) |
| *A61K 9/00* | (2006.01) |
| *A61K 35/741* | (2015.01) |
| *A61P 25/16* | (2006.01) |
| *A61K 35/00* | (2006.01) |

(52) U.S. Cl.
CPC .......... *A61K 31/198* (2013.01); *A61K 9/0053* (2013.01); *A61K 35/741* (2013.01); *A61P 25/16* (2018.01); *A61P 25/24* (2018.01); *A61P 25/28* (2018.01); *C12N 9/0073* (2013.01); *A61K 2035/115* (2013.01)

(58) Field of Classification Search
CPC ............ A61P 25/16; A61P 25/28; A61P 25/24
See application file for complete search history.

(56) References Cited

U.S. PATENT DOCUMENTS

| | | |
|---|---|---|
| 5,837,504 A | 11/1998 | Xun et al. |
| 2006/0141587 A1 | 6/2006 | Kramer et al. |

(Continued)

OTHER PUBLICATIONS

Genoscope. 2008. Submission of genomic DNA sequence for *E. coli* UMN026 to Genbank, and BLAST alignment of it with SEQ ID No. 1 and 2. PDF provided (Year: 2008).*

(Continued)

*Primary Examiner* — Erin M. Bowers
(74) *Attorney, Agent, or Firm* — McKee, Voorhees & Sease, PLC

(57) ABSTRACT

The present invention generally provides methods and compositions for the treatment of Parkinson's disease and depression and/or anxiety. The invention relates to recombinant microorganisms, particularly gut-colonizing probiotics, modified to produce L-DOPA.

29 Claims, 58 Drawing Sheets
(55 of 58 Drawing Sheet(s) Filed in Color)
Specification includes a Sequence Listing.

(56) References Cited

U.S. PATENT DOCUMENTS

2019/0038679 A1 2/2019 Lesser et al.
2019/0314313 A1 10/2019 Ellington et al.

OTHER PUBLICATIONS

Cassani, E. et al. 2011. Use of probiotics for the treatment of constipation in Parkinson's disease patients. Minerva gastroenterologica e dietologica, 57(2), pp. 117-121. (Year: 2011).*
Munoz, A et al. 2011. Metabolic engineering of *Escherichia coli* for improving L-3, 4-dihydroxyphenylalanine (L-DOPA) synthesis from glucose. Journal of Industrial Microbiology and Biotechnology, 38(11), p. 1845 (Year: 2011).*
Brod, L. et al. 2012. Are high doses of carbidopa a concern? A randomized, clinical trial in Parkinson's disease. Movement disorders, 27(6), pp. 750-753. (Year: 2012).*
PFM169 (pFM169 cloning vector. 2012. Aligment with references. PDF Provided.) (Year: 2012).*
Jongkees, B. et al. 2015. Effect of tyrosine supplementation on clinical and healthy populations under stress or cognitive demands—A review. Journal of psychiatric research, 70, pp. 50-57. (Year: 2015).*
Singh, A. et al. 2015. Pyrroloquinoline quinone (PQQ) producing *Escherichia coli* Nissle 1917 (EcN) alleviates age associated oxidative stress and hyperlipidemia, and improves mitochondrial function in ageing rats. Experimental gerontology, 66, pp. 1-9. (Year: 2015).*
Parashar A. et al. 2017. Gut microbiota: Implications in Parkinson's disease. Parkinsonism & related disorders, 38, pp. 1-7. (Year: 2017).*
Parashar et al., Parkinsonism and Related Disorders 38: 1-7 (2017).*
Muñoz et al., J. Ind. Microbiol. Biotechnol. 38: 1845-1852 (2011).*
Singh et al., Experimental Gerontology 66: 1-9 (2015).*
Cassani et al., Minerva Gastroenterol. Dietol. 57: 117-121 (2011).*
Brod et al., Movement Disorders 27(6): 750-753 (2012).*
Jongkees et al., J. Psychiatric Res. 70: 50-57 (2015).*
Genoscope. 2008. Submission of genomic DNA sequence for *E. coli* UMN026 to GenBank, and BLAST alignment (2008).*
PFM169 cloning vector alignment (2012).*

* cited by examiner

SEQUENCE LISTING

<160> NUMBER OF SEQ ID NOS: 23

<210> SEQ ID NO 1
<211> LENGTH: 1563
<212> TYPE: DNA
<213> ORGANISM: Escherichia coli

<400> SEQUENCE: 1

| | | |
|---|---|---|
| atgaaaccag aagatttccg cgccagtacc caacgtccgt tcaccgggga agagtatctg | 60 |
| aaaagcctgc aggatggtcg cgagatctat atctatggcg agcgagtgaa agacgtcact | 120 |
| actcatccgg catttcgtaa tgcggcagcg tctgttgccc aactgtacga cgcgctgcac | 180 |
| aaaccggaga tgcaggactc tctgtgttgg aacaccgaca ccggcagcgg cggctatacc | 240 |
| cataaattct ccgcgtggc gaaaagtgcc gacgacctgc ccagcaacg cgacgccatc | 300 |
| gctgagtggt cacgcctgag ctatggctgg atgggccgta ccccagacta caaagctgct | 360 |
| ttcggttgcg cactgggcgc gaatccgggc ttttacggtc agttcgagca gaacgcccgt | 420 |
| aactggtata cccgtattca ggaaactggc ctctacttta accacgcgat tgttaaccca | 480 |
| ccgatcgatc gtcatttgcc gaccgataaa gtgaaagacg tttacatcaa gctggaaaaa | 540 |
| gagactgacg ccgggattat cgttagcggt gcgaaagtgg ttgccaccaa ctcggcgctg | 600 |
| actcactaca acatggttgg cttcggctcg gcacaagtaa tgggcgaaaa cccggacttc | 660 |
| gcgctgatgt tcgttgcgcc aatggatgct gatggcgtga aattaatctc ccgcgcctct | 720 |
| tatgagatgt tcgcgggtgc taccggctca ccgtatgact accgctctc cagccgcttc | 780 |
| gatgagaatg atgcgattct ggtgatggat aacgtgctga tcccatggga aaacgtgctg | 840 |
| atctaccgcg attttgatcg ctgccgtcgc tggacgatgg aaggcggttt tgcccgtatg | 900 |
| tatccgctgc aagcctgtgt gcgcctggca gtgaaactcg acttcattac ggcactgctg | 960 |
| aaaaaatcac tcgaatgtac cggcacccctg gagttccgtg gtgtgcaggc cgatctcggt | 1020 |
| gaagtggtgg cgtggcgcaa caccttctgg gcattgagtg actcgatgtg ttctgaagcg | 1080 |
| acgccgtggg tcaacggggc ttatttaccg gatcatgccg cactgcaaac ctatcgcgta | 1140 |
| ctggcaccaa tggcctacgc gaagatcaaa acattatcg aacgcaacgt taccagtggc | 1200 |
| ctgatctacc tcccttccag tgcccgtgac ctgaacaatc cgcagatcga ccagtatctg | 1260 |
| gcgaagtatg tgcgcggttc gaatggtatg atcacgtcc agcgcatcaa gatcctcaaa | 1320 |
| ctgatgtggg acgccattgg cagcgagttt ggtggtcgcc acgaactgta tgaaatcaac | 1380 |
| tactccggta gccaggatga gattcgcctg cagtgtctgc gccaggcaca aagctccggc | 1440 |
| aatatggaca agatgatggc gatggttgat cgctgcctgt cggaatacga ccagaacggc | 1500 |
| tggactgtgc cgcacctgca caacaacgac gatatcaaca tgctggataa gctgctgaaa | 1560 |
| taa | 1563 |

<210> SEQ ID NO 2
<211> LENGTH: 513
<212> TYPE: DNA
<213> ORGANISM: Escherichia coli

<400> SEQUENCE: 2

| | | |
|---|---|---|
| atgcaattag atgaacaacg cctgcgcttt cgtgacgcga tggccagcct gtcggcagcg | 60 |
| gtaaatatta tcaccaccga gggcgacacc ggacaatgcg ggattacggc aacggctgtc | 120 |
| tgctcggtca cggatacacc accgtcgctg atggtgtgca ttaacgccaa cagtgcgatg | 180 |
| aacccggttt tcagggcaa cggcaagttg tgcgtcaacg tcctcaacca tgagcaggaa | 240 |

```
ctgatggcac gccacttcgc gggcatgaca ggcatggcga tggaagagcg ttttagcctc    300
tcatgctggc aaaaaggtcc gctggcgcag ccggtgctaa aaggttcgct ggccagtctt    360
gaaggtgaga tccgcgatgt gcaggcaatt ggcacacatc tggtgtatct ggtggagatt    420
aaaaacatca tcctcagtgc agaaggtcac ggacttatct actttaaacg ccgtttccat    480
ccggtgatgc tggaaatgga agctgcgatt taa                                 513
```

```
<210> SEQ ID NO 3
<211> LENGTH: 2149
<212> TYPE: DNA
<213> ORGANISM: Artificial Sequence
<220> FEATURE:
<223> OTHER INFORMATION: Synthetic construct

<400> SEQUENCE: 3
```

```
gaaggagata tacatatgaa acccgaagat ttccgtgctt caacacagcg ccctttcact     60
ggggaagaat acctgaagag cctgcaagac ggtcgtgaaa tttatattta cggggagcgt    120
gtgaaggatg ttacgaccca tccagccttt cgcaacgccg ctgcgtctgt ggcgcagttg    180
tatgatgcgt tacacaaacc tgagatgcag gattcgttgt gctggaacac agacacgggt    240
tcgggaggat atactcataa attttttcgc gttgctaagt cggcagacga cctgcgccaa    300
caacgtgatg ctattgctga gtggtcacgt ctgtcgtacg ggtggatggg acgtacaccc    360
gattataaag cggcgtttgg atgcgcattg ggagctaacc ctggattcta tggacagttc    420
gagcagaatg cccgcaactg gtacacacgc attcaagaaa ctgggttgta ttttaatcac    480
gccattgtca atccgccgat cgatcgccac ctgcccacgg ataaagtaaa agatgtatat    540
attaagttgg aaaagagac agacgcaggg atcattgtat caggcgccaa ggtggttgcg    600
accaattctg ccctgacgca ctacaacatg atcggctttg gatctgctca agtgatgggg    660
gaaaaccccg attttgcact tatgtttgta gcccccatgg acgctgacgg ggttaaactg    720
attagccgcg catcgtacga aatggtcgcc ggggccacag gcagtccgta cgattatcct    780
ttatctagtc gcttcgacga aaacgacgcg atcttagtga tggataacgt cctgattcct    840
tgggagaacg tcctgatcta tcgtgatttc gaccgctgcc gtcgttggac tatggaagga    900
ggcttcgctc gcatgtaccc tttgcaagcc tgtgtacgcc ttgctgtcaa acttgatttc    960
atcactgcgc ttttgaagaa atcgttagag tgtactggga cgctggagtt ccgtggtgtc   1020
caagccgacc ttggcgaggt ggtggcttgg cgtaatactt tctgggcatt atccgactcc   1080
atgtgctcgg aagcaacccc ctgggtcaat ggggcatacc ttcccgatca cgccgctctt   1140
caaacctatc gcgtacttgc gcctatggct tatgctaaga ttaaaaatat tatcgaacgt   1200
aatgtgactt ccggcttaat ttacttgccc tccagcgcgc gcgatctgaa taatcctcaa   1260
atcgaccagt atttagcgaa gtatgttcgc gggagcaacg ggatggatca tgtccagcgc   1320
atcaaaatcc ttaagttaat gtgggatgcc attggttcag aatttggcgg gcgtcatgaa   1380
ctttatgaaa ttaattactc tggctcgcaa gacgagatcc gtctgcaatg cttgcgccag   1440
gcgcaatcct cgggtaatat ggataagatg atggctatgg tagaccgctg cctgtccgag   1500
tacgaccaaa acgatggac ggtcccccat ctgcataaca acgatgacat taacatgctg   1560
gataagctgc tgaaataacg cagcaggagg ttaagatgca gctggacgaa caacgcctgc   1620
gctttcgtga cgcaatggcg agtttgagtg cagccgttaa tatcattaca acagaagggg   1680
acgcaggtca atgtggaatc actgcaacgg ccgtgtgctc agttacagac actccgcctt   1740
```

```
cattaatggt atgcatcaat gctaactcgg ctatgaatcc tgtcttccaa ggcaatggga    1800
aattatgtgt gaacgtcctg aaccatgagc aagaactgat ggcacgccac ttcgcaggca    1860
tgacaggtat ggcaatggag gagcgtttta gcttgtcttg ctggcaaaag ggaccactgg    1920
cccaaccagt tttgaagggg tctcttgcat cattagaagg ggaaatccgc gatgtccagg    1980
cgattggtac acacctggtt taccttgtcg agatcaagaa catcatttta tccgcagagg    2040
gccacgggct gatttacttt aaacgccgct tccatccggt tatgctggaa atggaagctg    2100
caatttaagt aaggaaacat ttatgcgcct gcatcatcac caccatcac                2149

<210> SEQ ID NO 4
<211> LENGTH: 35
<212> TYPE: DNA
<213> ORGANISM: Artificial Sequence
<220> FEATURE:
<223> OTHER INFORMATION: Synthetic construct

<400> SEQUENCE: 4
ttgacggcta gctcagtcct aggtacagtg ctagc                               35

<210> SEQ ID NO 5
<211> LENGTH: 35
<212> TYPE: DNA
<213> ORGANISM: Artificial Sequence
<220> FEATURE:
<223> OTHER INFORMATION: Synthetic construct

<400> SEQUENCE: 5
tttacggcta gctcagtcct aggtactatg ctagc                               35

<210> SEQ ID NO 6
<211> LENGTH: 35
<212> TYPE: DNA
<213> ORGANISM: Artificial Sequence
<220> FEATURE:
<223> OTHER INFORMATION: Synthetic construct

<400> SEQUENCE: 6
ttgacggcta gctcagtcct aggtatagtg ctagc                               35

<210> SEQ ID NO 7
<211> LENGTH: 35
<212> TYPE: DNA
<213> ORGANISM: Artificial Sequence
<220> FEATURE:
<223> OTHER INFORMATION: Synthetic construct

<400> SEQUENCE: 7
ttgacagcta gctcagtcct aggtataatg ctagc                               35

<210> SEQ ID NO 8
<211> LENGTH: 35
<212> TYPE: DNA
<213> ORGANISM: Artificial Sequence
<220> FEATURE:
<223> OTHER INFORMATION: Synthetic construct

<400> SEQUENCE: 8
tttacagcta gctcagtcct aggtattatg ctagc                               35

<210> SEQ ID NO 9
<211> LENGTH: 35
<212> TYPE: DNA
<213> ORGANISM: Artificial Sequence
```

<220> FEATURE:
<223> OTHER INFORMATION: Synthetic construct

<400> SEQUENCE: 9
ttgacagcta gctcagtcct aggtactgtg ctagc        35

<210> SEQ ID NO 10
<211> LENGTH: 35
<212> TYPE: DNA
<213> ORGANISM: Artificial Sequence
<220> FEATURE:
<223> OTHER INFORMATION: Synthetic construct

<400> SEQUENCE: 10
ctgatagcta gctcagtcct agggattatg ctagc        35

<210> SEQ ID NO 11
<211> LENGTH: 35
<212> TYPE: DNA
<213> ORGANISM: Artificial Sequence
<220> FEATURE:
<223> OTHER INFORMATION: Synthetic construct

<400> SEQUENCE: 11
ttgacagcta gctcagtcct aggtattgtg ctagc        35

<210> SEQ ID NO 12
<211> LENGTH: 35
<212> TYPE: DNA
<213> ORGANISM: Artificial Sequence
<220> FEATURE:
<223> OTHER INFORMATION: Synthetic construct

<400> SEQUENCE: 12
tttacggcta gctcagtcct aggtatagtg ctagc        35

<210> SEQ ID NO 13
<211> LENGTH: 35
<212> TYPE: DNA
<213> ORGANISM: Artificial Sequence
<220> FEATURE:
<223> OTHER INFORMATION: Synthetic construct

<400> SEQUENCE: 13
tttacggcta gctcagccct aggtattatg ctagc        35

<210> SEQ ID NO 14
<211> LENGTH: 35
<212> TYPE: DNA
<213> ORGANISM: Artificial Sequence
<220> FEATURE:
<223> OTHER INFORMATION: Synthetic construct

<400> SEQUENCE: 14
ctgacagcta gctcagtcct aggtataatg ctagc        35

<210> SEQ ID NO 15
<211> LENGTH: 35
<212> TYPE: DNA
<213> ORGANISM: Artificial Sequence
<220> FEATURE:
<223> OTHER INFORMATION: Synthetic construct

<400> SEQUENCE: 15
tttacagcta gctcagtcct agggactgtg ctagc        35

<210> SEQ ID NO 16
<211> LENGTH: 35
<212> TYPE: DNA
<213> ORGANISM: Artificial Sequence
<220> FEATURE:
<223> OTHER INFORMATION: Synthetic construct

<400> SEQUENCE: 16
tttacggcta gctcagtcct aggtacaatg ctagc    35

<210> SEQ ID NO 17
<211> LENGTH: 35
<212> TYPE: DNA
<213> ORGANISM: Artificial Sequence
<220> FEATURE:
<223> OTHER INFORMATION: Synthetic construct

<400> SEQUENCE: 17
ctgatagcta gctcagtcct agggattatg ctagc    35

<210> SEQ ID NO 18
<211> LENGTH: 35
<212> TYPE: DNA
<213> ORGANISM: Artificial Sequence
<220> FEATURE:
<223> OTHER INFORMATION: Synthetic construct

<400> SEQUENCE: 18
ctgatggcta gctcagtcct agggattatg ctagc    35

<210> SEQ ID NO 19
<211> LENGTH: 35
<212> TYPE: DNA
<213> ORGANISM: Artificial Sequence
<220> FEATURE:
<223> OTHER INFORMATION: Synthetic construct

<400> SEQUENCE: 19
tttatggcta gctcagtcct aggtacaatg ctagc    35

<210> SEQ ID NO 20
<211> LENGTH: 35
<212> TYPE: DNA
<213> ORGANISM: Artificial Sequence
<220> FEATURE:
<223> OTHER INFORMATION: Synthetic construct

<400> SEQUENCE: 20
tttatagcta gctcagccct tggtacaatg ctagc    35

<210> SEQ ID NO 21
<211> LENGTH: 35
<212> TYPE: DNA
<213> ORGANISM: Artificial Sequence
<220> FEATURE:
<223> OTHER INFORMATION: Synthetic construct

<400> SEQUENCE: 21
ttgacagcta gctcagtcct agggactatg ctagc    35

<210> SEQ ID NO 22
<211> LENGTH: 35
<212> TYPE: DNA
<213> ORGANISM: Artificial Sequence
<220> FEATURE:
<223> OTHER INFORMATION: Synthetic construct

```
<400> SEQUENCE: 22
ttgacagcta gctcagtcct agggattgtg ctagc                          35

<210> SEQ ID NO 23
<211> LENGTH: 35
<212> TYPE: DNA
<213> ORGANISM: Artificial Sequence
<220> FEATURE:
<223> OTHER INFORMATION: Synthetic construct

<400> SEQUENCE: 23
ttgacggcta gctcagtcct aggtattgtg ctagc                          35
```

L-DOPA MICROBIOME THERAPY

CROSS-REFERENCE TO RELATED APPLICATIONS

This application claims priority to provisional applications U.S. Ser. No. 62/635,983 filed Feb. 27, 2018 and U.S. Ser. No. 62/785,980 filed Dec. 28, 2018, which are incorporated herein by reference in their entireties.

FIELD OF THE INVENTION

This invention relates generally to a recombinant microbial cell, specifically to a probiotic strain engineered to produce L-DOPA, and methods of using the same to provide L-DOPA in a sustained manner for treatment of Parkinson's disease and other Parkinsonian disorders. Uses of the recombinant microbial cell for treatment of depression, anxiety and other related mood disorders are also disclosed.

BACKGROUND OF THE INVENTION

More than 10 million people worldwide, and one million Americans have Parkinson's disease (PD), and approximately 50,000 new cases are diagnosed each year, with the incidence among aging population exceeding that for other younger segments of the US population. In addition, Parkinsonian disorders including progressive supranuclear palsy (PSP) and multiple system atrophy (MSA) have overlapping neurological deficits and clinical pathology with PD. The cardinal pathology of PD is progressive neurodegeneration of dopamine-producing neurons in substantia nigra, contributing to dopamine deficiency that manifest in severe motor symptoms including rigidity, bradykinesia, tremors, and postural instability. The amino acid L-DOPA is the precursor to the neurotransmitter dopamine, and has been used for the treatment of a variety of neurological disorders including PD. The discovery of dopamine replacement therapy with Levodopa (L-DOPA) for PD represents one of the most remarkable success stories in the history of medicine. For decades, L-DOPA is the drug most often prescribed because it's unparalleled symptomatic relief to PD patients. Unfortunately, L-DOPA gold standard therapy met inherent side effects commonly referred to L-DOPA induced dyskinesia (LID). Although neurochemical basis of LID is not completely understood, dopamine receptor sensitization due to pulsated delivery of L-DOPA in form of 100-500 mg tablet 2 times day is considered to be major reason for the LID. The clinical diagnosis of L-DOPA drug fluctuations include peak dose, off period dystonia, and diphasic dyskinesia. In the face of antiparkinsonian treatment, the lack of effective treatment to control LID remains by far the most challenging problem.

Therefore, it is an object of the present invention to provide methods and compositions to deliver L-DOPA in a sustained manner thereby avoiding pulsated delivery and the L-DOPA induced dyskinesia associated with the standard treatment regimen. Other objects will become apparent from the description of the invention which follows.

BRIEF SUMMARY OF THE INVENTION

The present invention provides methods and compositions comprising a recombinant microbial cell capable of producing L-DOPA, for use in the treatment of Parkinson's disease and depression and/or anxiety. In some embodiments, the recombinant microbial cell colonizes the gut of the subject in need of treatment, thereby providing L-DOPA in a sustained manner.

In one embodiment, the disclosure provides a method for providing a subject in need thereof with a treatment for Parkinson's disease comprising administering to the subject an effective amount of a composition comprising a recombinant microbial cell capable of producing L-DOPA.

In another embodiment, methods of treating depression and/or anxiety and improving motivation to do difficult tasks are provided. The method comprises administering to the subject in need thereof an effective amount of a composition comprising a recombinant microbial cell capable of producing L-DOPA.

In the preceding embodiments of the invention, the recombinant microbial cell can be a probiotic. In an exemplary embodiment, the probiotic is *E. coli* Nissle 1917. In some embodiments, the composition is administered orally. In some embodiments, the composition is administered on alternate days. In certain embodiments, the subject is a mammal. In a preferred embodiment the mammal is a human. In some embodiments, the effective amount of the recombinant microbial cell comprises from about $10^6$ CFU to about $10^{12}$ CFU. In a preferred embodiment, the effective amount comprises about $10^9$ CFU of the recombinant microbial cell.

In some embodiments, an effective amount of a DOPA decarboxylase inhibitor is co-administered with the recombinant microbial cell composition. In a preferred embodiment, the DOPA decarboxylase inhibitor is carbidopa or benserazide. In certain embodiments, the composition further comprises L-Tyrosine. In other embodiments, supplemental L-Tyrosine is not required.

In some embodiments, the recombinant microbial cell capable of producing L-DOPA comprises a hpaB nucleotide sequence and a hpaC nucleotide sequence. In some embodiments, the hpaB nucleotide sequence is the sequence set forth in SEQ ID NO: 1 and the hpaC nucleotide sequence is the sequence set forth in SEQ ID NO: 2. In another embodiment, the recombinant microbial cell capable of producing L-DOPA comprises the hpaBC$_{syn}$ nucleotide sequence set forth in SEQ ID NO: 3.

In yet another embodiment, a pharmaceutical composition for use in the treatment of Parkinson's disease is provided. In some embodiments, the pharmaceutical composition is for use in the treatment of depression and/or anxiety.

In some embodiments, the pharmaceutical composition comprises a recombinant microbial cell capable of producing L-DOPA and colonizing the gut of a subject, thereby providing L-DOPA in a sustained manner. In some embodiments, recombinant microbial cell of the pharmaceutical composition is a probiotic. In an exemplary embodiment, the probiotic is *E. coli* Nissle 1917.

In some embodiments, the pharmaceutical composition comprises from about $10^6$ CFU to about $10^{12}$ CFU of the recombinant microbial cell. In a preferred embodiment, the pharmaceutical composition comprises about $10^9$ CFU of the recombinant microbial cell. In some embodiments, the pharmaceutical composition further comprises L-Tyrosine. In another embodiment, the pharmaceutical composition further comprises a pharmaceutically acceptable carrier.

While multiple embodiments are disclosed, still other embodiments of the present invention will become apparent to those skilled in the art from the following detailed description, which shows and describes illustrative embodiments of the invention. Accordingly, the figures and detailed description are to be regarded as illustrative in nature and not restrictive.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 3A shows moving track, FIG. 3B shows rotorod performance, FIG. 3C shows TH immunocytochemistry (DAB stain), and FIG. 3D shows depletion of striatal dopamine.

FIGS. 4A-4B show Morris water maze test, and FIGS. 4C-4D show social discrimination test.

FIG. 5A shows whole gut transit time. FIG. 5B shows colon transit time. FIG. 5C shows rate of colonic motility. FIG. 5D shows colon length. Representative photographs showing smaller colon length in 24-wk old MitoPark mice compared to control mice are shown on the right. FIG. 5E shows dopamine levels in the colon of 24-wk old MitoPark mice compared to control mice. FIG. 5F shows representative 60×IHC Images showing decreased number of TH positive neurons in the myenteric plexus of the colon in MitoPark mice.

FIG. 6A shows colonies counts. Fecal pellets were collected 6 and 24 h post treatment and subjected to kanamycin-selective colonies count. FIG. 6B shows L-DOPA levels. Two colonies were picked and grown in LB medium containing kanamycin (50 µg/ml), L-tyrosine (10 mg/ml), and ascorbic acid (1-10 mg/ml) for 12 h. L-DOPA levels in medium were assessed by HPLC. HpaBC E. coli was used as a positive control.

FIG. 7A shows moving track. FIG. 7B shows horizontal activity. FIG. 7C shows total distance. FIG. 7D shows striatal tissues collected and assayed for dopamine levels.

FIG. 9A shows time course of Plasma L-DOPA levels and FIG. 9B shows plasma L-DOPA levels post 24 hr treatment. Plasma was collected prior to treatment and on days 1, 2 and 10 post-treatment and stored frozen. Plasma L-DOPA levels were then quantified using the HPLC electrochemical detection method.

FIG. 10A shows Versamax Motor activity map, FIG. 10B shows horizontal activity, FIG. 10C shows total distance traveled, and FIG. 10D shows stereotypic activity.

FIG. 12A shows time immobile and FIG. 12B shows distance traveled in forced swim test. Animals were assessed weekly for 4 weeks for depression-like behavior.

Representative data shown for age 20 weeks. See brief description of FIG. 10 for animal treatment paradigm.

Figure 13:
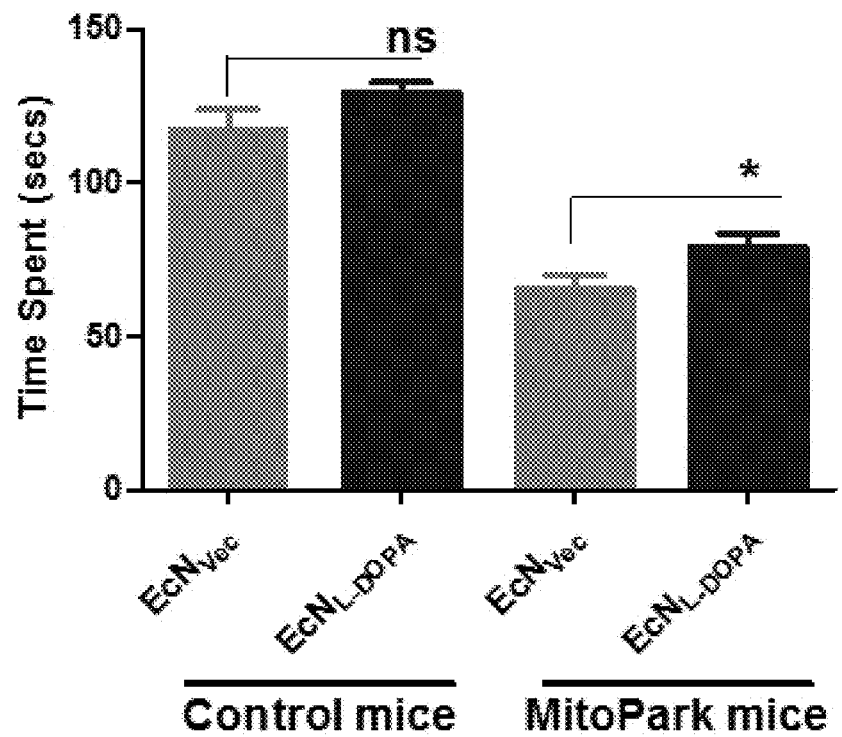

FIG. 13 shows E. coli Nissle 1917 L-DOPA-producing bacteria ($EcN^1_{L\text{-}DOPA}$) protect against progressive loss of vestibulomotor function and motor coordination. Animals were assessed weekly for vestibulomotor function and motor coordination using the Rotarod system every week for 4 weeks. Representative data shown for age 20 weeks. See brief description of FIG. 10 for animal treatment paradigm.

Figure 14A:
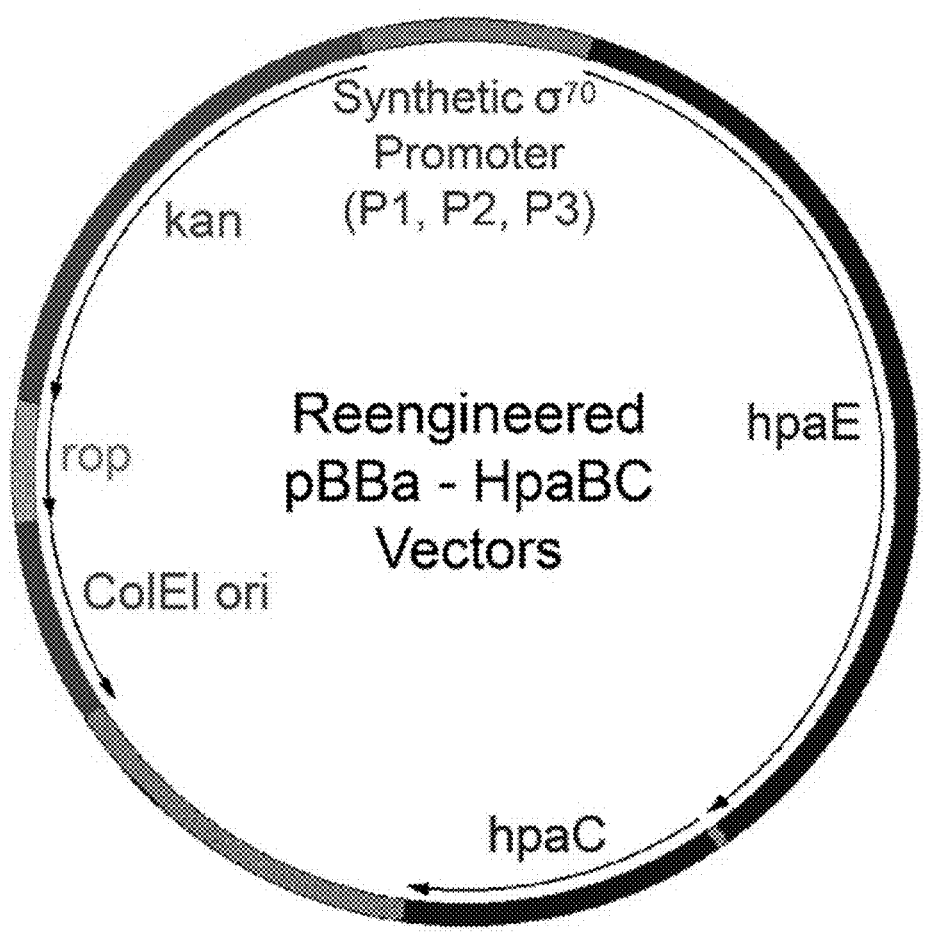
Figure 14B:
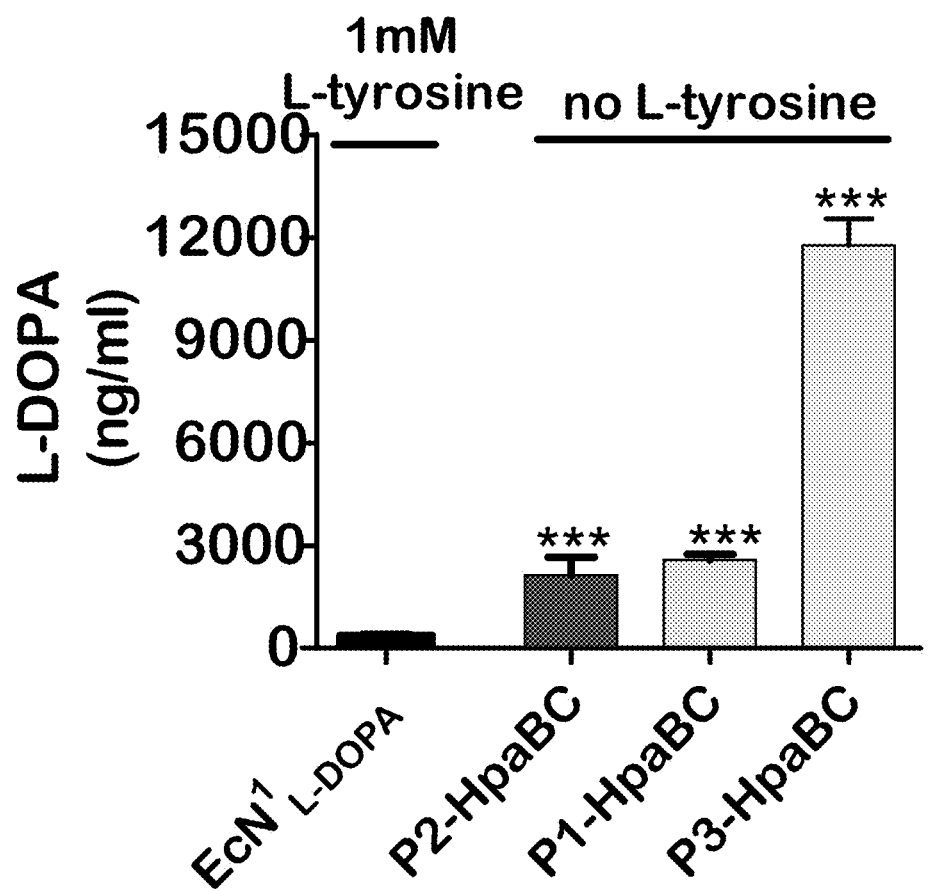

FIG. 14A shows the re-construction of L-DOPA-expressing plasmids. FIG. 14B shows quantification of L-DOPA yield. The newly generated L-DOPA-expressing systems produced significantly higher amounts of L-DOPA compared to the RSF1030-based EcN$^1_{L\text{-}DOPA}$ system, even without adding L-tyrosine. ***, p<0.001, compared to EcN$^1_{L\text{-}DOPA}$, by one-way ANOVA, n=4-6.

Figure 15A:
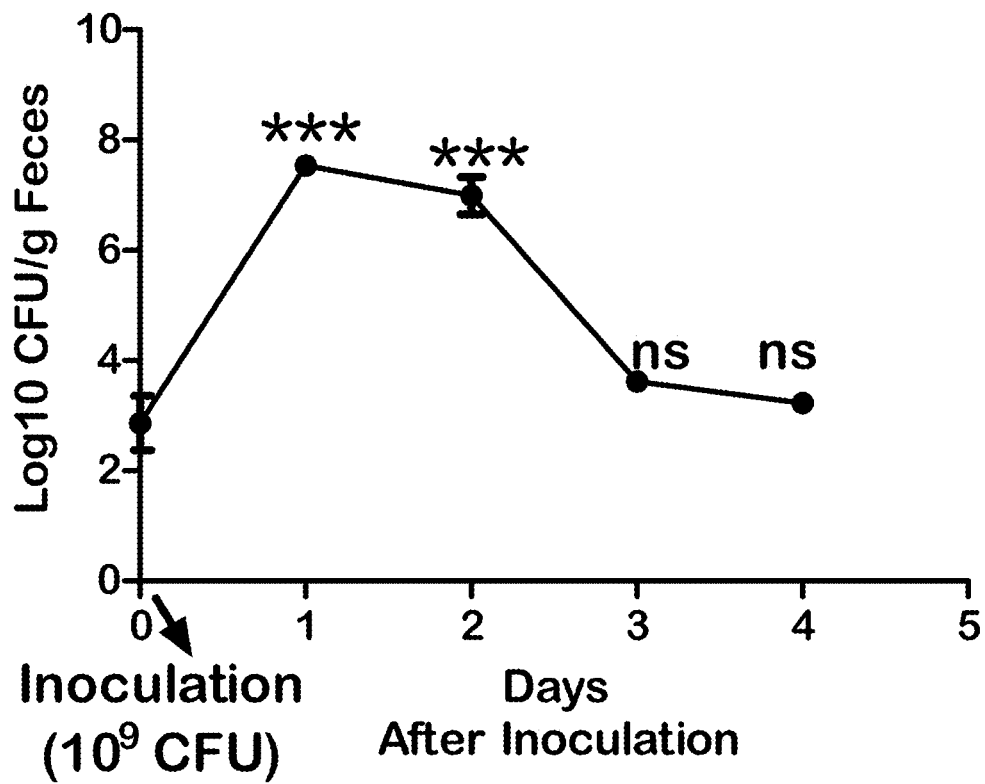
Figure 15B:
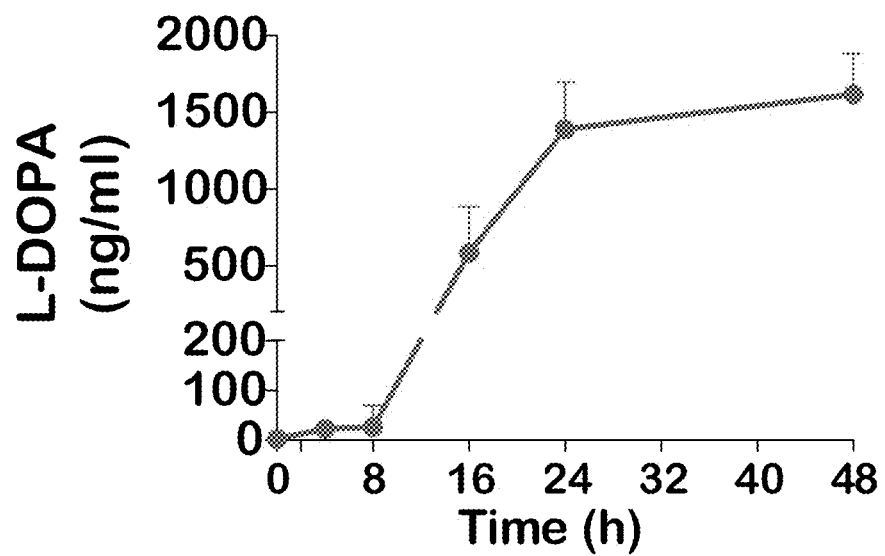

FIGS. 15A-15B show C57 black mice orally received a single dose of EcN$^2_{L\text{-}DOPA}$ ($10^9$ CFU) or PBS, both in combination with benserazide (Bz). FIG. 15A shows colonization profile. Fecal pellets were collected daily for 4 days and subjected to qPCR-based analysis of colonization. FIG. 15B shows plasma L-DOPA levels in EcN$^2_{L\text{-}DOPA}$-treated mice as determined by HPLC. Data represented as mean±SEM from 6 mice.

Figure 16A:
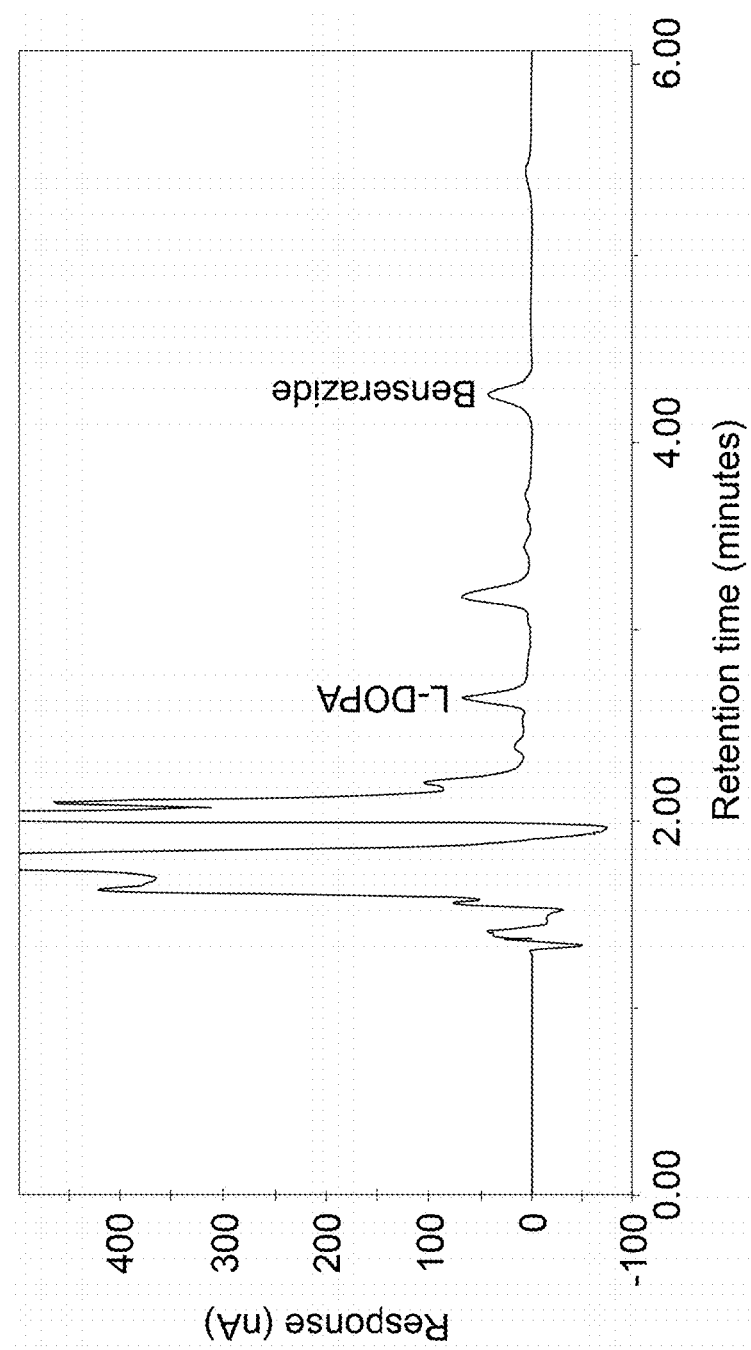
Figure 16B:
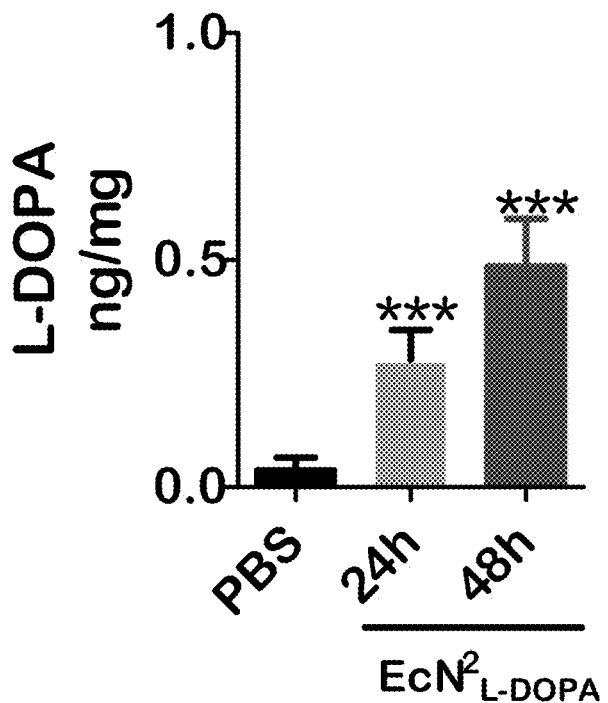
Figure 16C:
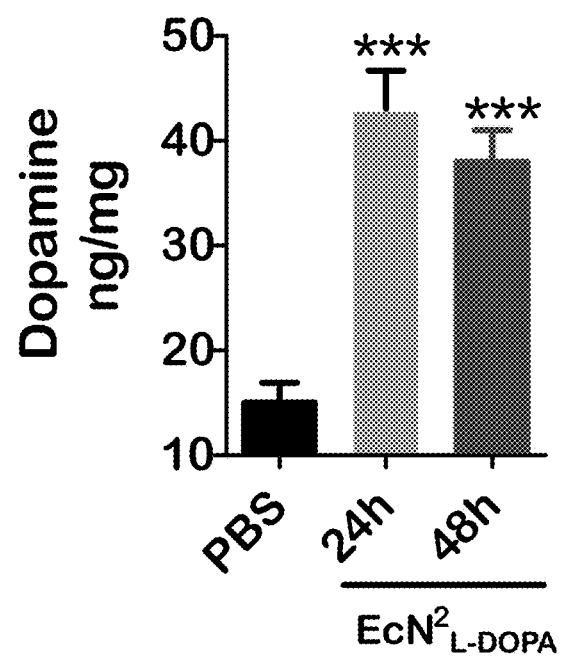
Figure 16D:
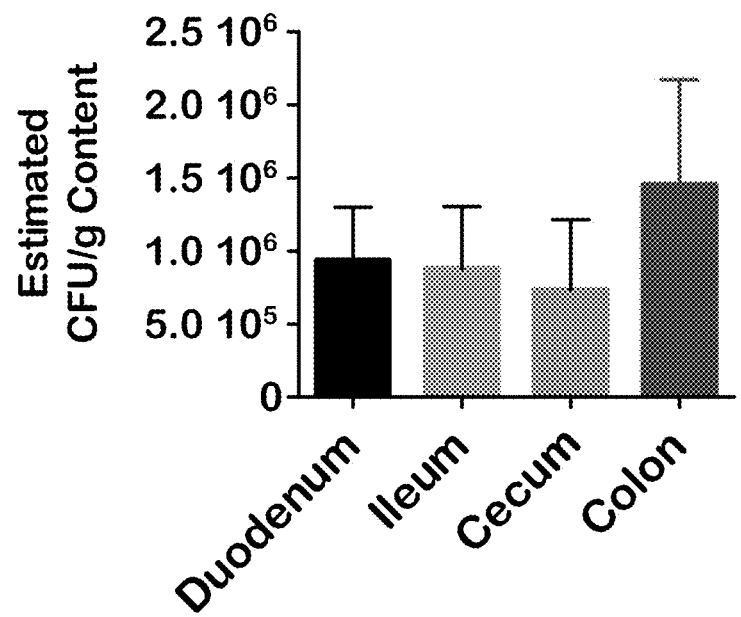

FIGS. 16A-16D show C57 black mice orally received a single dose of EcN$^2_{L\text{-}DOPA}$ ($10^9$ CFU) or PBS, in combination with a single oral dose of Bz (50 mg/kg, 3 times/day) for 1 and 2 days. FIG. 16A shows HPLC detection of plasma Bz at 30 h after the first Bz treatment. FIGS. 16B-16C shows L-DOPA levels in plasma and striatal tissues analyzed by HPLC. FIG. 16D shows qPCR analysis of colonization from intestinal content scraped off from various gut segments. (***, p<0.01 by one-way ANOVA). n=6.

Figure 17A:
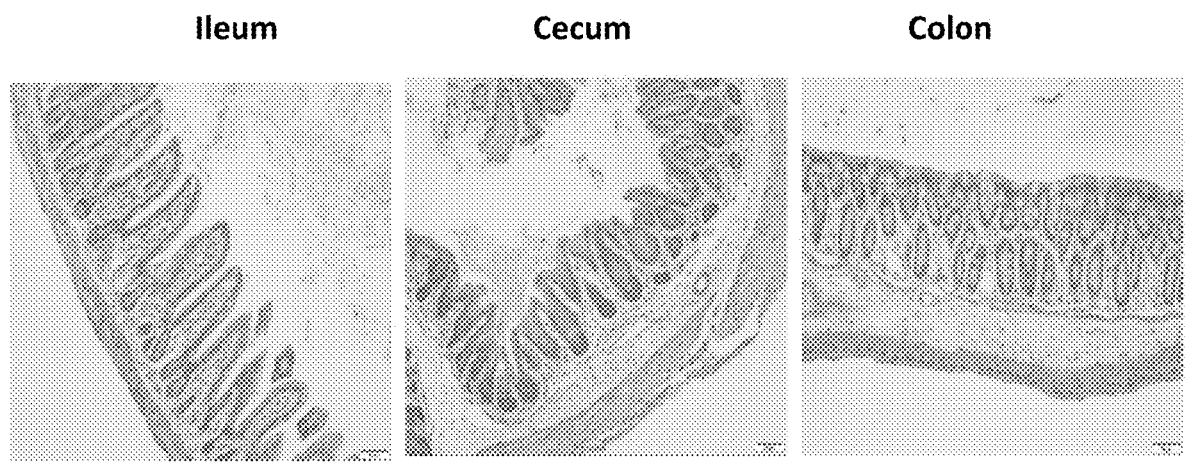
Figure 17B:
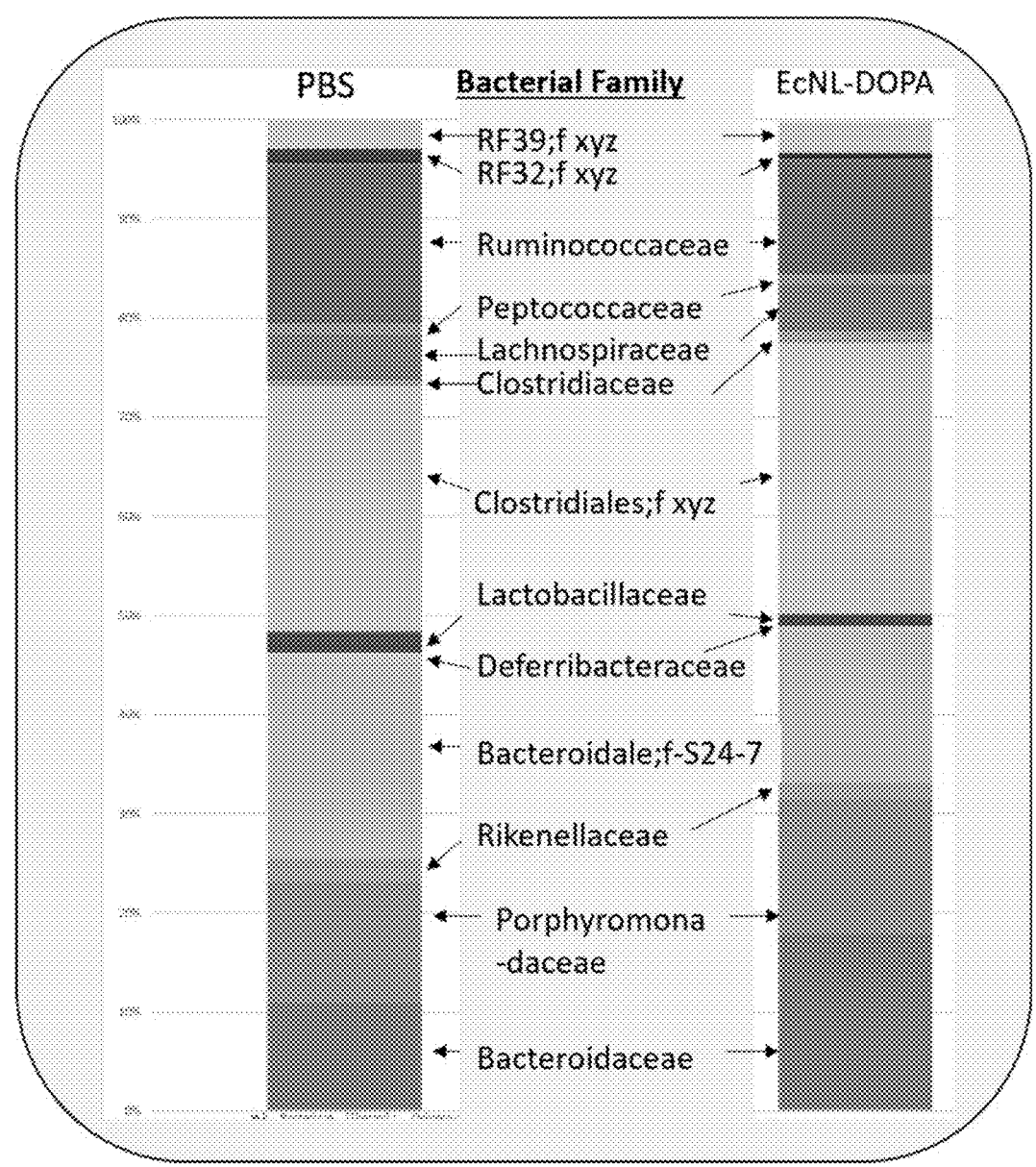

FIGS. 17A-17B show C57 black mice treated with a single daily dose of EcN$^1_{L\text{-}DOPA}$ ($10^9$ CFU) in combination with carbidopa (10 mg/kg, i.p.) for 1 week. FIG. 17A shows representative H&E stained ileum, cecum and colon sections from EcN$^1_{L\text{-}DOPA}$-treated mice. n=3. FIG. 17B shows taxonomy bar chart. Genomic DNA isolated from fecal pellets were subjected to PCR amplification of V4 variable region of 16S rRNA performed at the ISU DNA facility on the Illumina MiSeq Platform. The sequences were analyzed using QIIME. The taxonomy summary at the family level was shown. xyz, unnamed family. n=4.

Figure 18A:
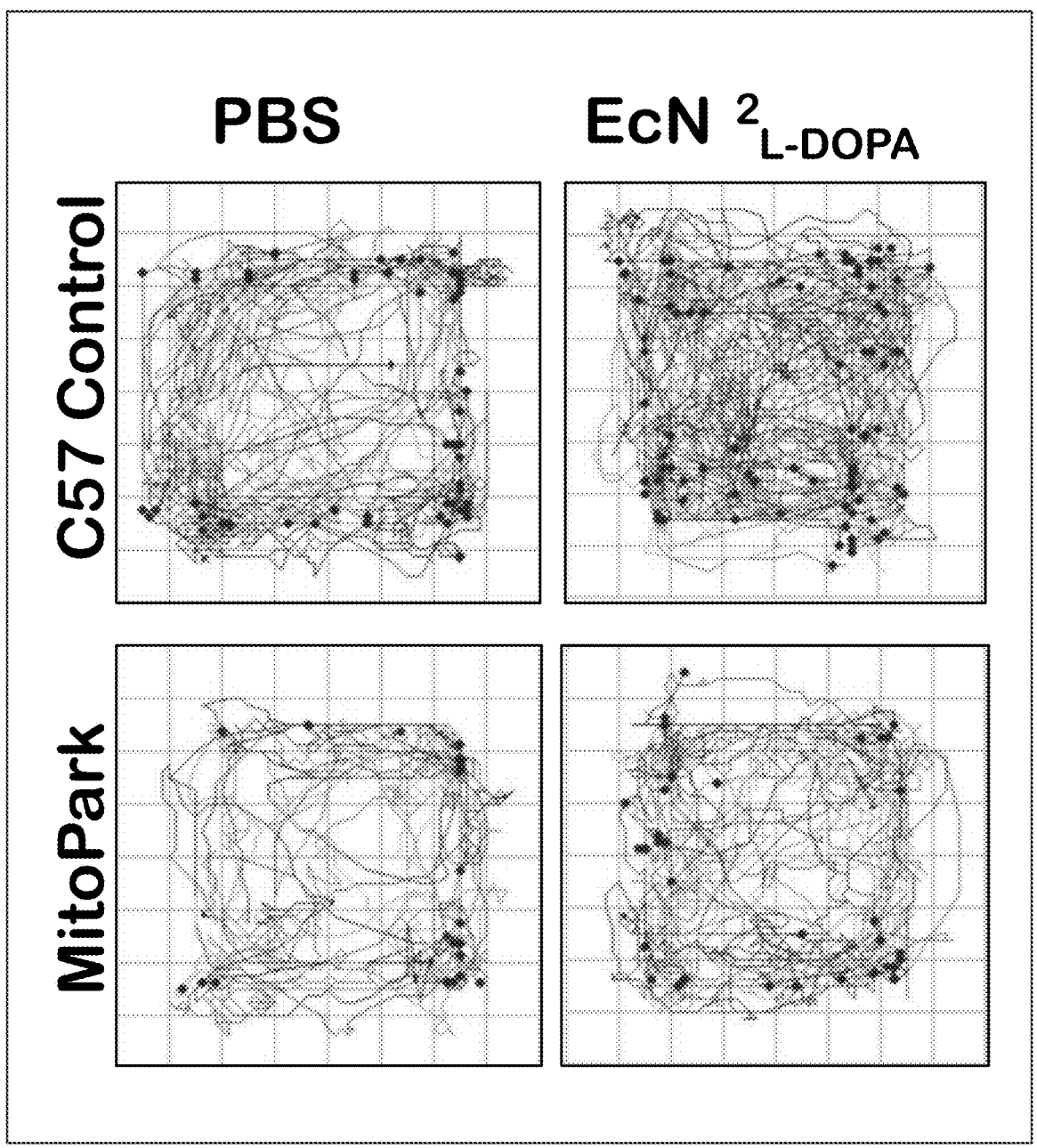
Figure 18B:
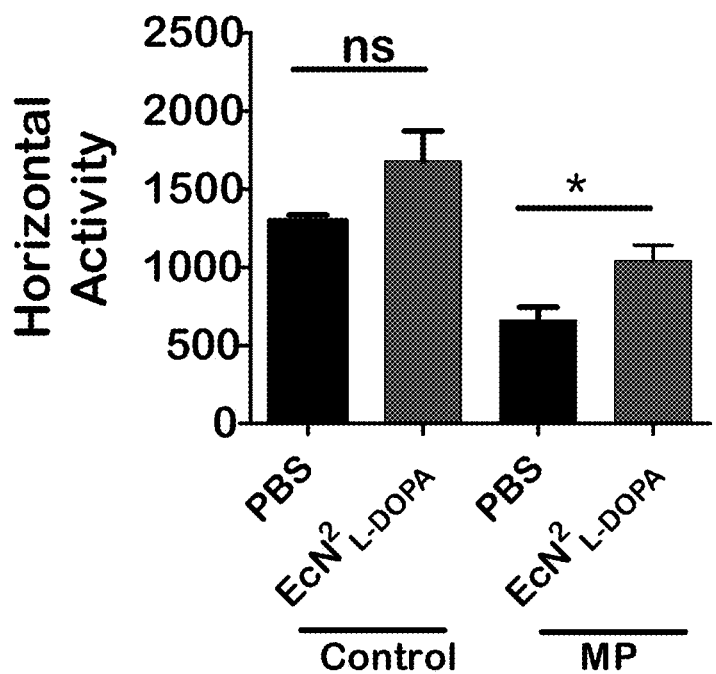
Figure 18C:
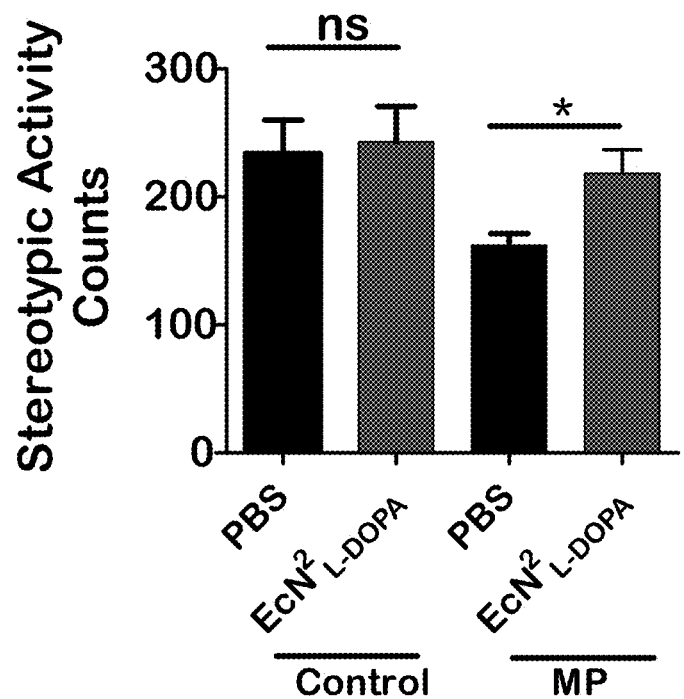

FIGS. 18A-18C show MitoPark (MP) and age-matched control mice (11-16 weeks old, male and female, n=4-5) received oral administration of $10^9$ CFU of either of EcN$^2_{L\text{-}DOPA}$ or PBS and co-administered with a single dose of Bz (12.5 mg/kg i.p.) on alternate days for 1 week. Animals were assessed weekly for exploratory locomotor activity via an open-field test recorded using the Versamax computerized activity monitoring system. Representative data shown for post 1-week treatment. FIG. 18A shows Versamax Motor activity map, FIG. 18B shows horizontal activity, and FIG. 18C shows stereotypic activity. (*, p<0.05 by one-way ANOVA). ns, not significant.

Figure 19:
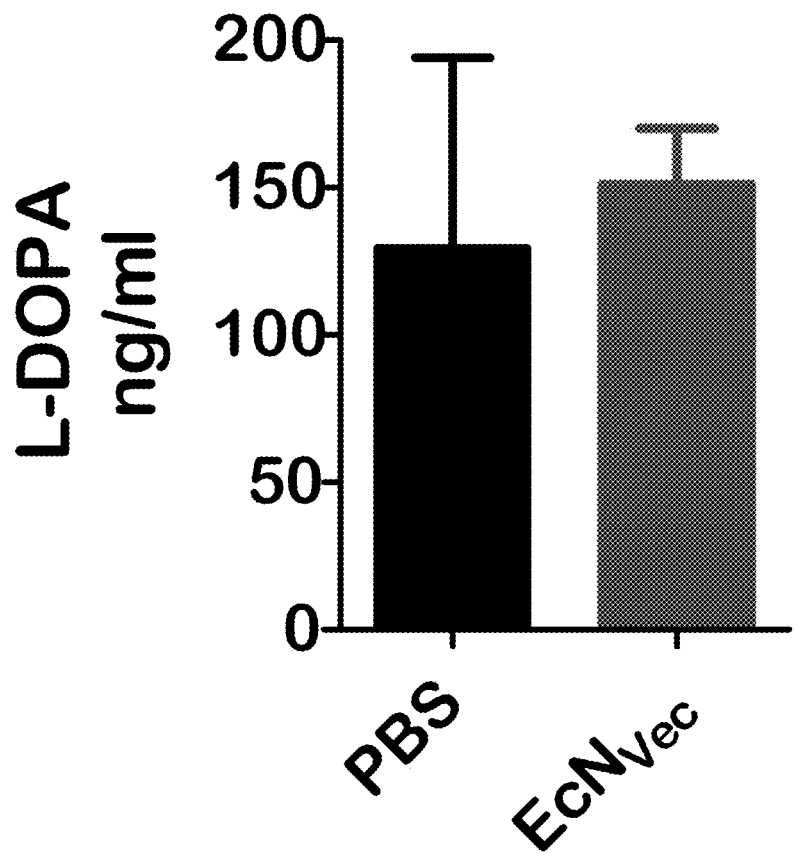

FIG. 19 shows C57 black mice received oral administration of $10^9$ CFU of either of EcN$_{Vec}$ or PBS and co-administered with a single dose of Bz (12.5 mg/kg i.p.) for 1 day. Plasma L-DOPA levels were analyzed by HPLC. n=3.

Figure 20:
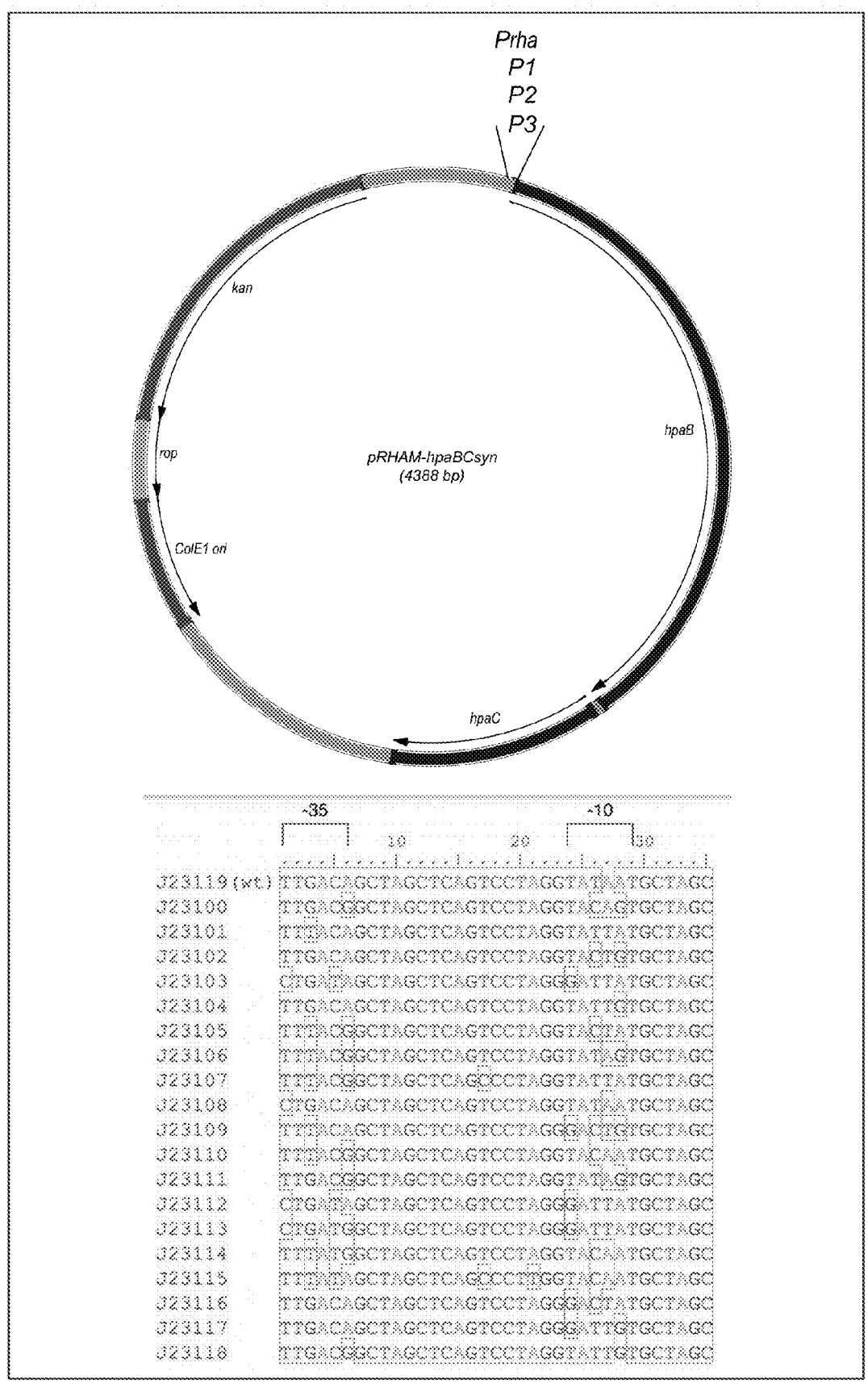

FIG. 20 shows plasmid constructs used for expression of hpaBC in EcN. Synthetic hpaBC genes were cloned into the pRHAM vector yielding the plasmid shown. The rha promoter and operator were subsequently replaced with 3 individual constitutive promoters (P1, P2, P3). Along with the coding regions for hpaB and hpaC, additional plasmid features include: kan, kanamycin resistance; rop, control of plasmid copy number; ColEIori, origin of replication (SEQ ID NOs: 4-23).

Figure 21A:
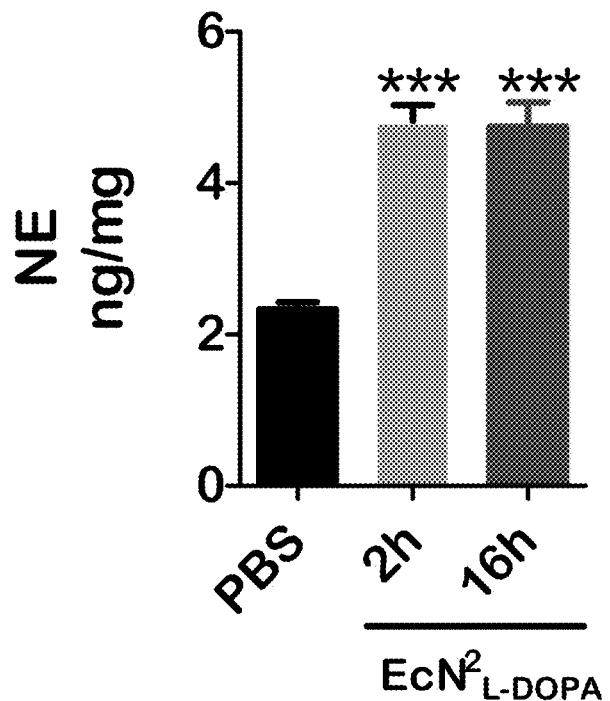
Figure 21B:
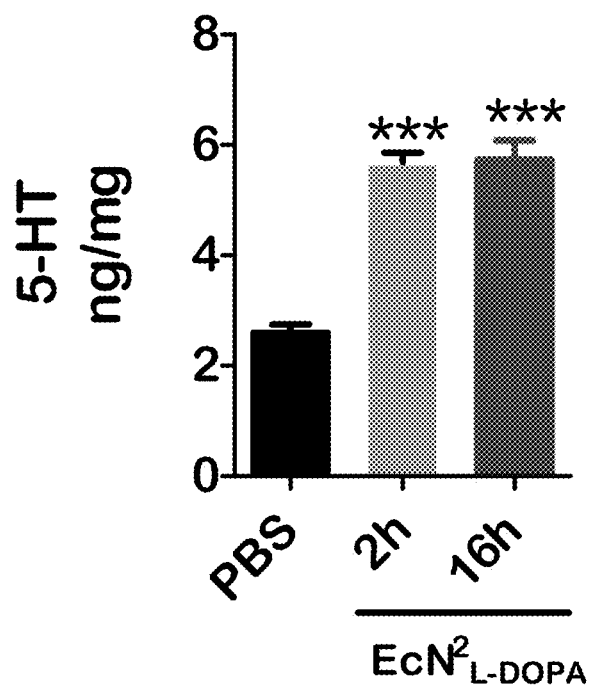
Figure 21C:
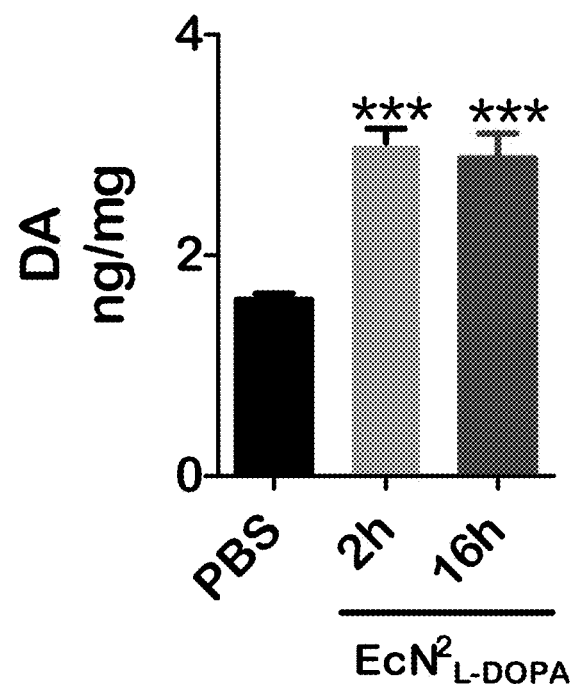

FIGS. 21A-21C show C57 black mice orally received a single dose of EcN$^2_{L\text{-}DOPA}$ ($10^9$ CFU) or PBS, in combination with a single oral dose of Bz (12.5 mg/kg, ip) for 2-16 h. (A-C) NE, 5-HT and DA levels in frontal cortex tissues were analyzed by HPLC. (***, p<0.01 by one-way ANOVA). n=3-6. FIG. 21A shows norepinephrine levels, FIG. 21B shows 5-hydroxytryptamine levels, and FIG. 21C shows dopamine levels.

Figure 22A:
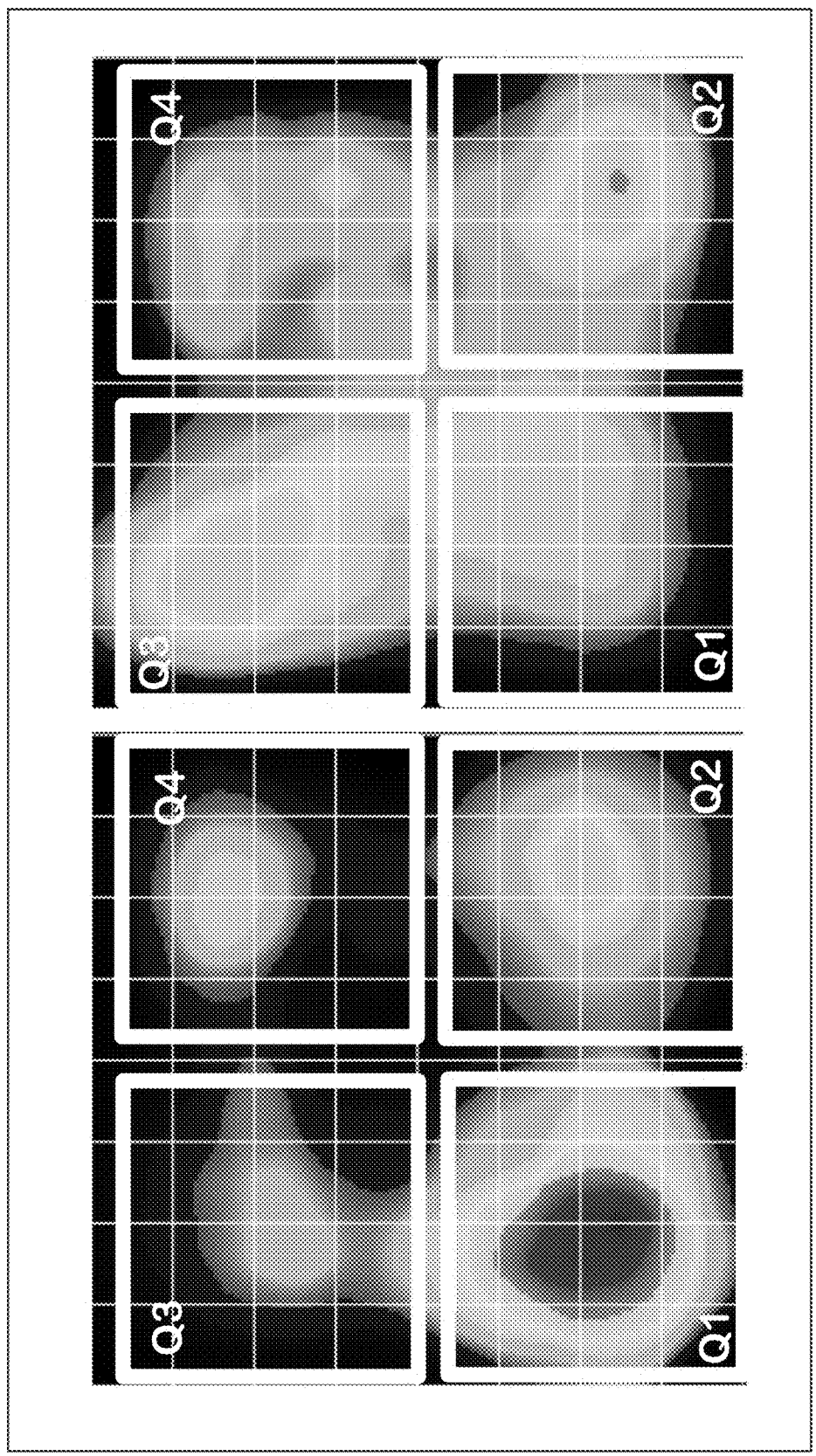
Figure 22B:
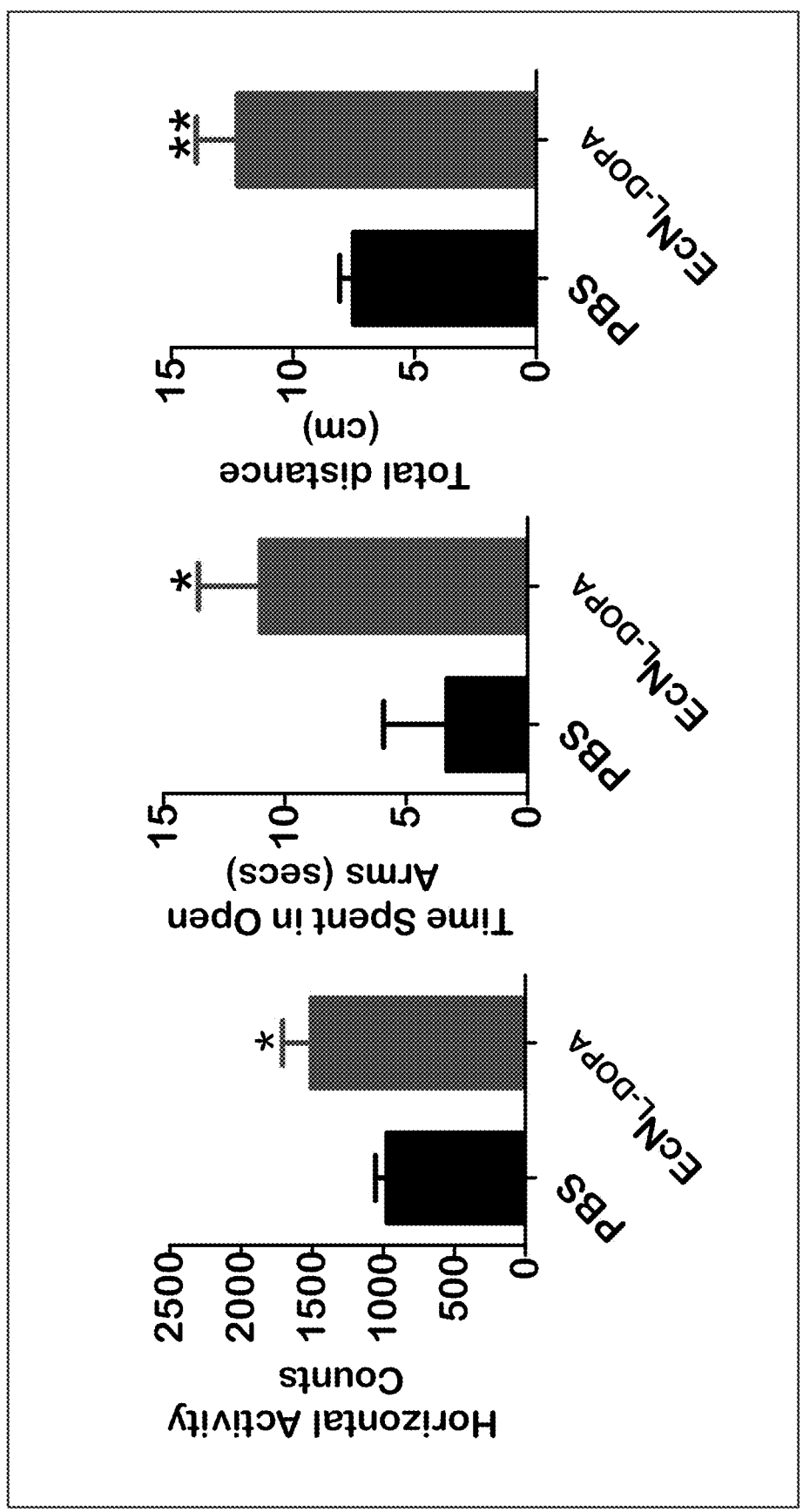
Figure 22C:
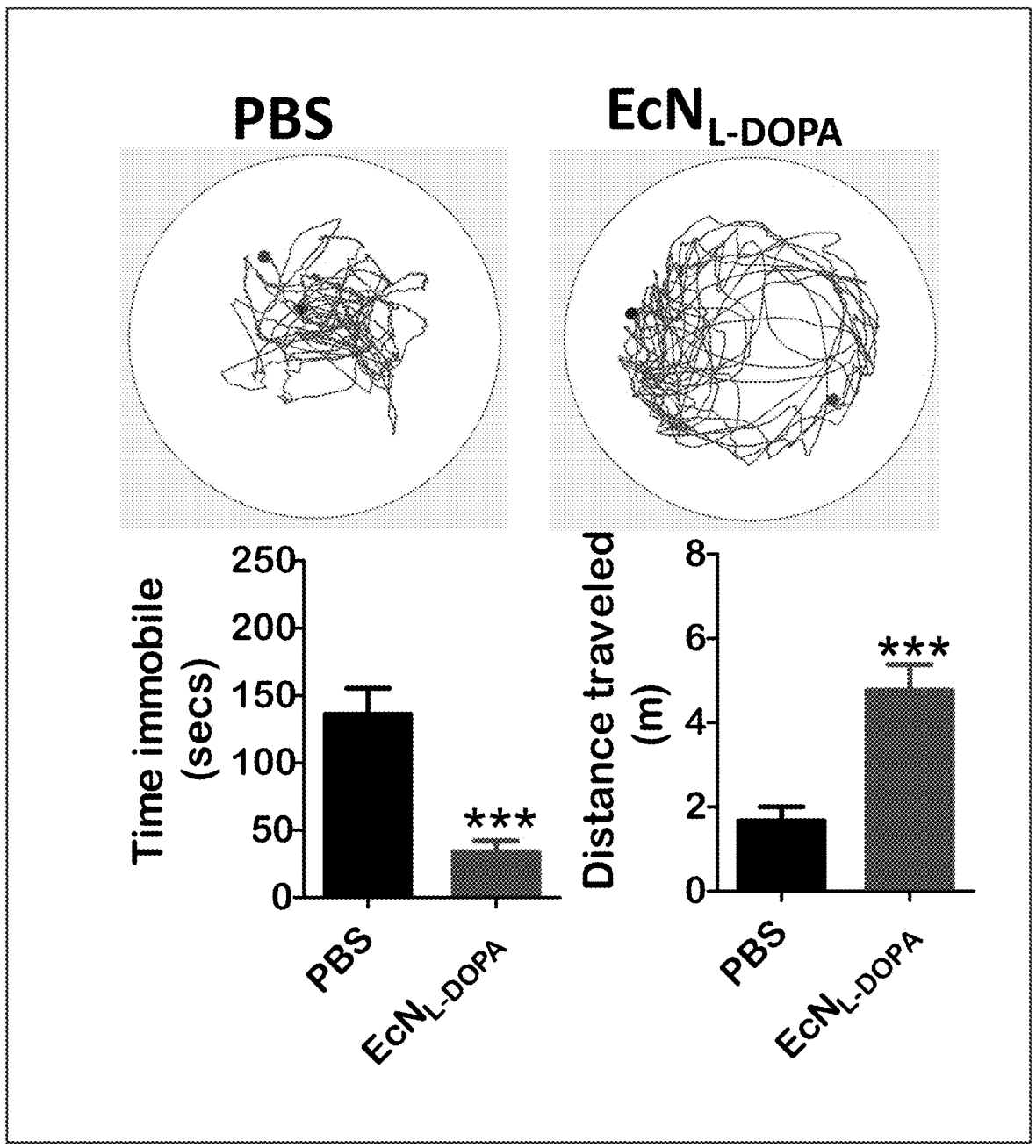

FIGS. 22A-22C shows mice (15-17 weeks old, n=3-8) received oral administration of $10^9$ CFU of either of EcN$^2_{L\text{-}DOPA}$ or PBS and co-administered with a single dose of Bz (12.5 mg/kg i.p.) on alternate days. Animals were assessed weekly for 4 weeks for anxiety-like (FIGS. 22A-22B) and depression-like behavior (FIG. 22C). FIG. 22A shows EcN$^2_{L\text{-}DOPA}$ reduces anxiety-like behavior in C57 mice. Left: Representative heat map of animal's exploratory behavior in VersaMax OFT. Quadrants (Q3,4) are the open exposed quadrants while Q1,2 are closed. FIG. 22B shows elevated plus maze (EPM). Right: quantitation of horizontal activities. Representative data shown for post 3-week treatment. Center: time spent in open arms. Right: total distance in EPM. Representative data shown for post 4-week treatment. FIG. 22C shows forced swim test (FST). Top: Move tracks are shown. Bottom left: time immobile. Bottom right: distance traveled in FST. Representative data shown for post 2-week treatment. (*, p<0.05, , p<0.01, *, p<0.001 by Student's t-test).

DETAILED DESCRIPTION OF THE INVENTION

The present invention provides methods and compositions comprising a recombinant microbial cell capable of producing L-DOPA. The recombinant microbial cell colonizes the gut of the subject in need of treatment and provides L-DOPA in a sustained manner to avoid the development of Levodopa-induced dyskinesia (LID).

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The singular terms "a", "an", and "the" include plural referents unless context clearly indicates otherwise. Similarly, the word "or" is intended to include "and" unless the context clearly indicate otherwise. The word "or" means any one member of a particular list and also includes any combination of members of that list.

Numeric ranges recited within the specification, including ranges of "greater than," "at least", or "less than" a numeric value, are inclusive of the numbers defining the range and include each integer within the defined range. For example, when a range of "1 to 5" is recited, the recited range should be construed as including ranges "1 to 4", "1 to 3", "1-2", "1-2 & 4-5", "1-3 & 5", and the like.

The term "about" as used herein, refers to variation in the numerical quantity that can occur, for example, through typical measuring techniques and equipment, with respect to any quantifiable variable, including, but not limited to, mass, volume, time, distance, wave length, frequency, voltage, current, and electromagnetic field. Further, given solid and liquid handling procedures used in the real world, there is certain inadvertent error and variation that is likely through differences in the manufacture, source, or purity of the ingredients used to make the compositions or carry out the methods and the like. The term "about" also encompasses amounts that differ due to different equilibrium conditions for a composition resulting from a particular initial mixture. The term "about" also encompasses these variations. Whether or not modified by the term "about," the claims include equivalents to the quantities.

As used herein, the terms "microbe", "microbial cell", or "microorganism" refer to an organism of microscopic, submicroscopic, or ultramicroscopic size that typically consists of a single cell. Examples of microorganisms include bacteria, viruses, fungi, certain algae, and protozoa. The term "microbial" indicates pertaining to, or characteristic of a microorganism.

The term "microbiome", as used herein, refers to a population of microorganisms from a particular environment, including the environment of the body or a part of the body. The term is interchangeably used to address the population of microorganisms itself (sometimes referred to as the microbiota), as well as the collective genomes of the microorganisms that reside in the particular environment. The term "environment," as used herein, refers to all surrounding circumstances, conditions, or influences to which a population of microorganisms is exposed. The term is intended to include environments in a subject, such as a human and/or animal subject.

The recombinant cell according to the invention may be constructed from any suitable host cell. The host cell may be an unmodified cell or may already be genetically modified. In one embodiment, the cell is a recombinant microbial cell. In one embodiment, the recombinant microbial cell is recombinant gut-colonizing microbial cell. In one embodiment, the cell can be a prokaryotic cell or a eukaryotic cell. In one embodiment, the cell is a prokaryotic cell.

In one embodiment, the recombinant microbial cell is a nonpathogenic bacterial cell. In some embodiments, the recombinant microbial cell is a commensal bacterial cell. In some embodiments, the recombinant microbial cell is a yeast cell. In some embodiments, the recombinant microbial cell is a probiotic. In some embodiments, the recombinant microbial cell is a naturally pathogenic microbial cell that is modified or mutated to reduce or eliminate pathogenicity.

"Probiotic" is used to refer to live, non-pathogenic microorganisms, e.g., bacteria, which can confer health benefits to a host organism that contains an appropriate amount of the microorganism. Some species, strains, and/or subtypes of non-pathogenic microorganisms are currently recognized as probiotic. Examples of probiotic microorganisms include, but are not limited to, *Bifidobacteria, Escherichia coli, Lactobacillus*, and *Saccharomyces*, e.g., *Bifidobacterium bifidum, Enterococcus faecium, Escherichia coli* strain Nissle, *Lactobacillus acidophilus, Lactobacillus bulgaricus, Lactobacillus paracasei, Lactobacillus plantarum*, and *Saccharomyces boulardii* (Dinleyici et al., 2014; U.S. Pat. Nos. 5,589,168; 6,203,797; 6,835,376).

Examples of probiotic bacteria include, but are not limited to, specific probiotic strains of *Lactobacillus, Bifidobacterium, Lactococcus, Enterococcus, Streptococcus, Pediococcus, Leuconostoc, Bacillus*, or *Escherichia coli*.

In some embodiments, a probiotic *Lactobacillus* may include, without limitation, a *Lactobacillus reuteri, Lactobacillus plantarum, Lactobacillus casei* (such as *Lactobacillus casei* Shirota), *Lactobacillus salivarius, Lactobacillus paracasei, Lactobacillus lactis, Lactobacillus acidophilus, Lactobacillus sakei, Lactobacillus brevis, Lactobacillus buchneri, Lactobacillus fermentum, Lactobacillus delbrueckii, Lactobacillus delbrueckii* subsp. *bulgaricus, Lactobacillus helveticus, Lactobacillus garvieae, Lactobacillus acetotolerans, Lactobacillus agilis, Lactobacillus algidus, Lactobacillus alimentarius, Lactobacillus amylolyticus, Lactobacillus amylophilus, Lactobacillus amylovorus, Lactobacillus animalis, Lactobacillus aviarus, Lactobacillus bifermentans, Lactobacillus bulgaricus, Lactobacillus carnis, Lactobacillus caternaformis, Lactobacillus cellobiosis, Lactobacillus collinoides, Lactobacillus confuses, Lactobacillus coryniformis, Lactobacillus crispatus, Lactobacillus curvatus, Lactobacillus divergens, Lactobacillus farciminis, Lactobacillus fructivorans, Lactobacillus fructosus, Lactobacillus gallinarum, Lactobacillus gasseri, Lactobacillus graminis, Lactobacillus haiotoierans, Lactobacillus hamster, Lactobacillus heterohiochii, Lactobacillus hilgardii, Lactobacillus homohiochii, Lactobacillus iners, Lactobacillus intestinalis, Lactobacillus jensenii, Lactobacillus johnsonii, Lactobacillus kandleri, Lactobacillus kefiri, Lactobacillus kefuranofaciens, Lactobacillus kefirgranum, Lactobacillus kunkeei, Lactobacillus leichmannii, Lactobacillus llndnerl, Lactobacillus malefermentans, Lactobacillus mall, Lactobacillus maltaromicus, Lactobacillus manihotivorans, Lactobacillus minor, Lactobacillus minutus, Lactobacillus mucosae, Lactobacillus murinus, Lactobacillus nagelii, Lactobacillus oris, Lactobacillus panis, Lactobacillus parabuchneri, Lactobacillus paracasei, Lactobacillus parakefiri, Lactobacillus paralimentarius, Lactobacillus paraplantarum, Lactobacillus pentosus, Lactobacillus perolens, Lactobacillus piscicola, Lactobacillus plantarum, Lactobacillus pontis, Lactobacillus rhamnosus, Lactobacillus rhamnosus* GG, *Lactobacillus rimae, Lactobacillus rogosae, Lactobacillus ruminis, Lactobacillus sanfranciscensis, Lactobacillus sharpeae, Lactobacillus suebicus, Lactobacillus trichodes, Lactobacillus uli, Lactobacillus vaccinostercus, Lactobacillus vaginalis, Lactobacillus viridescens, Lactobacillus vitulinus, Lactobacillus xylosus, Lactobacillus yamanashiensis*, or a *Lactobacillus zeae*.

In some embodiments, a probiotic *Escherichia coli* may be *E. coli* Nissle 1917. As used herein, the term "*Escherichia*" refers to a genus of Gram-negative, non-spore forming, facultatively anaerobic, rod-shaped bacteria from the family Enterobacteriaceae. The genus *Escherichia* include various species, such as *Escherichia coli*. The terms "*Escherichia coli* Nissle 1917" or "EcN" as used herein refer to a non-pathogenic Gram-negative probiotic bacteria *Escherichia coli* strain that is capable of colonizing the human gut. In an exemplary embodiment, the probiotic is the *Escherichia coli* strain Nissle 1917.

*Escherichia coli* Nissle 1917 has evolved into one of the best characterized probiotics (Ukena et al., 2007). The strain is characterized by its complete harmlessness (Schultz, 2008), and has GRAS (generally recognized as safe) status (Reister et al., 2014). *E. coli* strain Nissle 1917 lacks defined virulence factors such as alpha-hemolysin, other toxins, and mannose-resistant hemagglutinating adhesins (Blum et al. Infection. 23(4): 234-236 (1996)), P-fimbrial adhesins, and the semirough lipopolysaccharide phenotype and expresses fitness factors such as microcins, ferritins, six different iron uptake systems, adhesins, and proteases, which support its survival and successful colonization of the human gut (Grozdanov et al. *J Bacteriol*. 186(16): 5432-5441 (2004)). As early as in 1917, *E. coli* Nissle was packaged into medicinal capsules, called MUTAFLOR®, for therapeutic use. *E. coli* Nissle has since been used to treat ulcerative colitis in humans in vivo (Rembacken et al., 1999), to treat inflammatory bowel disease, Crohn's disease, and pouchitis in humans in vivo (Schultz, 2008), and to inhibit enteroinvasive *Salmonella, Legionella, Yersinia*, and *Shigella* in vitro (Altenhoefer et al., 2004). It is commonly accepted that E. coli Nissle's therapeutic efficacy and safety have convincingly been proven (Ukena et al., 2007).

Examples of *Escherichia coli* Nissle 1917 bacteria include those available as DSM 6601 from the German Collection for Microorganisms in Braunschweig, Germany or commercially as the active component in MUTAFLOR® (Ardeypharm GmbH, Herdecke, Germany).

In some embodiments, a probiotic *Bifidobacterium* may be *Bifidobacterium infantis*, *Bifidobacterium adolescentis*, *Bifidobacterium animalis* subsp *animalis*, *Bifidobacterium longum*, *Bifidobacterium fidobacterium breve*, *Bifidobacterium bifidum*, *Bifidobacterium animalis* subsp. *lactis* or *Bifidobacterium lactis*, such as *Bifidobacterium lactis* DN-173 010.

In some embodiments, a probiotic *Bacillus* may be *Bacillus coagulans*. In some embodiments, a probiotic *Lactococcus* may be *Lactococcus lactis* subsp. *Lactis* such as *Lactococcus lactis* subsp. *lactis* CV56. In some embodiments, a probiotic *Enterococcus* may be *Enterococcus durans*. In some embodiments, a probiotic *Streptococcus* may be *Streptococcus thermophilus*.

In some embodiments, the probiotic bacterium may be an auxotrophic strain designed, for example, to limit its survival outside of the human or animal intestine, using standard techniques.

The probiotic may be a variant or a mutant strain of bacterium (Arthur et al., 2012; Cuevas-Ramos et al., 2010; Olier et al., 2012; Nougayrede et al., 2006). Non-pathogenic bacteria may be genetically engineered to enhance or improve desired biological properties, e.g., survivability. Non-pathogenic bacteria may be genetically engineered to provide probiotic properties. Probiotic cells may be genetically engineered to enhance or improve probiotic properties, e.g., enhance gut colonization.

Bacterial strains can be readily obtained using standard methods known in the art. For example, a commensal bacterium such as *Escherichia coli* Nissle 1917 can be obtained from a commercial preparation of the probiotic MUTAFLOR®. Bacteria can be cultured using standard methods known in the art.

One of ordinary skill in the art would appreciate that the genetic modifications disclosed herein may be modified and adapted for other species, strains, and subtypes of bacteria or other microorganisms.

"Gut" refers to the organs, glands, tracts, and systems that are responsible for the transfer and digestion of food, absorption of nutrients, and excretion of waste. In humans, the gut comprises the gastrointestinal tract, which starts at the mouth and ends at the anus, and additionally comprises the esophagus, stomach, small intestine, and large intestine. The gut also comprises accessory organs and glands, such as the spleen, liver, gallbladder, and pancreas. The upper gastrointestinal tract comprises the esophagus, stomach, and duodenum of the small intestine. The lower gastrointestinal tract comprises the remainder of the small intestine, i.e., the jejunum and ileum, and all of the large intestine, i.e., the cecum, colon, rectum, and anal canal. Bacteria can be found throughout the gut, e.g., in the gastrointestinal tract, and particularly in the intestines.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides. Unless otherwise indicated, the term includes reference to the specified sequence as well as the complementary sequence thereof.

As used herein, the terms "peptide", "polypeptide", and "protein" will be used interchangeably to refer to a chain of amino acids each of which is joined to the next amino acid by a peptide bond. In one aspect, this term also includes post translational modifications of the polypeptide, for example, glycosylations, acetylations, phosphorylations and the like. Included within the definition are, for example, peptides containing one or more analogues of an amino acid or labeled amino acids and peptidomimetics.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

In one aspect, there is provided an isolated nucleic acid molecule comprising 4-hydroxyphenylacetate 3-monooxygenase (HpaB) and its FAD reductase (HpaC). In one embodiment, the nucleic acid molecule has at least 80%, 85%, 90%, 95%, 96%, 97%, 98%, 99%, or 100% sequence identity to SEQ ID NO: 1, SEQ ID NO: 2, and/or SEQ ID NO: 3. In one embodiment, the nucleic acid molecule comprises or consists of the nucleic acid sequence of SEQ ID NO: 1, SEQ ID NO: 2, and/or SEQ ID NO: 3. In one embodiment, the nucleic acid molecule is a vector. In one embodiment, the nucleic acid molecule is a vector comprising an insert comprising or consisting of SEQ ID NO: 1, SEQ ID NO: 2, and/or SEQ ID NO: 3. In one embodiment, transformation of a microbial cell with the vector results in the production of L-DOPA. Additionally, other HpaB and HpaC nucleic acid sequences may be identified through databases such as Genbank.

In one aspect, the present disclosure is directed towards recombinant *Escherichia coli* Nissle 1917(EcN) cell, or a variant thereof, transformed with a nucleic acid molecule containing one or more genes involved in the biosynthesis of L-DOPA. As demonstrated in the Examples, the inventors have determined that EcN cells transformed with HpaB and HpaC are useful for the recombinant production of L-DOPA.

Accordingly, in one embodiment there is provided a recombinant EcN cell or variant thereof comprising HpaB (SEQ ID NO: 1) and HpaC (SEQ ID NO: 2), or HpaBC (SEQ ID NO: 3). Optionally, the recombinant EcN cell comprises one or more genes with sequence identity to HpaB (SEQ ID NO: 1), HpaC (SEQ ID NO: 2), or HpaBC (SEQ ID NO: 3). For example, in one embodiment, the cell comprises one or more nucleic acid sequences with at least 70%, 75%, 80%, 85%, 90%, 95%, 96%, 97%, 98%, 99% or 100% sequence identity to one or more of SEQ ID NO: 1, SEQ ID NO: 2, and SEQ ID NO: 3.

Sequence identity can be determined according to sequence alignment methods known in the art. Examples of these methods include computational methods such as those that make use of the BLAST algorithm, available online from the National Center for Biotechnology Information. Sequence identity is most preferably assessed by the algorithm of BLAST version 2.1 advanced search. BLAST is a series of programs that are available, for example, online from the National Institutes of Health. References to BLAST searches are: Altschul, S. F., Gish, W., Miller, W., Myers, E. W. & Lipman, D. J. (1990) "Basic local alignment search tool." J. Mol. Biol. 215:403410; Gish, W. & States, D. J. (1993) "Identification of protein coding regions by database similarity search." Nature Genet. 3:266272; Madden, T. L., Tatusov, R. L. & Zhang, J. (1996) "Applications of network BLAST server" Meth. Enzymol. 266:131_141; Altschul, S. F., Madden, T. L., Schaffer, A. A., Zhang, J., Zhang, Z., Miller, W. & Lipman, D. J. (1997) "Gapped BLAST and PSI BLAST: a new generation of protein database search programs." Nucleic Acids Res. 25:33893402; Zhang, J. & Madden, T. L. (1997) "Power-BLAST: A new network BLAST application for interactive or automated sequence analysis and annotation." Genome Res. 7:649656.

Percent sequence identity or homology between two sequences is determined by comparing a position in the first sequence with a corresponding position in the second sequence. When the compared positions are occupied by the same nucleotide or amino acid, as the case may be, the two sequences are conserved at that position. The degree of conservation between two sequences is often expressed as a percentage representing the ratio of the number of matching positions in the two sequences to the total number of positions compared. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above.

Nucleic acid hybridization may also be used to identify substantially similar nucleic acid molecules to those reported herein. The present nucleic acid molecules described herein may be used to identify genes encoding substantially similar polypeptides/proteins expected to have similar function. Nucleic acid hybridization may be conducted under stringent conditions. Substantially similar sequences are defined by their ability to hybridize, under the following stringent conditions (0.1×SSC, 0.1% SDS, 65° C. and washed with 2×SSC, 0.1% SDS followed by 0.1 xSSC, 0.1% SDS, 65° C.).

"Regulatory elements" refer to nucleotide sequences located upstream (5' non-coding sequences), within, or downstream (3' non-coding sequences) of a coding sequence, and which influence the transcription, RNA processing or stability, or translation of the associated coding sequence. Regulatory elements may include, but are not limited to, promoters, translation leader sequences, introns, and polyadenylation recognition sequences. Regulatory elements present on a recombinant DNA construct that is introduced into a cell can be endogenous to the cell, or they can be heterologous with respect to the cell. The terms "regulatory element" and "regulatory sequence" are used interchangeably herein.

As used herein "promoter" includes reference to a region of DNA upstream from the start of transcription and involved in recognition and binding of RNA polymerase and other proteins to initiate transcription. An "inducible" or "repressible" promoter is a promoter which is under environmental control. Examples of environmental conditions that may affect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions. In some embodiments, the promoter comprises one or more of SEQ ID NOs: 4-23. In an exemplary embodiment, the promoter sequence comprises SEQ ID NO: 6.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

As used herein, "vector" refers to a DNA or RNA molecule (such as a plasmid, linear piece of DNA, cosmid, bacteriophage, yeast artificial chromosome, or virus, among others) that carries nucleic acid sequences into a host cell. The vector or a portion of it can be inserted into the genome of the host cell.

As used herein the term "codon-optimized" refers to the modification of codons in the gene or coding regions of a nucleic acid molecule to reflect the typical codon usage of the host organism without altering the polypeptide encoded by the nucleic acid molecule. Such optimization includes replacing at least one, or more than one, or a significant number, of codons with one or more codons that are more frequently used in the genes of the host organism. A "codon-optimized sequence" refers to a sequence, which was modified from an existing coding sequence, or designed, for example, to improve translation in an expression host cell or organism of a transcript RNA molecule transcribed from the coding sequence, or to improve transcription of a coding sequence. Codon optimization includes, but is not limited to, processes including selecting codons for the coding sequence to suit the codon preference of the expression host organism. Many organisms display a bias or preference for use of particular codons to code for insertion of a particular amino acid in a growing polypeptide chain. Codon preference or codon bias, differences in codon usage between organisms, is allowed by the degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

As used herein, "transformation" refers to a process of introducing an exogenous nucleic acid molecule (e.g, a vector, a recombinant DNA molecule) into a host cell. Transformation typically achieves a genetic modification of the cell. The introduced nucleic acid may integrate into a chromosome of a cell, or may replicate autonomously. A cell that has undergone transformation, or a descendant of such a cell, is "transformed" and is a "recombinant" cell. Recombinant cells are modified cells as described herein. Cells herein may be transformed with, for example, one or more of a vector, a plasmid or a linear piece (eg., a linear piece of DNA created by linearizing a vector) of DNA. The plasmid or linear piece of DNA may or may not comprise a selectable or screenable marker. In an exemplary embodiment, the recombinant cell comprises the hpaBC genes for the biosynthesis of L-DOPA from L-tyrosine.

A nucleic acid may be introduced into a cell by conventional methods, such as, for example, electroporation (see, e.g., Heiser W. C. *Transcription Factor Protocols: Methods in Molecular Biology*™ 2000; 130: 117-134), chemical (e.g., calcium phosphate or lipid) transfection (see, e.g., Lewis W. H., et al., *Somatic Cell Genet.* 1980 May; 6(3): 333-47; Chen C., et al., *Mol Cell Biol.* 1987 August; 7(8): 2745-2752), fusion with bacterial protoplasts containing recombinant plasmids (see, e.g., Schaffner W. *Proc Natl Acad Sci USA.* 1980 April; 77(4): 2163-7), transduction, conjugation, or microinjection of purified DNA directly into the nucleus of the cell (see, e.g., Capecchi M. R. *Cell.* 1980 November; 22(2 Pt 2): 479-88).

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

In one embodiment, a method for providing a subject with a treatment for Parkinson's disease is provided. In another embodiment, methods of treating depression or anxiety and methods of improving motivation to do difficult tasks are provided. The method comprises administering to the subject in need thereof an effective amount of a composition comprising a recombinant microbial cell of the invention.

Methods of treating other disorders associated with dopamine are also contemplated. The most common disease characterized by a dopamine production deficiency is Parkinson's disease; however, invention may be readily adapted for the treatment of other diseases characterized by insufficiency of dopamine production. In one embodiment of the invention, a method of treating a disorder resulting from dopamine-related dysfunction is provided.

In one embodiment, the method of the invention is intended for treating, preventing, managing and/or delaying the progression of Parkinson's disease, restless leg syndrome, depression, stress, obesity, chronic posttraumatic stress disorder, anxiety disorders, obsessive-compulsive disorders, postpartum depression; schizophrenia, narcolepsy, manic, bipolar, and affective disorder; executive function disorders, such as attention deficit disorder (ADHD), Tourette syndrome and autism; cocaine, amphetamine, alcohol dependency, and addictive behavior, such as pathological gambling. The diseases and conditions enumerated above are given by way of example and not by way of limitation.

As used herein, the term "treating" means ameliorating, improving or remedying a disease, disorder, or symptom of a disease or condition. For example, with respect to Parkinson's disease, treatment may be measured by quantitatively or qualitatively to determine the presence/absence of the disease, or its progression or regression using, for example, symptoms associated with the disease or clinical indications associated with the pathology.

As used herein, the term "subject", "individual", or "patient" refers to any organism upon which embodiments of the invention may be used or administered, e.g., for experimental, diagnostic, prophylactic, and/or therapeutic purposes. In some embodiments, a subject is a mammal, e.g., a human or non-human primate (e.g., an ape, monkey, orangutan, or chimpanzee), a dog, cat, guinea pig, rabbit, rat, mouse, horse, cattle, or cow.

As used herein a "pharmaceutical composition" refers to a preparation of recombinant microbial cells of the invention with other components such as a pharmaceutically acceptable carrier and/or excipient.

As used herein, the term "pharmaceutically acceptable carrier" refers to any carrier, diluent, excipient, wetting agent, buffering agent, suspending agent, lubricating agent, adjuvant, vehicle, delivery system, emulsifier, disintegrant, absorbent, preservative, surfactant, colorant, flavorant, or sweetener, preferably non-toxic, that would be suitable for use in a pharmaceutical composition. The compositions of the present invention may be administered in the form of a pharmaceutical composition with a pharmaceutically acceptable carrier. Pharmaceutically acceptable carriers may be chosen to permit oral administration or administration by any other known route.

The term "excipient" refers to an inert substance added to a pharmaceutical composition to further facilitate administration of an active ingredient. Examples include, but are not limited to, calcium bicarbonate, calcium phosphate, various sugars and types of starch, cellulose derivatives, gelatin, vegetable oils, polyethylene glycols, and surfactants, including, for example, polysorbate 20.

Pharmaceutical compositions comprising a recombinant microbial cell can be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia, Pa. (2005).

In addition to the oral dosing, noted above, the compositions of the present invention may be administered by any suitable route, in the form of a pharmaceutical composition adapted to such a route, and in a dose effective for the treatment intended. The compositions may, for example, be administered parenterally, e.g., intravascularly, intraperitoneally, subcutaneously, or intramuscularly. For parenteral administration, saline solution, dextrose solution, or water may be used as a suitable carrier. In an embodiment of the invention, the therapeutic composition containing the recombinant microbial cells may be administered intrarectally. A rectal administration preferably takes place in the form of a suppository, enema, or foam.

As used herein, the terms "pharmaceutically effective" or "therapeutically effective" shall mean an amount of a composition that is sufficient to show a meaningful patient benefit, i.e., treatment, prevention, amelioration, or a decrease in the frequency of the condition or symptom being treated.

The compositions and methods described herein can be administered to a subject in need of treatment, e.g. in need of treatment for Parkinson's disease, depression, or anxiety. In some embodiments, the methods described herein comprise administering an effective amount of compositions described herein, e.g. recombinant microbial cells to a subject in order to alleviate a symptom. As used herein, "alleviating a symptom" is ameliorating any condition or symptom associated with a given condition. As compared with an equivalent untreated control, such reduction is by at least 5%, 10%, 20%, 40%, 50%, 60%, 80%, 90%, 95%, 99% or more as measured by any standard technique.

In certain embodiments, an effective dose of a composition comprising recombinant microbial cells as described herein can be administered to a patient once. In certain embodiments, an effective dose of a composition comprising recombinant microbial cells can be administered to a patient repeatedly. In some embodiments, the dose can be a daily administration, for example oral administration, of, e.g., a capsule comprising cells as described herein.

In some embodiments, the effective amount of the recombinant microbial cell is from about $10^6$ CFU to about $10^{13}$ CFU. Therefore, in some embodiments, the effective amount of the recombinant microbial cell is about $10^6$, about $10^7$, about $10^8$, about $10^9$, about $10^{10}$, about $10^{11}$, about $10^{12}$, or about $10^{13}$ CFU. In some preferred embodiments, the effective amount is about $10^9$ CFU of the recombinant microbial cell. In some embodiments, the effective amount results peak plasma levels similar to that of the standard tablet form of L-DOPA treatment. In some embodiments, the effective amount achieves stable therapeutic plasma L-DOPA concentrations of from about 300 to about 1600 ng/ml over time with the recombinant microbial cell as compared to traditional L-DOPA. Therefore, in some embodiments, the effective amount effective amount achieves stable therapeutic plasma L-DOPA concentrations of about 300 ng/ml, about 400 ng/ml, about 500 ng/ml, about 600 ng/ml, about 700 ng/ml, about 800 ng/ml, about 900 ng/ml, about 1000 ng/ml, about 1100 ng/ml, about 1200 ng/ml, about 1300 ng/ml, about 1400 ng/ml, about 1500 ng/ml, about 1600 ng/ml, or more. In some preferred embodiments, the effective amount results in peak plasma levels reaching about 1500 ng/ml. The optimal dose of the recombinant microbial cell maximizes gut colonization without inducing toxicity, including gut tissue damage, inflammation or gut microbial dysbiosis.

A composition comprising recombinant microbial cells can be administered over a period of time, such as over a 5 minute, 10 minute, 15 minute, 20 minute, or 25 minute period. The administration can be repeated, for example, on a regular basis, such as hourly for 3 hours, 6 hours, 12 hours, daily (i.e. one a day), every other day (i.e. on alternate days), or longer or such as once a week, or biweekly (i.e., every two weeks) for one month, two months, three months, four months or longer.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing, schedule can vary from once a week to daily depending on a number of clinical factors, such as the subject's sensitivity to recombinant microbial cells.

The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more.

The dosage ranges for the administration of recombinant microbial cells, according to the methods described herein depend upon, for example, the form of the cells, their potency, and the extent to which symptoms, markers, or indicators of a condition described herein are desired to be reduced, for example the percentage reduction desired. The dosage should not be so large as to cause adverse side effects. Generally, the dosage will vary with the age, condition, and sex of the patient and can be determined by one of skill in the art. The dosage can also be adjusted by the individual physician in the event of any complication.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage. A composition may be formulated such that a unit dose of the composition contains a specified number of microorganisms.

The efficacy of recombinant microbial cells in, e.g. the treatment of a condition described herein can be determined by the skilled clinician. However, a treatment is considered "effective treatment," as the term is used herein, if any one or all of the signs or symptoms of a condition described herein are altered in a beneficial manner, other clinically accepted symptoms are improved, or even ameliorated, or a desired response is induced following treatment according to the methods described herein. Efficacy can be assessed, for example, by measuring a marker, indicator, symptom, and/or the incidence of a condition treated according to the methods described herein or any other measurable parameter appropriate. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms; or (2) relieving the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein. When using an experimental animal model, efficacy of treatment is evidenced when a statistically significant change in a marker is observed.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

As used herein, the term "combination therapy" refers to the administration of the recombinant microbial cell with an at least one additional pharmaceutical or medicinal agent (e.g., an anxiolytic agent), either sequentially or simultaneously.

The methods described herein can further comprise administering a second agent and/or treatment to the subject, e.g. as part of a combinatorial therapy. In certain embodiments of the present invention, the recombinant microbial cells can be used in combination therapy with at least one other therapeutic agent.

In certain embodiments, the pharmaceutical compositions, and methods for the treatment further comprise one or more therapeutic agents for treating Parkinson's disease selected from a dopaminergic agent, such as Levodopa-carbidopa (SINEMET®, SINEMET CR®) or Levodopa-benserazide (PROLOPA®, MADOPAR®, MADOPAR HBS®); a dopaminergic and anti-cholinergic agent, such as amantadine (SYMMETRYL®, SYMADINE®); an anti-cholinergic agent, such as trihexyphenidyl (ARTANE®), benztropine (COGENTIN®), ethoproprazine (PARSITAN®), or procyclidine (KEMADRIN®); a dopamine agonist, such as apomorphine, bromocriptine (PARLODEL®), cabergoline (DOSTINEX®), lisuride (DOPERGINE®), pergolide (PERMAX®), pramipexole (MIRAPEX®), or ropinirole (REQUIP®); a MAO-B (monoamine oxidase B) inhibitor, such as selegiline or deprenyl (ATAPRYL®, CARBEX®, ELDEPRYL®); a COMT (catechol O-methyltransferase) inhibitor, such as CGP-28014, tolcapone (TASMAR®) or entacapone (COMTAN®); or other therapeutic agents, such as baclofen (LIORESAL®), domperidone (MOTILIUM®), fludrocortisone (FLORINEF®), midodrine (AMATINE®), oxybutynin (DITROPAN®), propranolol (INDERAL®, INDERAL-LA®), clonazepam (RIVOTRIL®), or yohimbine.

The other therapeutic agent can be an anti-depression agent. Useful anti-depression agents include, but are not limited to, amitriptyline, clomipramine, doxepine, imipramine, triripramine, amoxapine, desipramine, maprotiline, nortriptyline, protripyline, fluoxetine, fluvoxamine, paroxetine, setraline, venlafaxine, bupropion, nefazodone, trazodone, phenelzine, tranylcypromine and selegiline.

The other therapeutic agent can be an anxiolytic agent. Useful anxiolytic agents include, but are not limited to, benzodiazepines, such as alprazolam, chlordiazepoxide, clonazepam, clorazepate, diazepam, halazepam, lorazepam, oxazepam, and prazepam; non-benzodiazepine agents, such as buspirone; and tranquilizers, such as barbituates.

Levodopa (L-DOPA), an aromatic amino acid, is a white, crystalline compound, slightly soluble in water, with a molecular weight of 197.2. It is designated chemically as (−)-L-a-amino-b-(3,4-dihydroxybenzene)propanoic acid. Its empirical formula is $C_9H_{11}NO_4$, and its structural formula is

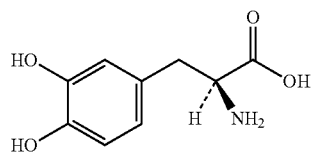 [SMILES: N[C@@H](Cc1ccc(O)c(O)c1)C(=O)O]

Current evidence indicates that symptoms of Parkinson's disease are related to depletion of dopamine in the corpus striatum. Administration of dopamine is ineffective in the treatment of Parkinson's disease apparently because it does not cross the blood-brain barrier. L-DOPA is able to cross the protective blood-brain barrier and enter the brain, where it is further converted into dopamine by the enzyme DOPA decarboxylase (DDC). Because L-DOPA can be converted into dopamine within the peripheral nervous systems, which may contribute to L-DOPA-related adverse side effects, L-DOPA is conventionally given in combination with a peripheral DDC inhibitor, such as carbidopa or benserazide to prevent its breakdown in the bloodstream, so more L-DOPA can enter the brain.

In some embodiments, the methods of the invention comprise co-administering a DOPA decarboxylase inhibitor. In certain embodiments, decarboxylase enzyme inhibitor is carbidopa, a carbidopa prodrug, benserazide, methylphenidate, or a combination thereof.

All publications, patents and patent applications identified herein are incorporated by reference, as though set forth herein in full. The invention being thus described, it will be apparent to those skilled in the art that the same may be varied in many ways without departing from the spirit and scope of the invention. Such variations are included within the scope of the following claims.

The invention is further illustrated by the following specific examples which are not intended in any way to limit the scope of the invention.

EXAMPLES

Example 1: Cloning and Characterization of L-DOPA Producing Bacteria

Several different L-DOPA biosynthesis pathways have been characterized in an attempt to build and maintain a parallel metabolism in bacteria. The commonly used fungal or plant tyrosinase pathway has previously proven effective at oxidizing L-tyrosine to L-DOPA is prone to secondary oxidation of L-DOPA to dopaquinone. Another well-characterized L-DOPA biosynthesis pathway relies on tyrosine hydroxylase. While this pathway suffers from less overoxidation, it requires a complex regeneration pathway for the essential pterin cofactor.

Figure 1:
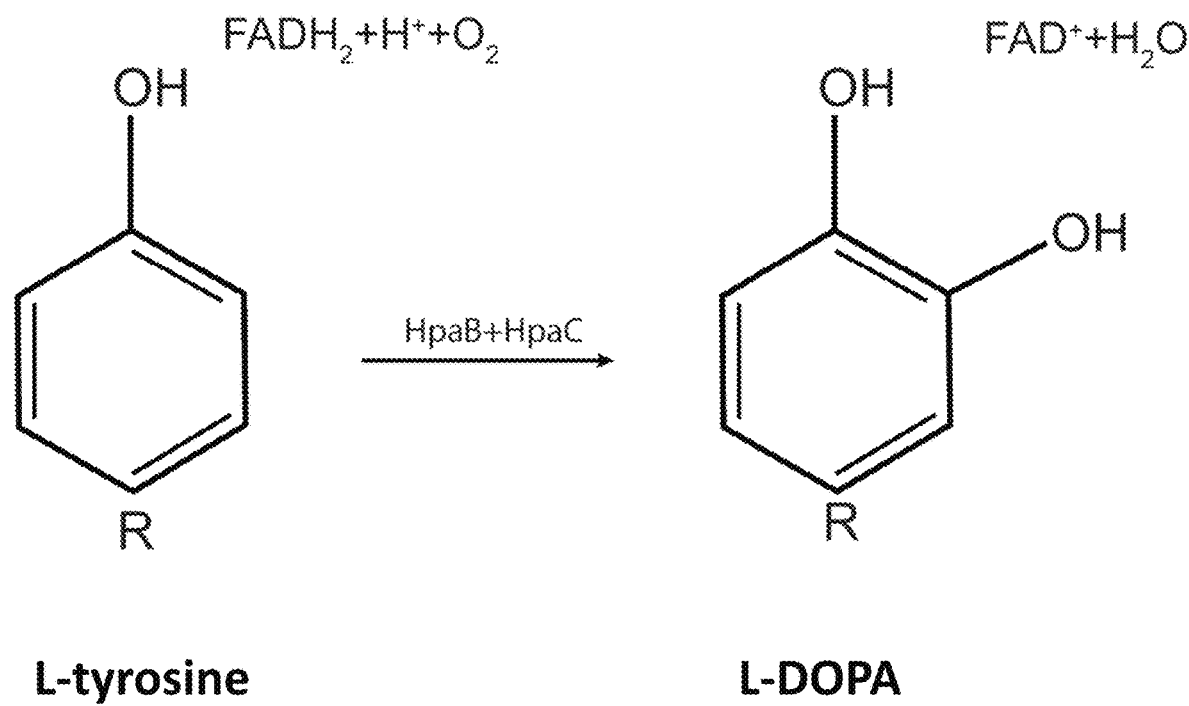
FIG. 1 depicts the biosynthesis of L-DOPA by E. coli 4-hydroxyphenylacetate 3-monooxygenase (HpaB) and its FAD reductase (HpaC).

As an alternative to these two more well characterized pathways, we investigated the biosynthesis of L-DOPA from L-tyrosine using the plasmid-based expression of E. coli hpaBC genes (FIG. 1). First, we built and validated several different L-DOPA production plasmids using the 15A, RSF1030 and broad host range RSF1010 origins of replication, and a range of common constitutive and inducible promoters ($P_{EM7}$, $P_{CP25}$ and $P_{lacUV5}$). These plasmids have been shown to produce L-DOPA, as determined by oxidation to easily observed black DOPA polymers, in several different E. coli hosts (DH10B, BL21 and OP50), as well as in Serratia species.

Figure 2A:
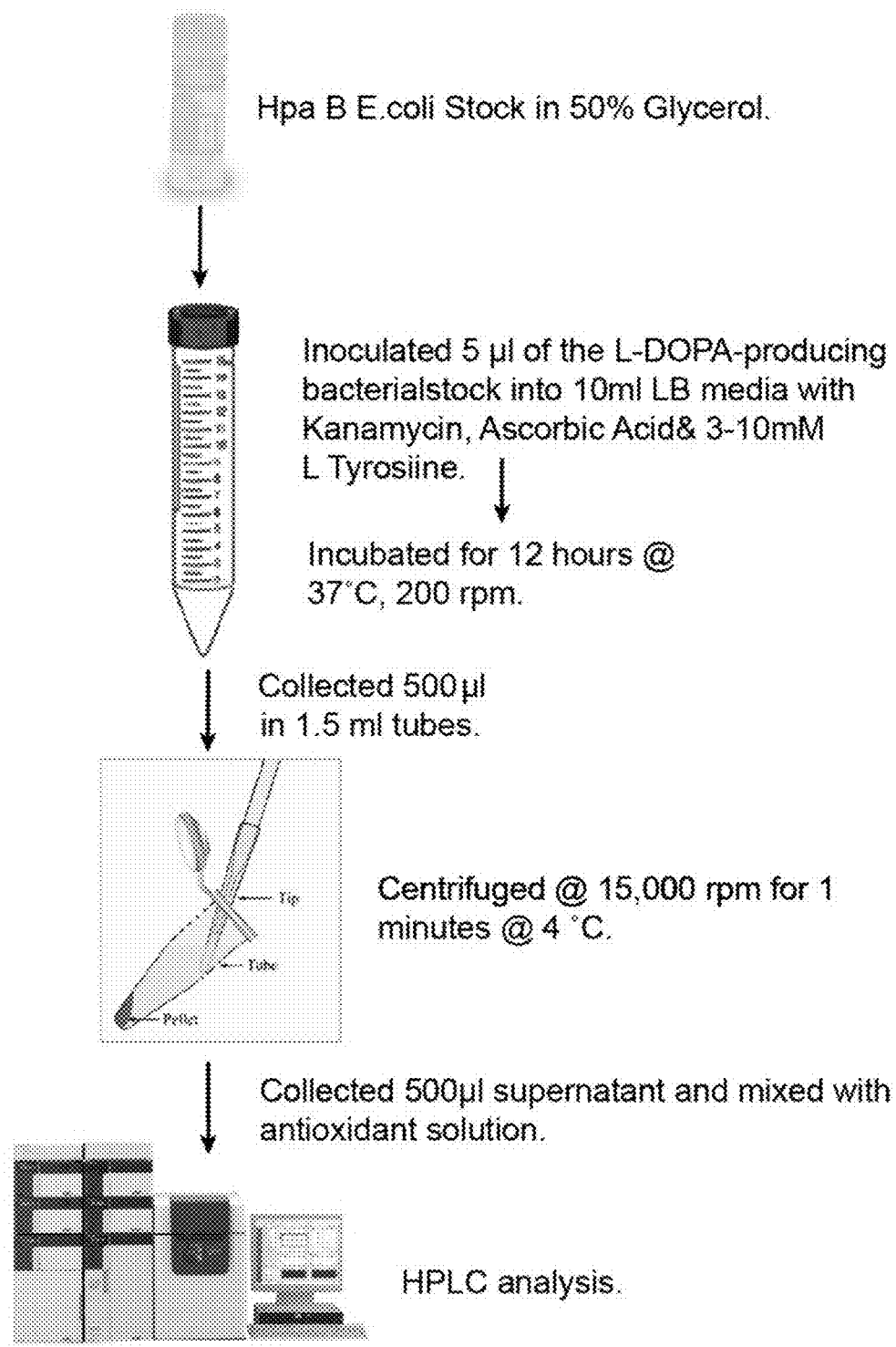
FIG. 2A shows a schematic experimental setup.
Figure 2B:
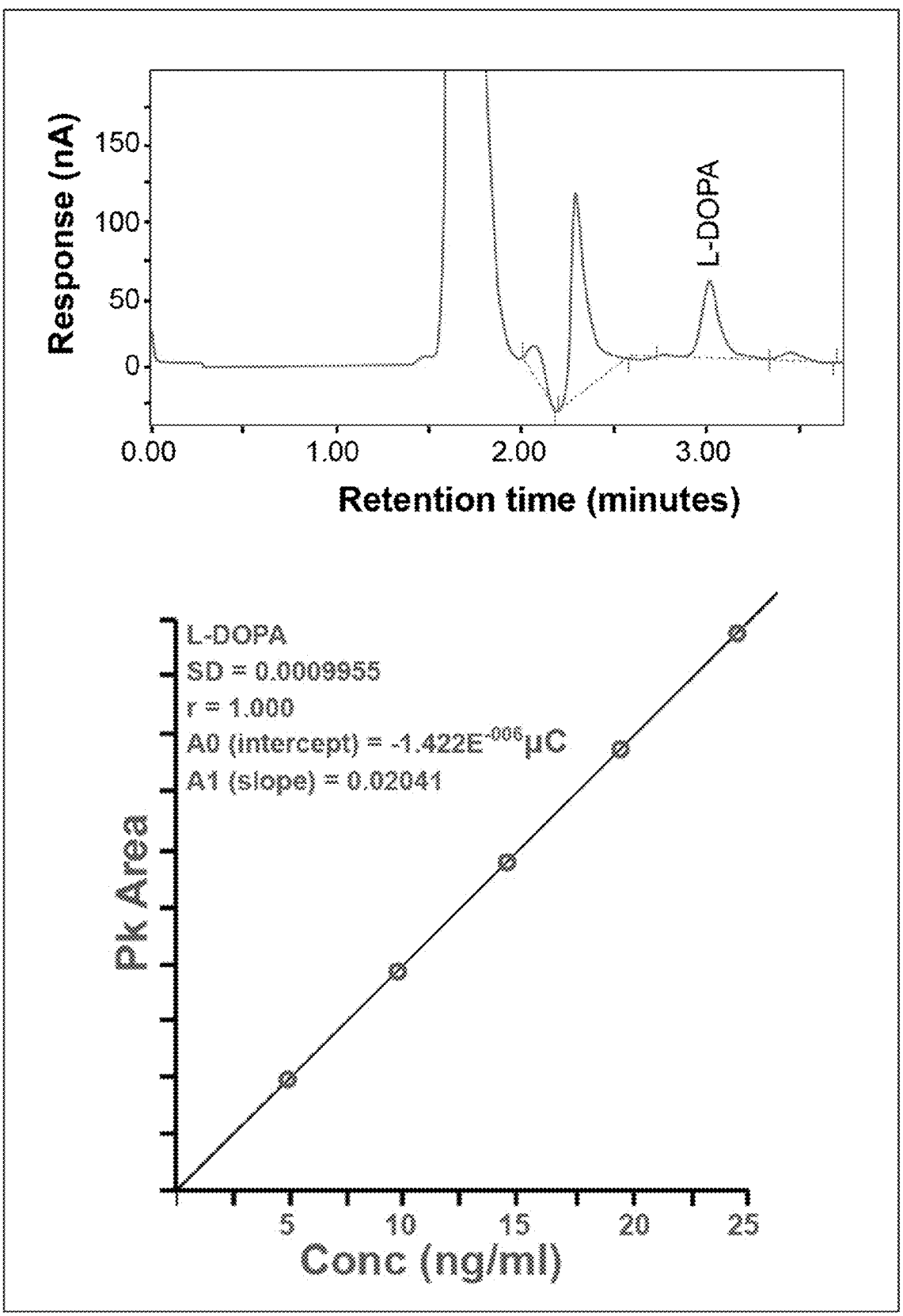
FIG. 2B shows HPLC profile and L-DOPA standard curve. Top: HPLC peak profile shows a distinct L-DOPA peak in the recombinant E. coli bacterial media identical to L-DOPA standards. Bottom: L-DOPA standard curve.
Figure 2C:
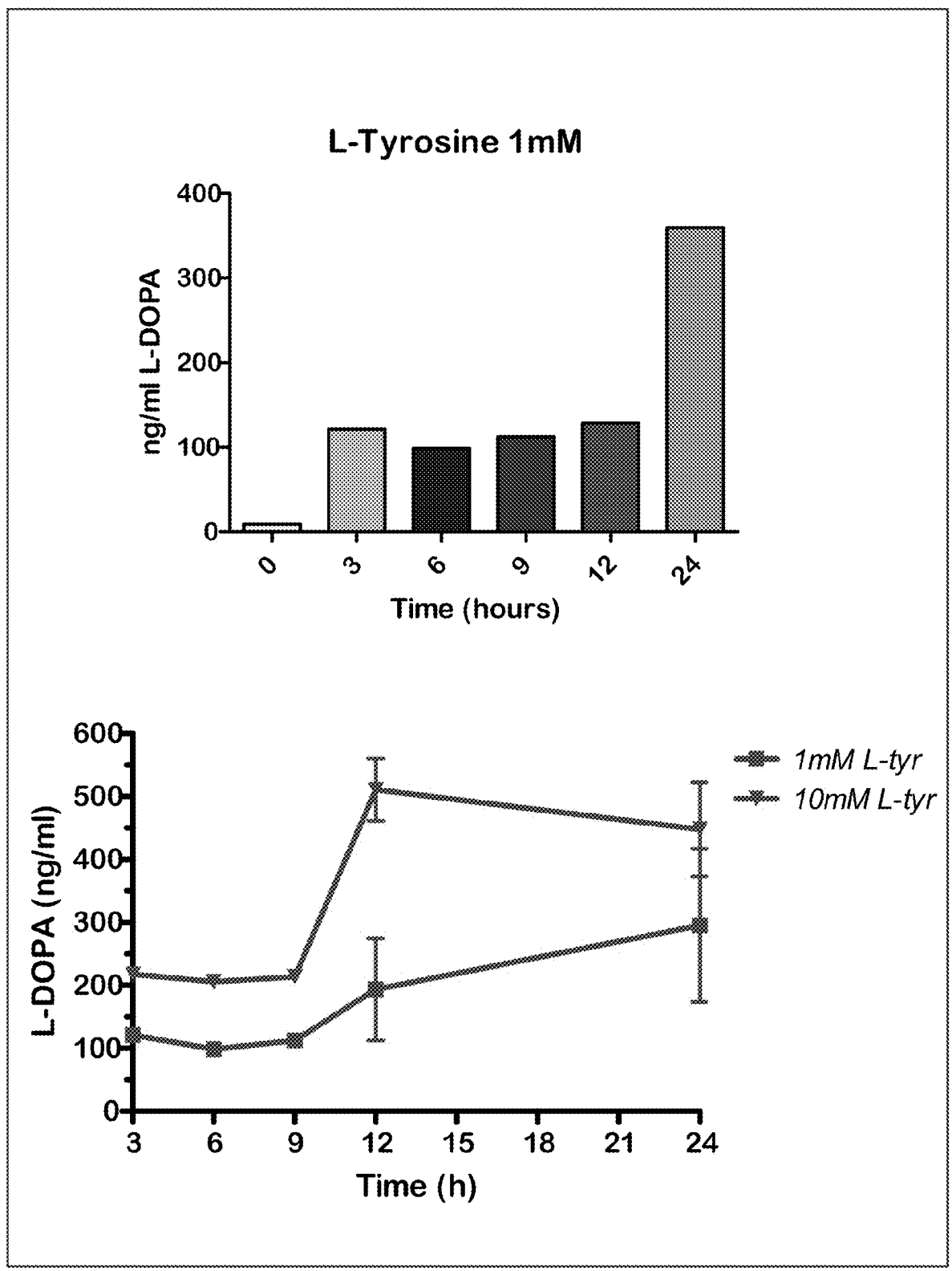
FIG. 2C shows the quantification of L-DOPA yield. L-DOPA-producing E. coli DH10B were grown in 10 ml LB medium containing kanamycin (50 µg/ml), L-tyrosine (1 mg/ml), and ascorbic acid (1-10 mg/ml) for 0-24 h at 37° C. At each time point (0, 3, 6, 9, 12 and 24 h), cultured cell suspension were obtained and cell-free broth was collected for HPLC analysis.
Figure 2D:
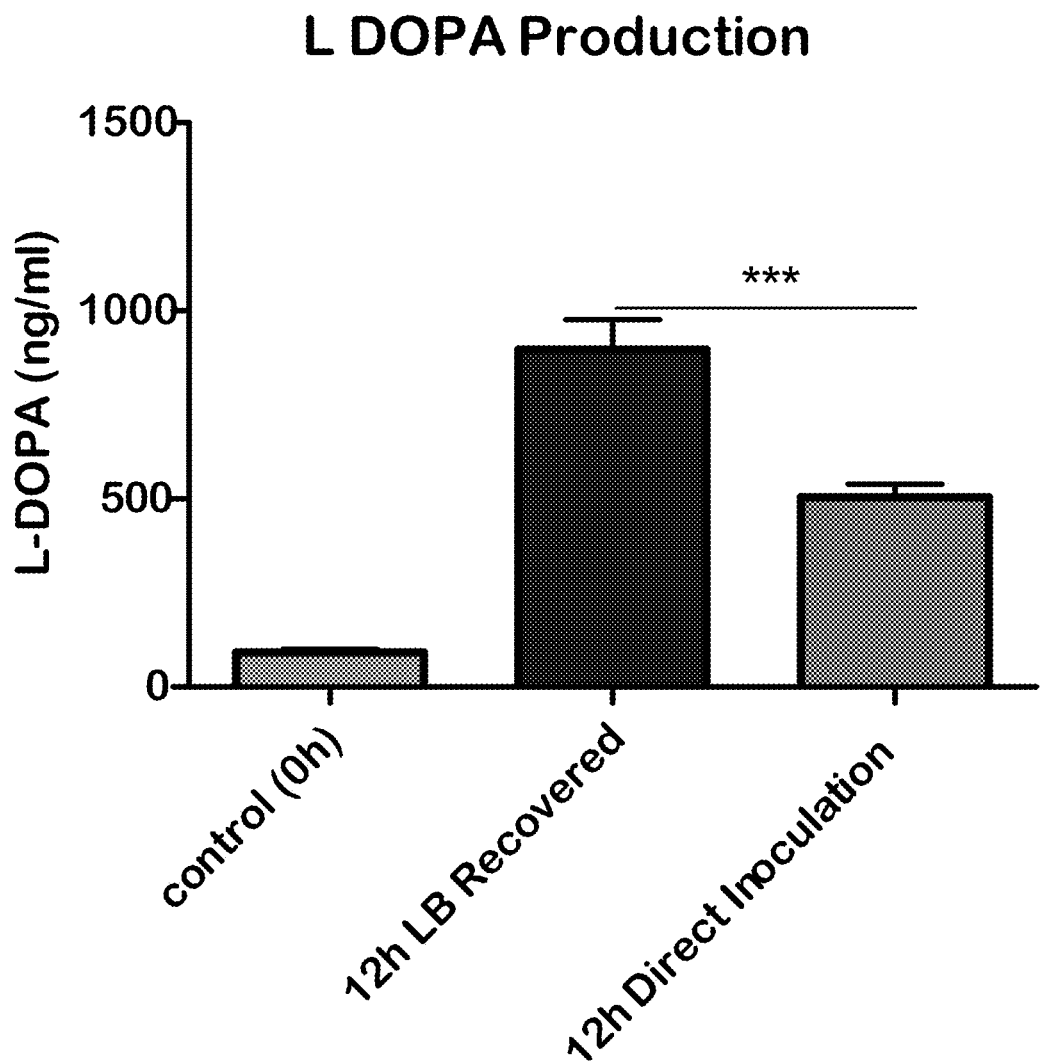
FIG. 2D shows the improvement of L-DOPA yield by allowing 12-h recovery growth form bacterial glycerol stock in LB media before inoculation into 10 mM L-tyrosine-containing LB media.

Example 2: Characterization and Quantification of Microbial L-DOPA Synthesis Via a Plasmid-Based Expression System We quantitatively assayed L-DOPA production using an internally standardized high performance liquid chromatography (HPLC) method. For this, a time-course study was performed to determine the optimal incubation time for the production of L-DOPA. A schematic representation of the experimental setup is shown in FIG. 2A. Five microliter of defrosted glycerol stock of E. coli (strain DH10B) containing the L-DOPA producing plasmid RSF 1030 were grown in 10 ml Luria-Bertani (LB) medium containing kanamycin (50 μg/ml), L-tyrosine (1 mg/ml), and ascorbic acid (1 mg/ml) present to prevent oxidation of L-DOPA for 0-24 h at 37° C. At each time point (0, 3, 6, 9, 12 and 24 h), small aliquots (0.5 ml) of cultured cell suspension were obtained and cell-free broth was then collected by centrifuge/filtration. HPLC analysis of the cell-free broth was carried out on a C18 column as previously described. As depicted in FIG. 2B, the HPLC peak profile of the 24-h grown cell-free broth showed a distinct peak at the retention time 3.01 min, which corresponded to L-DOPA standards, confirming the production of L-DOPA. Calculation of the L-DOPA yield from a L-DOPA standard curve (FIG. 2B, bottom panel) indicated that L-DOPA production started after 3 h incubation with a yield of 110 ng/ml, stayed constant over the next 9 h, but significantly increased to 350 ng/ml at the 24 h (FIG. 2C, left panel). A cell suspension without L-tyrosine was also included as a negative control, which showed no L-DOPA production. Furthermore, increasing the L-tyrosine substrate concentration to 10 mM dramatically enhanced L-DOPA production, with the highest yield of L-DOPA (528 ng/ml) achieved at 12 h incubation (FIG. 2C, right panel). HPLC data will be confirmed and correlated with small molecule mass spectrometry data. To further potentiate analysis of L-DOPA production, we recovered the *E. coli* strain from the −80° C. glycerol stock before inoculation into L-tyrosine/ascorbic acid-containing LB media. Five microliter of *E. coli* glycerol stock was recovered to grow for 12 h in 5-mL LB medium, and 5 μl of cell suspension was then subcultured for 12 h in 5-ml LB medium supplemented with kanamycin, ascorbic acid and 10 mg/ml L-tyrosine. HPLC analysis revealed that performing a recovery step significantly enhanced L-DOPA production (FIG. 2D).

Figure 2E:
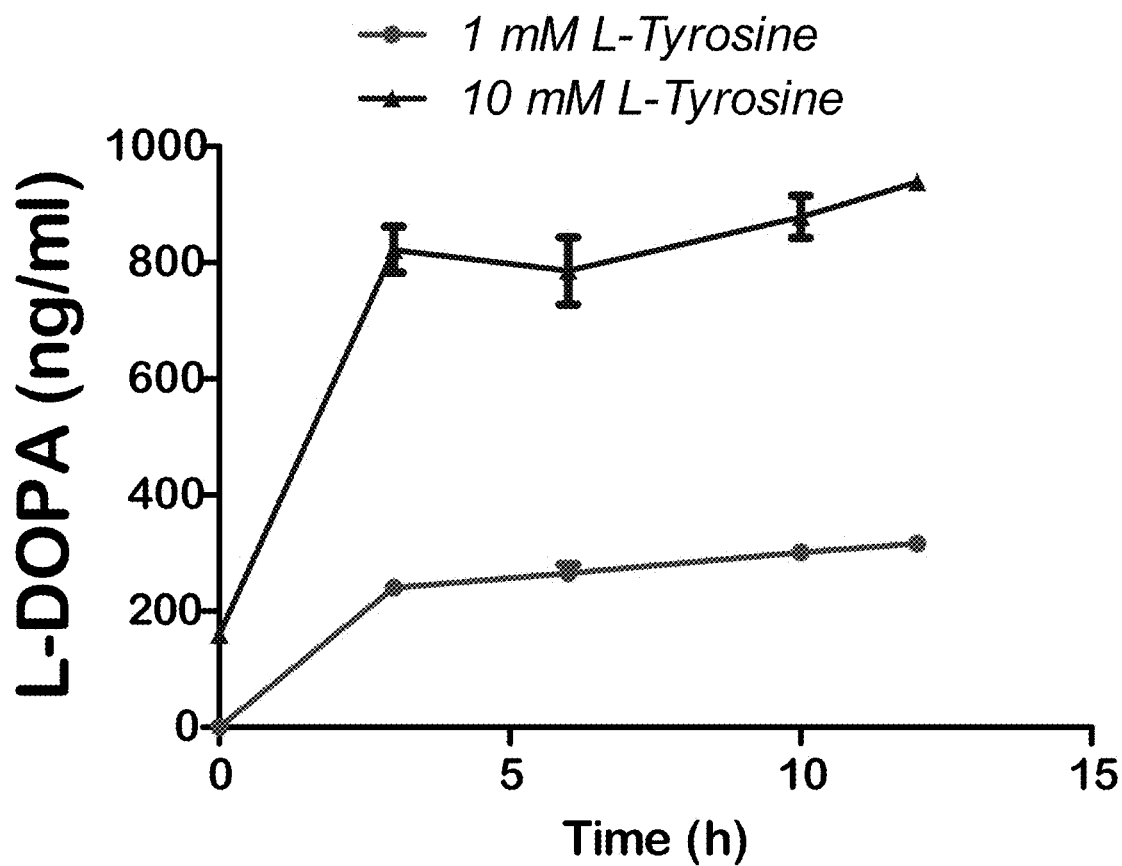
FIG. 2E shows L-DOPA production in Nissle 1917 strain. L-DOPA-producing E. coli Nissle 1917 were grown in 10 ml LB medium containing kanamycin (50 µg/ml), L-tyrosine (1-10 mg/ml), and ascorbic acid (1-10 mg/ml) for 0-12 h at 37° C. L-DOPA production was determined by HPLC.

Example 3: Transformation of hpaBC Gene into *E. coli* Nissle 1917 Strain for L-DOPA Production Since the non-pathogenic probiotic *E. coli* strain Nissle 1917 is a successful colonizer of the human gut and has shown therapeutic utility for treatment of various intestinal disorders (Grozdanov, Raasch et al. 2004), we transformed the L-DOPA-producing plasmid RSF 1030 into Nissle 1917 strain and tested its production of L-DOPA. As shown in FIG. 2E, growing this hpaBC Nissle 1917 strain in LB medium containing L-tyrosine (1-10 mg/ml) results in a rapid and similar production of L-DOPA. Collectively, these data indicate our *E. coli* DH10B and Nissle 1917 strains presents an effective source for L-DOPA production.

Example 4: *C. elegans* Model of PD

As a first test of whether microbes could generate L-DOPA in a form that would be usable by organisms, we used the L-DOPA-producing bacteria to rescue a movement defect in a worm model of PD. The *C. elegans* cat-2 mutant lacks the enzyme TH. Wild-type worms switch efficiently from swimming to crawling forms of motion when exiting a puddle. However, although the cat-2 mutant worm swims and crawls normally, it becomes transiently paralyzed as it attempts to switch from a swimming to a crawling gait. As with many animals, dopamine mediates this locomotory transition because treatment with exogenous dopamine rescues the movement defect (Vidal-Gadea et al., 2013). In our pilot studies, we found that feeding the L-DOPA producing bacteria to the cat-2 mutant enables it to move like wild-type worms. Control cat-2 mutants fed standard bacteria (OP50 strain) or standard bacteria supplemented with tyrosine showed feeble progress reflected in their tracks as they left a puddle at the center of a plate in comparison to WT. In contrast, cat-2 mutants fed the L-DOPA-producing *E. coli* strain described above and then supplemented with tyrosine displayed tracks qualitatively identical to WT. The rescue of the Parkisonian phenotype was also observed when we quantified the percent of individual worms that migrated away. These behavioral results provide strong evidence that the bacteria produce sufficient quantities of L-DOPA with specific exogenous bioactivity.

Example 5: MitoPark Mouse Model of PD

Figure 3A:
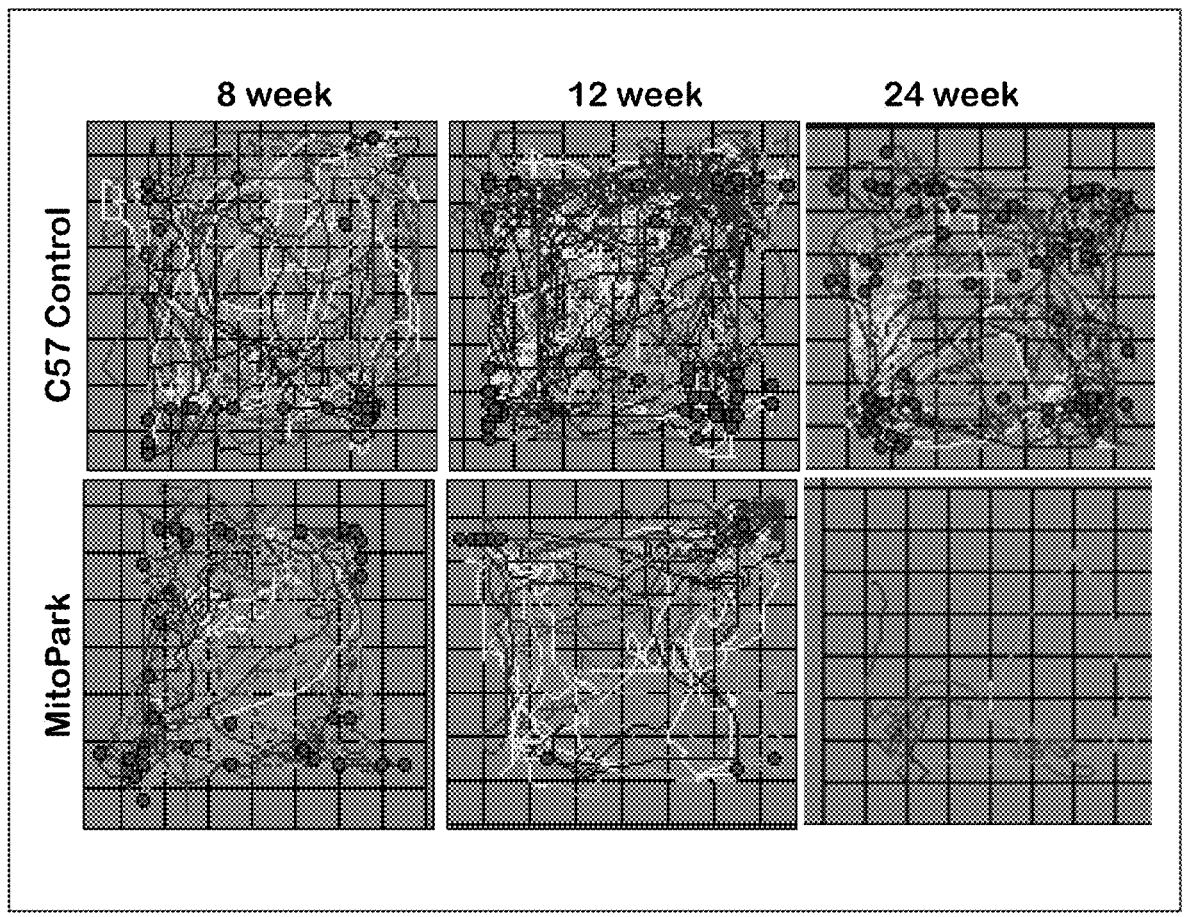
FIGS. 3A-3D show that MitoPark Parkinson's disease mice display progressive motor deficits, dopaminergic neuronal loss, and depletion of striatal dopamine.
Figure 3B:
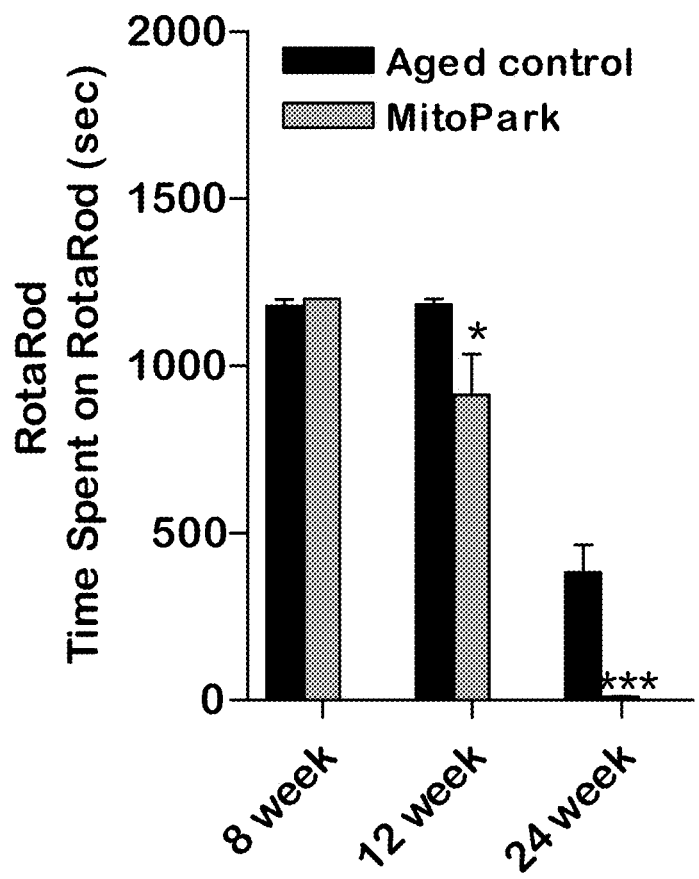
Figure 3C:
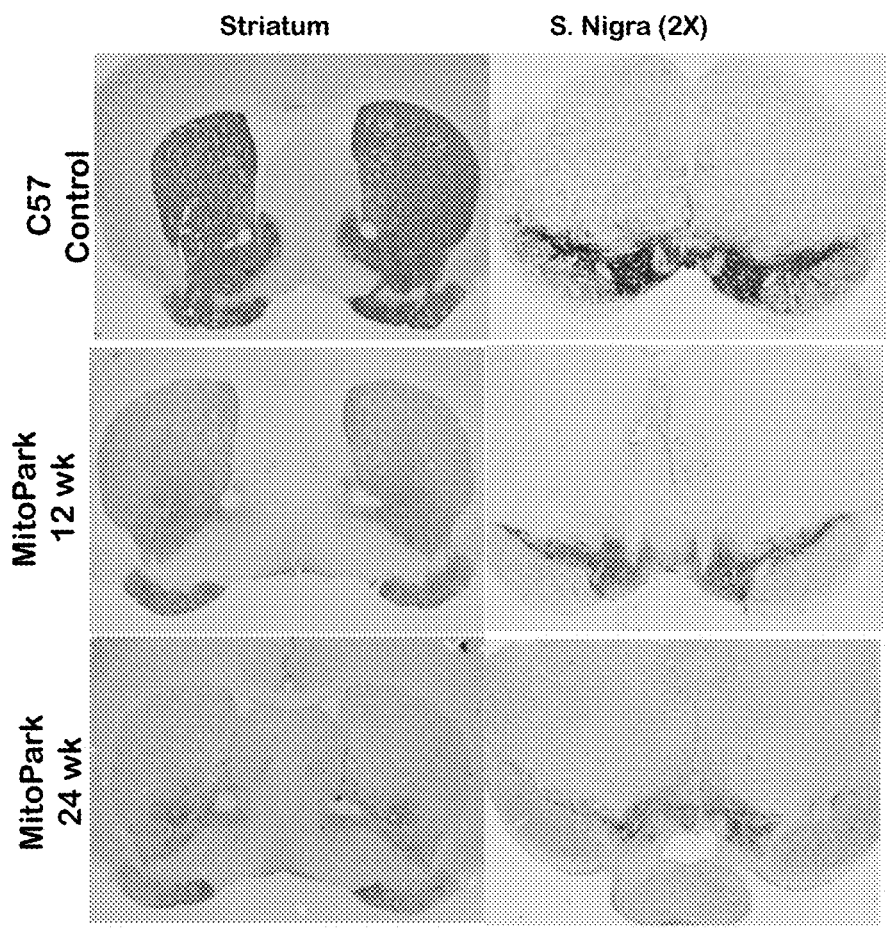
Figure 3D:
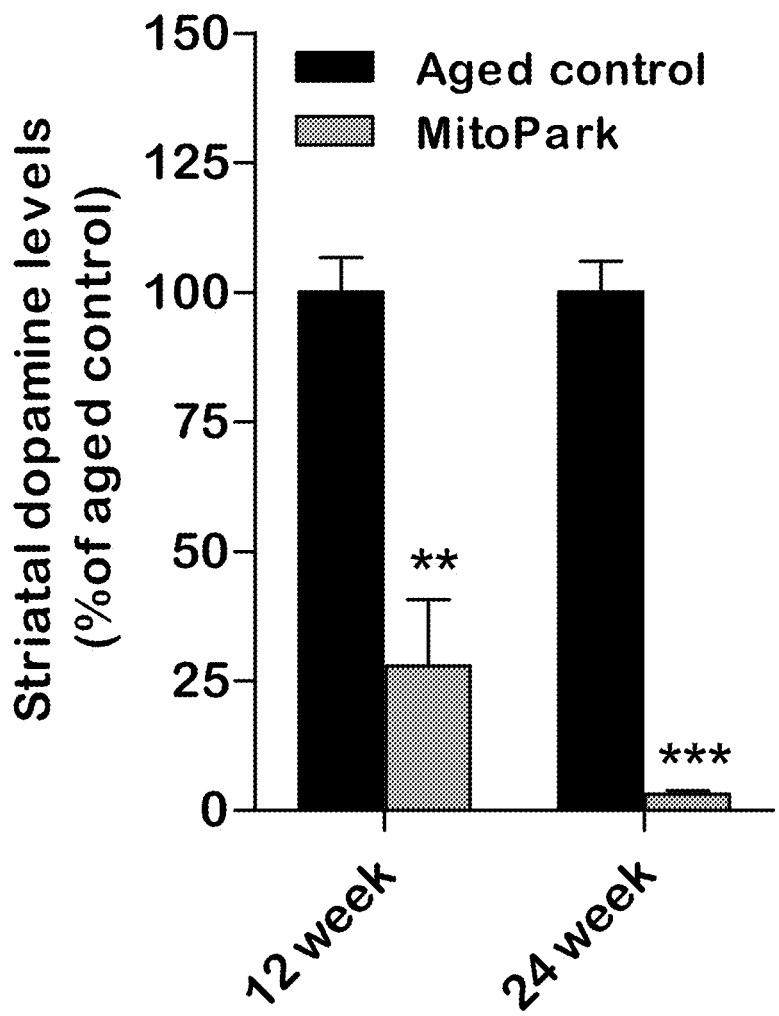
Figure 4A:
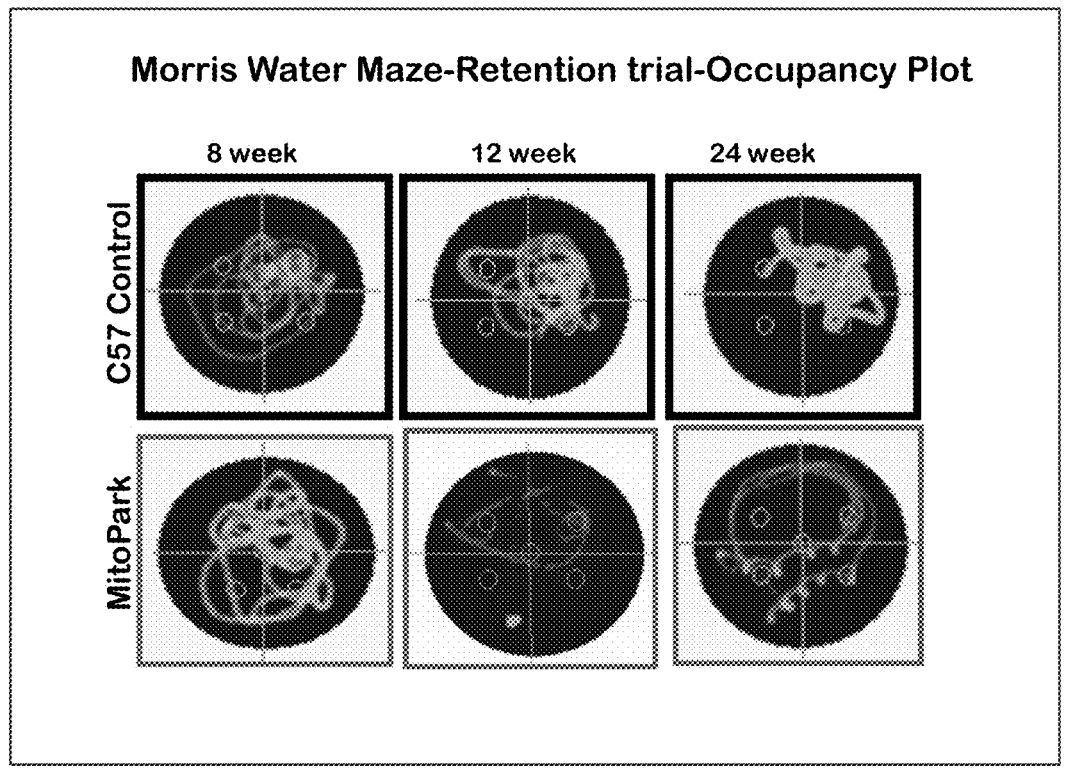
FIGS. 4A-4D show that MitoPark mice display progressive spatial learning deficits and olfactory dysfunction.
Figure 4B:
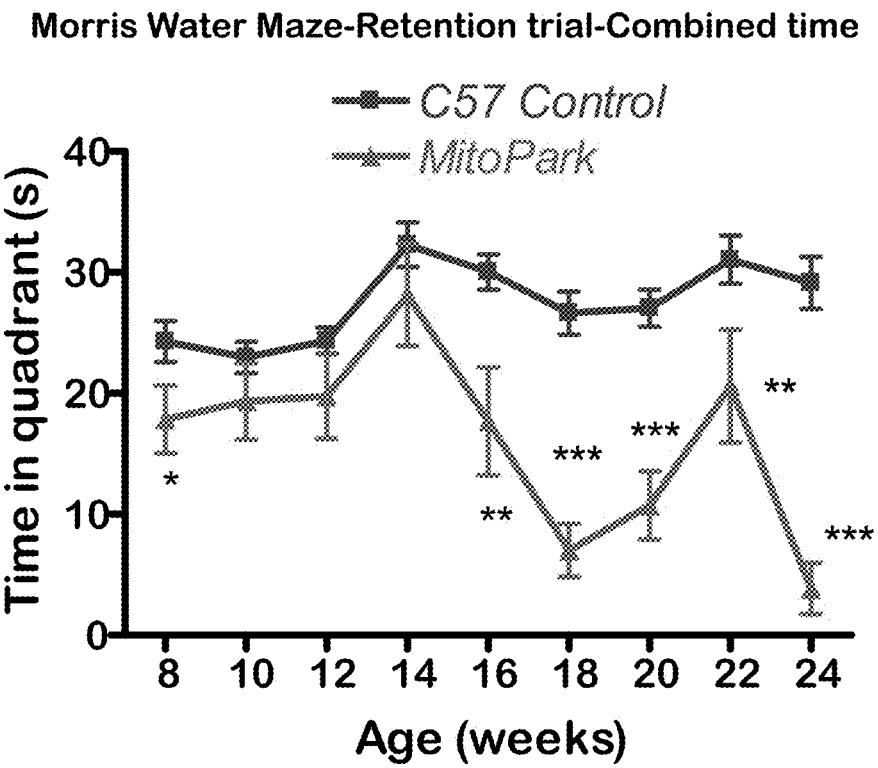
Figure 4C:
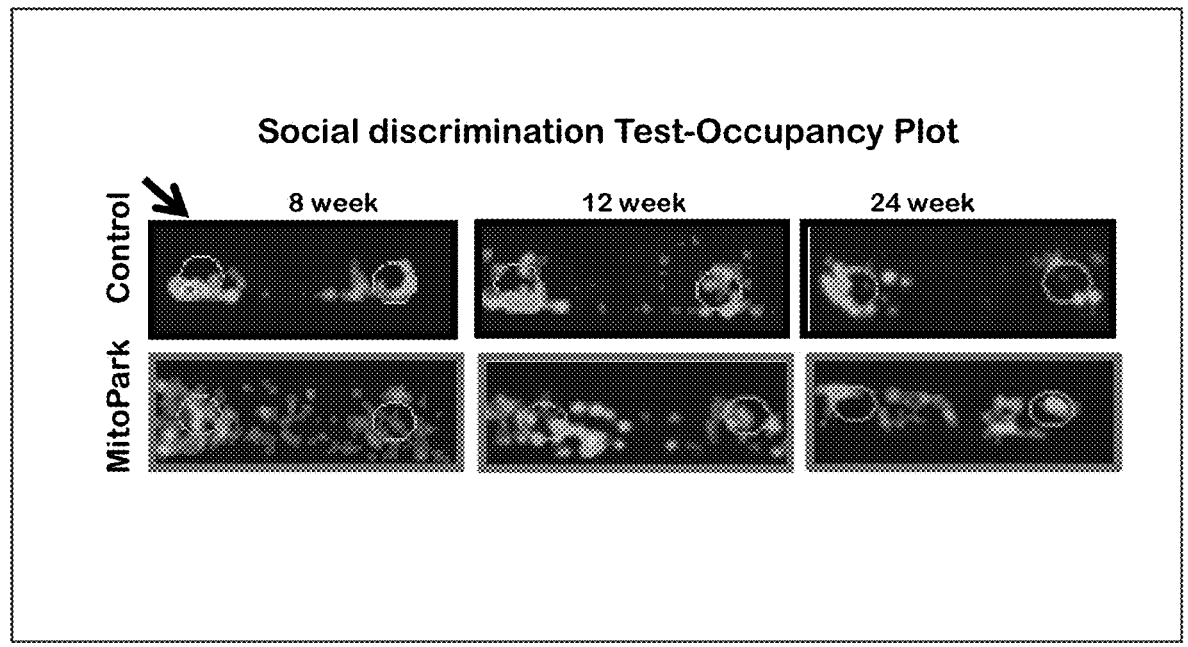
Figure 4D:
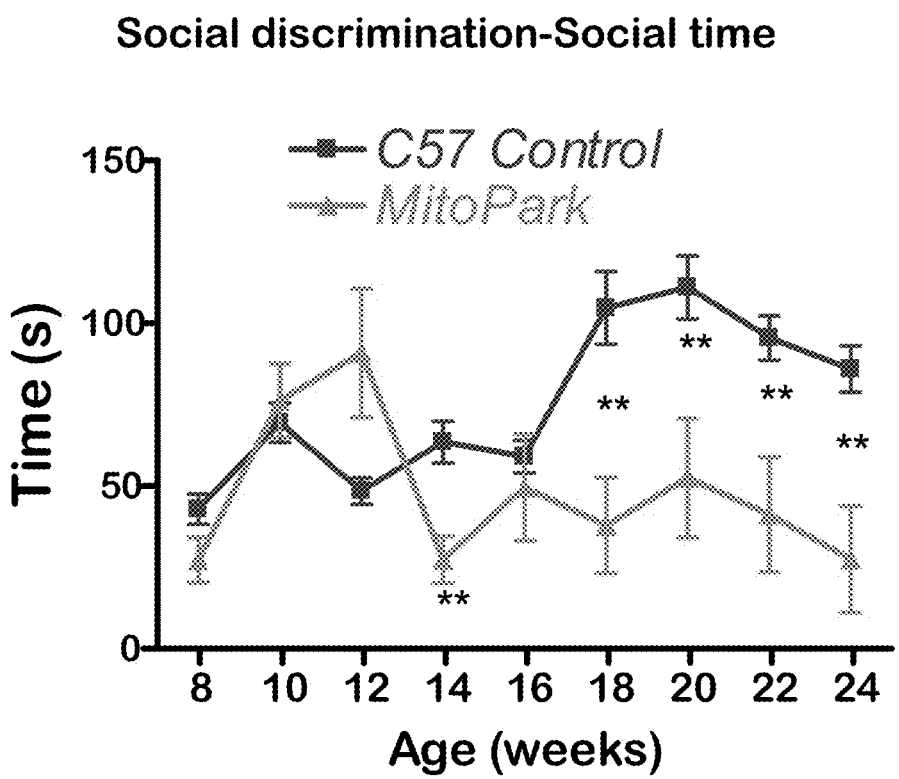
Figure 5A:
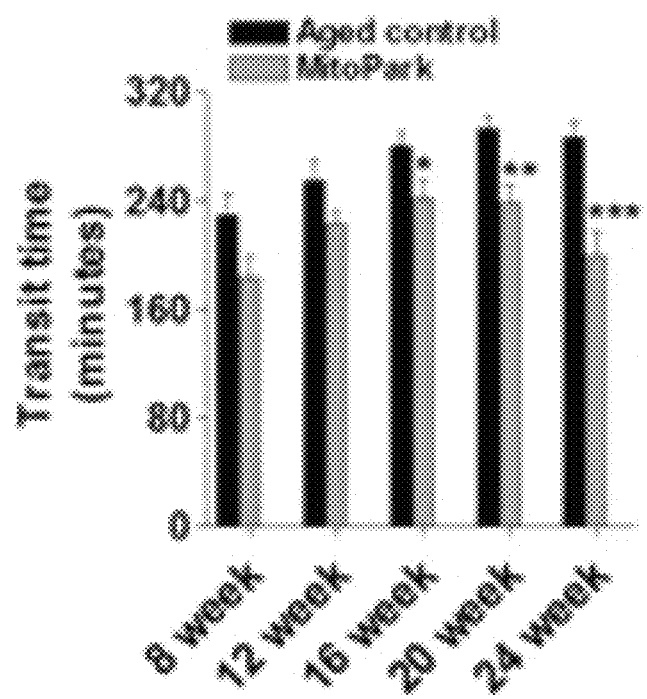
FIGS. 5A-5F show gut dysfunction in MitoPark mice.
Figure 5B:
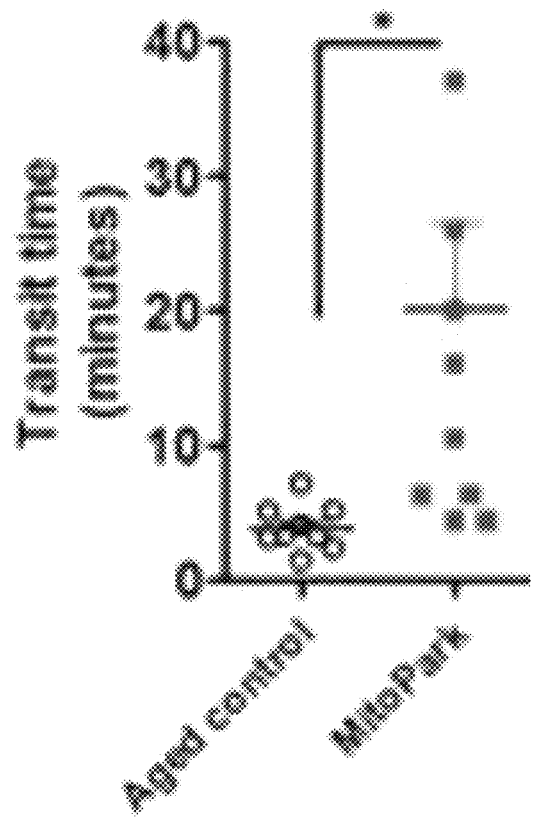
Figure 5C:
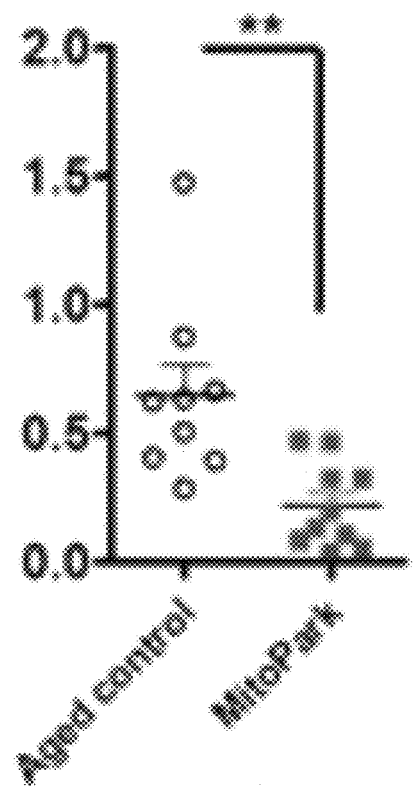
Figure 5D:
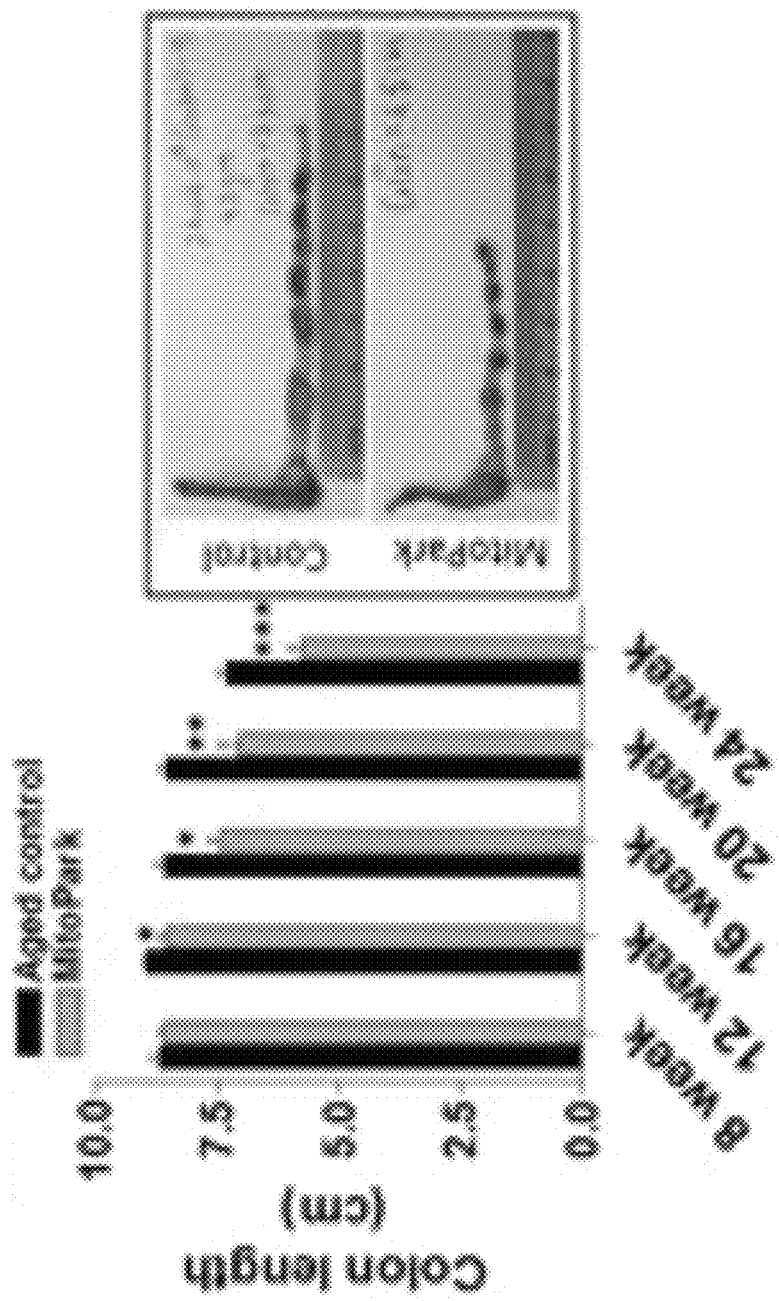
Figure 5E:
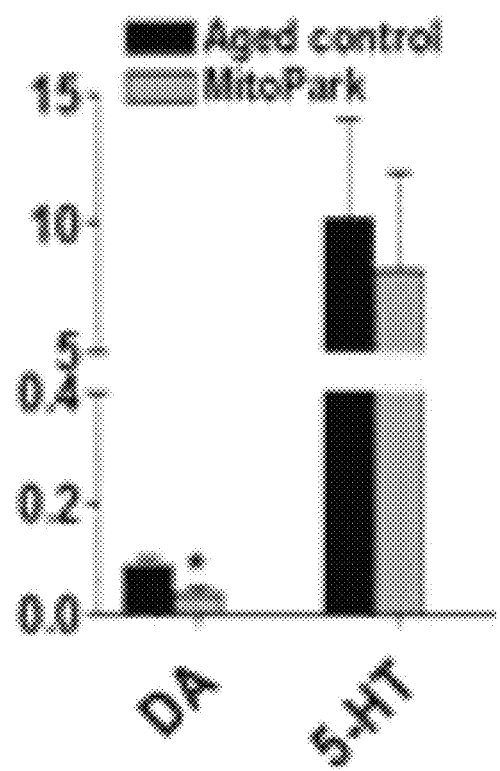
Figure 5F:
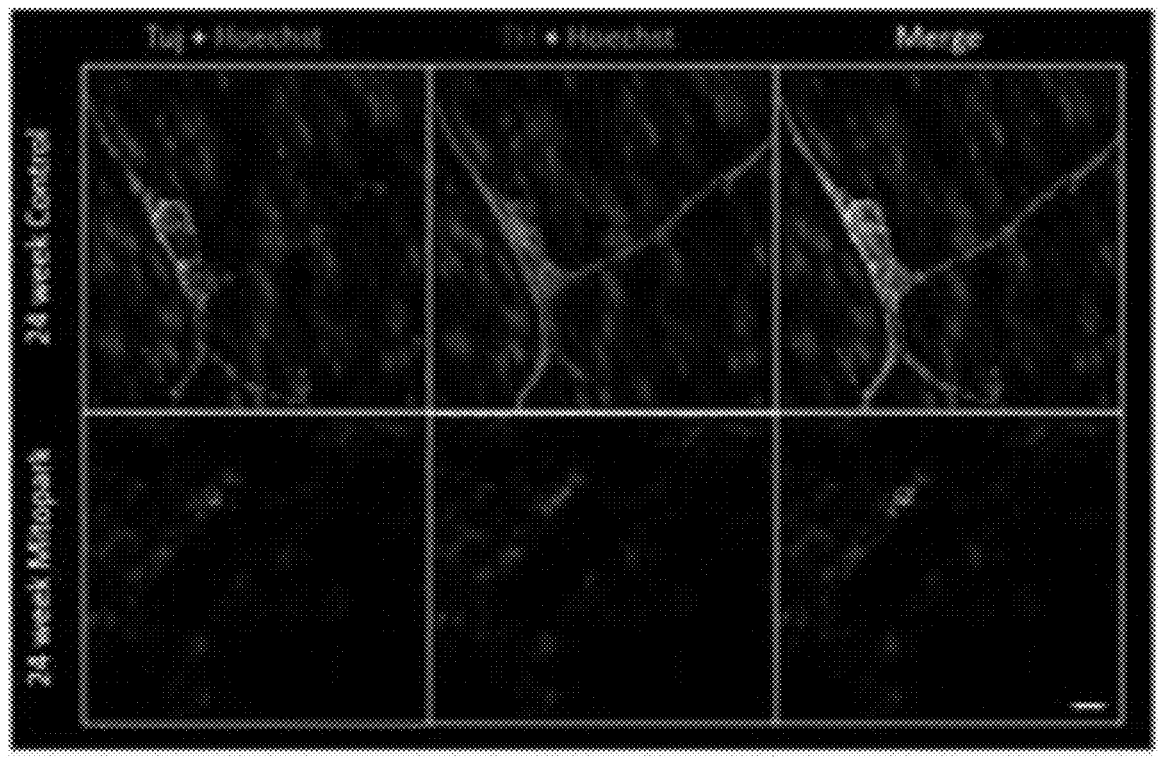

MitoPark mouse model was developed by using Cre/LoxP recombination to selectively knockout the mitochondrial transcription factor TFAM in cells expressing DAT. We currently have a breeding colony established at Iowa State University's animal facility. This model has a chronic, spontaneous, and progressive neurodegeneration accompanied by progressive motor deficits, intraneuronal inclusions, and dopamine loss. As shown in FIG. 3A-B, MitoPark motor performance at 8 weeks of age does not differ from age-matched controls. However, at 12 weeks of age, these mice displayed significantly reduced locomotor activity, and these deficits became more severe at 24 weeks of age. As previously reported, the progressive motor dysfunction is accompanied by a progressive loss of dopaminergic neurons in the substantia nigra (FIG. 3C) and a reduction of striatal dopamine (FIG. 3D). Importantly, this model is L-DOPA responsive and dyskinesia develops over time, making it an ideal pre-clinical model to test the response of microbiome-generated L-DOPA. Furthermore, recent studies showed that non-motor aspects of the PD are involved in this model. We recently confirmed that MitoPark mice display some clinically relevant nonmotor symptoms of PD, such as olfactory dysfunction (FIGS. 4A-B) and spatial learning deficits (FIG. 4C-D). Given that gastrointestinal (GI) disturbances are one of the earliest non-motor symptoms affecting most patients with PD, we evaluated GI dysfunction in this model. Curiously, from 8 weeks of age, MitoPark mice showed a lower whole gut transit time, indicating more GI motility in these mice compared to aged-matched controls (FIG. 5A). Since the motility pattern may vary from one intestinal segment to another, we further evaluated regional motility by measuring colon transit time. As shown in FIG. 5B, the MitoPark mice had increased colon transit time compared to age-matched controls. Similarly, the rate of bead movement in the distal colon was significantly decreased in the MitoPark group compared to the control group (FIG. 5C). Interestingly, we observed smaller colon lengths in MitoPark mice when compared to that of the control mice (FIG. 5D). Next, since dopamine plays an important role in modulating GI motility, we assessed intestinal dopamine content via HPLC. Reduced dopamine levels were observed in 24-week old MitoPark mice compared to age matched controls (FIG. 5E), whereas the levels of 3,4-Dihydroxyphenylacetic acid (DOPAC), homovanillic acid (HVA) and 5-HT were unchanged in these mice compared to control mice. Along with dopaminergic neurodegeneration in the mid-brain, we also observed a reduction in the number of dopaminergic neurons in the gut (FIG. 5F). All together, these preliminary data suggest the MitoPark mouse model recapitulates the chronology and development of GI dysfunction along with other motor and non-motor symptoms and can become an attractive model for pre-clinical assessment of the efficacy of microbiome-generated L-DOPA.

Example 6: Characterization of Orally Administered L-DOPA-Producing E. coli into the Gut of C57 Black Mice We used the C57 black mice for testing whether our orally administered L-DOPA-producing E. coli can colonize the gut of mice and effectively produce L-DOPA. The treatment paradigm and experimental end-points are depicted in Scheme 1.

Preparation of Fresh Inocula

L-DOPA-producing E. coli (strain: pRSF1030-hpaBC) were grown for overnight in 10 ml LB media containing kanamycin (100 µg/ml). After 12-14 h, the $OD_{600}$ was measured and the colony forming units (CFU/ml) were calculated from the standard curve. Bacterial cells were then pelleted and resuspended at $10^8$ CFU/150 µl in 1×PBS. The inocula is ready to be administered to mice.

Oral Administration of L-DOPA-Producing Bacteria into MitoPark Mice

Nine 12-week-old C57 black mice were prescreened for baseline motor activity and then randomized into 2 groups of 3 animals each. First group was received 150 µl 1×PBS daily for 7 days and sacrificed on day 8; second group received of E. coli pRSF30-hpaBC ($10^8$ CFU/150 µl 1×-PBS) daily for 7 days and sacrificed on day 8. Fecal pellets were collected daily 6 h and 24 h post-gavage. Animals were monitored for motor activity using Versamax on day 7. On day 8, animals were sacrificed, blood was collected by cardiac puncture, and striatal and gut tissues were collected and subjected to neurochemical and biochemical assessments.

Assessment of Fecal Pellets for L-DOPA-Producing Bacteria

Figure 6A:
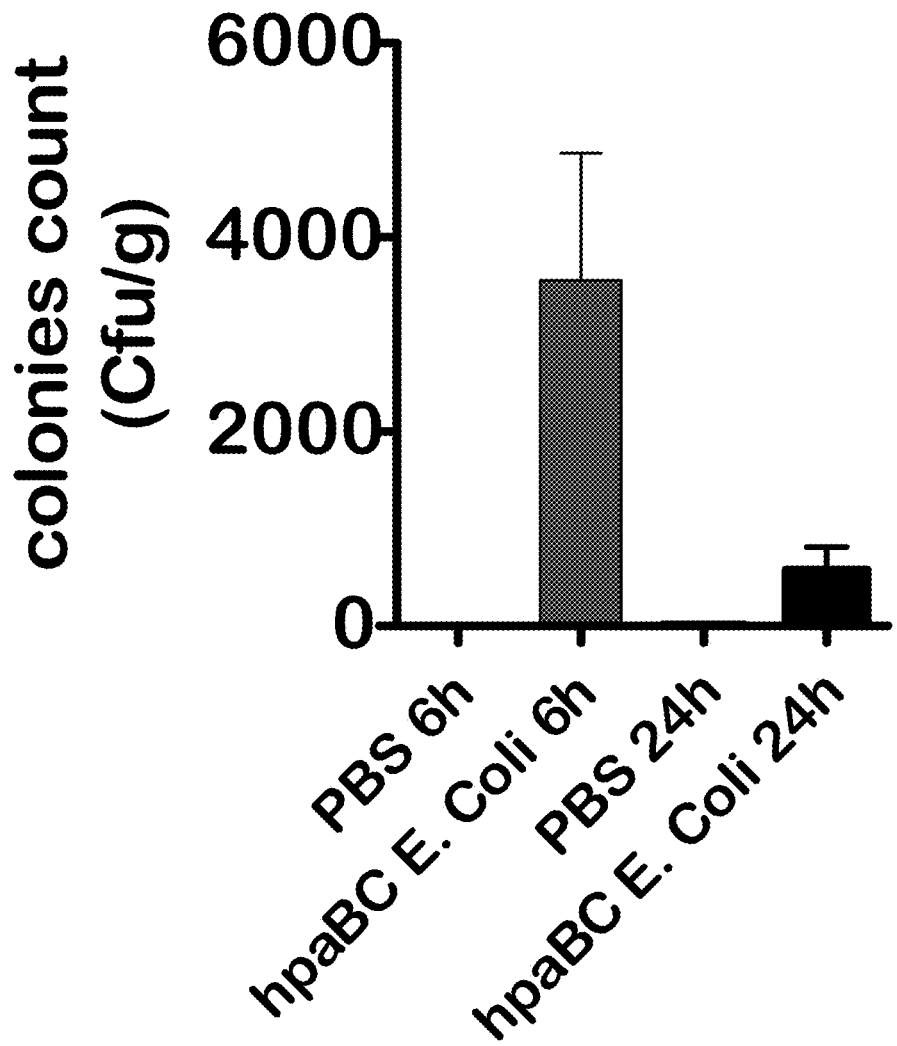
FIGS. 6A-6B show C57 black mice that orally received hpaBC E. coli or PBS daily for 7 days.

As expected, kanamycin selection on agar plates, where equal amount of fecal pellet suspension from PBS- and hpaBC E. coli-treated groups was spread, revealed that, in hpaBC E. coli-treated animals, 6 h time point pellets contained a significantly higher number of kanamycin-positive bacterial colonies as compared to 24 h time point pellets (FIG. 6A). Only minimal kanamycin-positive colonies (less than 3) were observed in the agar plates where fecal pellets from PBS control animals were plated, suggesting that our E. coli pRSF30-hpaBC strain was successfully colonized in the gut of mice.

Assessment of Kanamycin Positive Bacterial Colonies for the Presence of hpaBC Gene and L-DOPA Production Next, we isolated 3 kanamycin-positive bacterial colonies from agar plates spread with 6 h and 24 h fecal pellet suspension of each mouse and then grew them in 10 ml of LB media containing kanamycin (100 µg/ml), L-tyrosine (10 mg/ml), and ascorbic acid (1 mg/ml) for 12 h.

qPCR 5 ml of the cell medium were centrifuged, DNA was isolated from bacterial pellets and qPCR was performed using the primers specific for hpaBC gene.

Figure 6B:
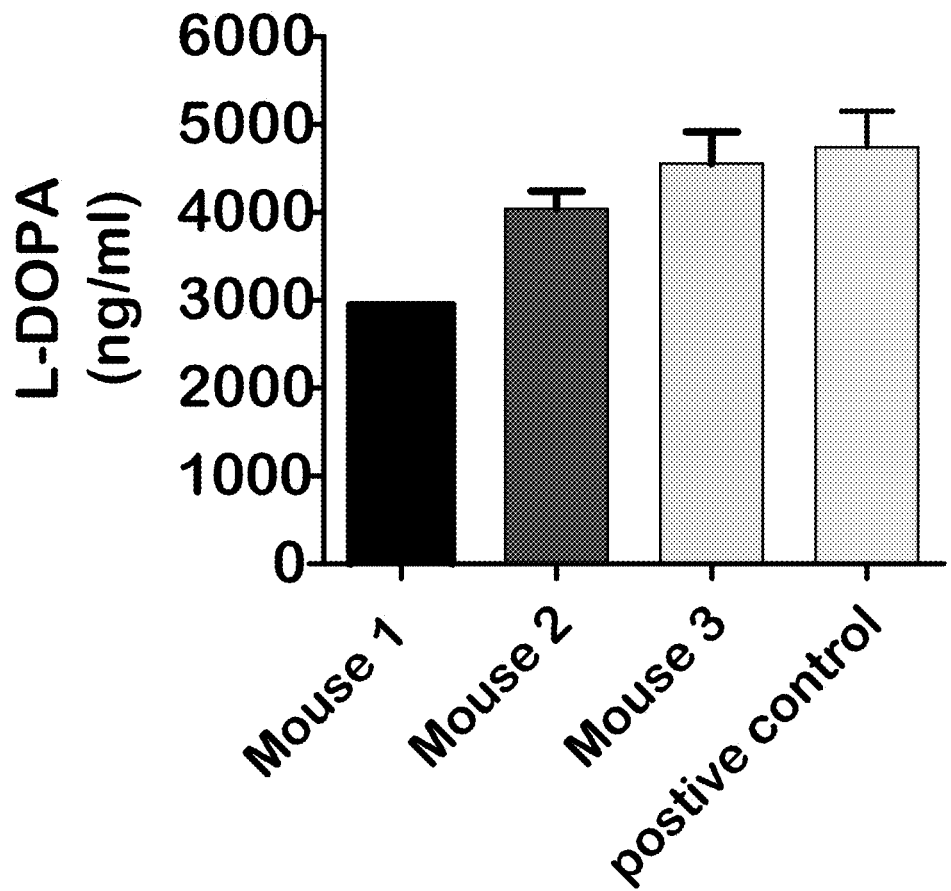

As shown in FIG. 6B, kanamycin-positive colonies isolated from fecal pellets of hpaBC E. coli-treated group showed significant amplification of the hpaBC gene, suggesting that the kanamycin-positive colonies from hpaBC E. coli-treated animals indeed contain hpaBC gene coding for the enzyme that produces L-DOPA. The colonies picked from PBS control animals failed to grow in LB-kanamycin media. HPLC: 500 µl of LB-media containing bacteria were centrifuged, then both media and bacterial pellets were processed for HPLC quantification of L-DOPA as described above. As shown in FIG. 6C, bacterial pellets and media from hpaBC E. coli-treated animals showed high amounts of L-DOPA production (range: 98.34-161 ng/ml).

Behavioral Assessment

Figure 7A:
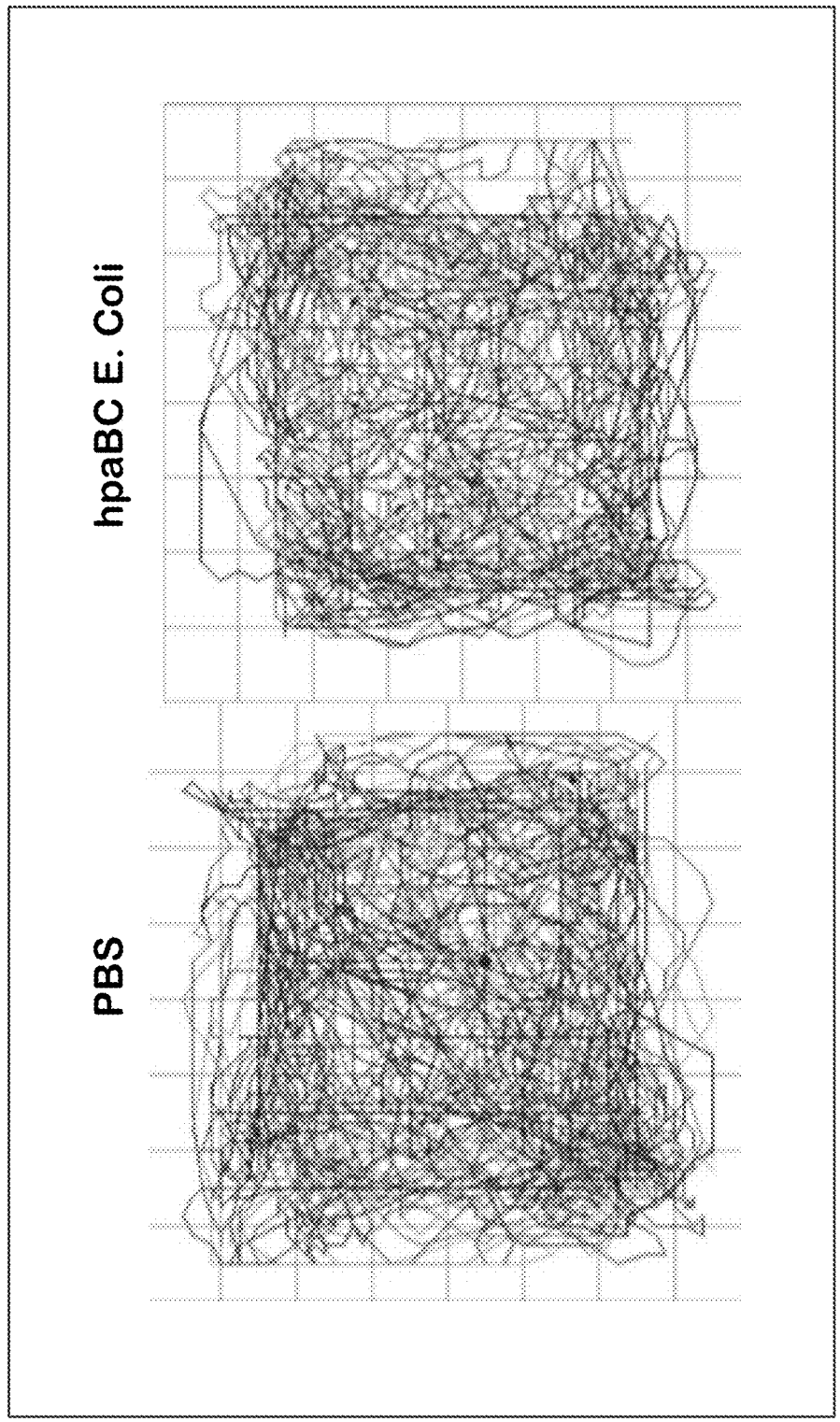
FIGS. 7A-7D show C57 black mice that orally received hpaBC E. coli or PBS daily for 7 days. Before sacrifice, mice were tested for locomotor activities.
Figure 7B:
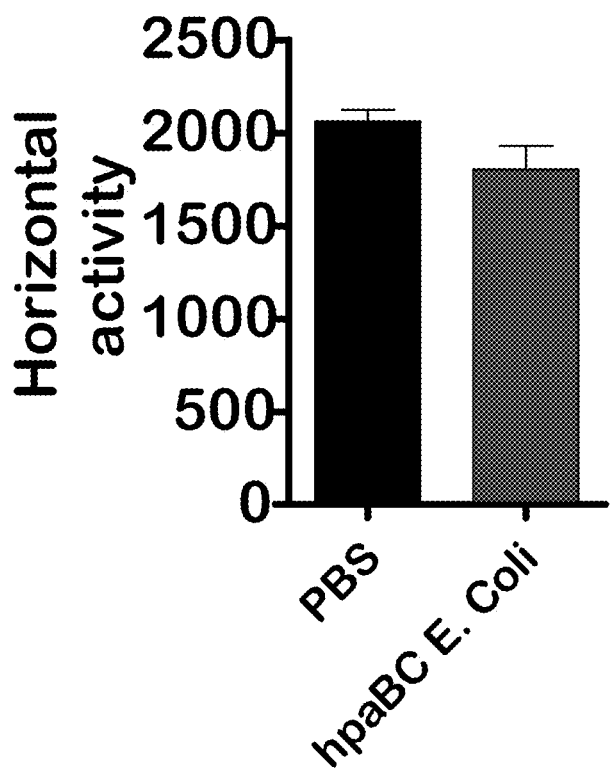
Figure 7C:
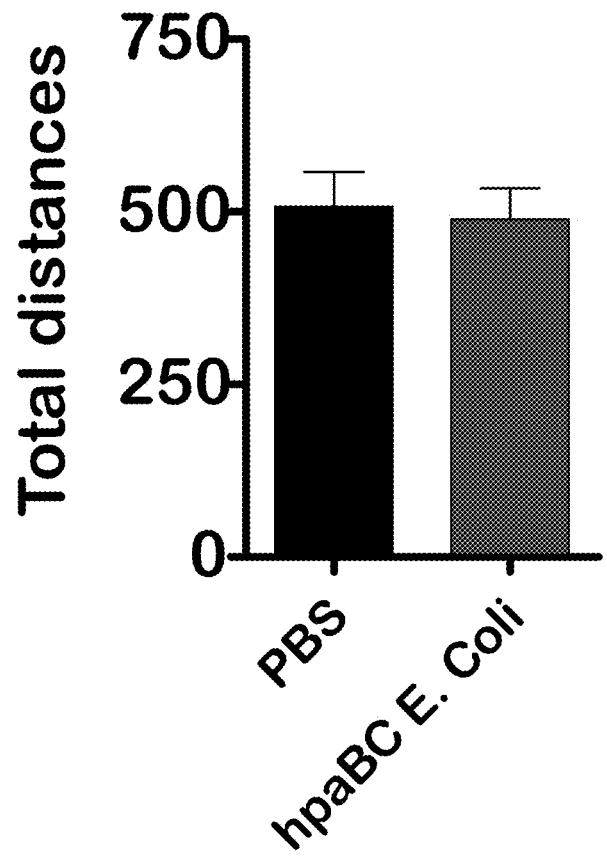

Behavioral analysis using Versamax computerized monitor activity system revealed that oral administration of L-DOPA-producing bacteria up to 7 days did not have any adverse effects on moving paths, horizontal activity and total distances (FIG. 7A-C).

Plasma L-DOPA Levels

Figure 7D:
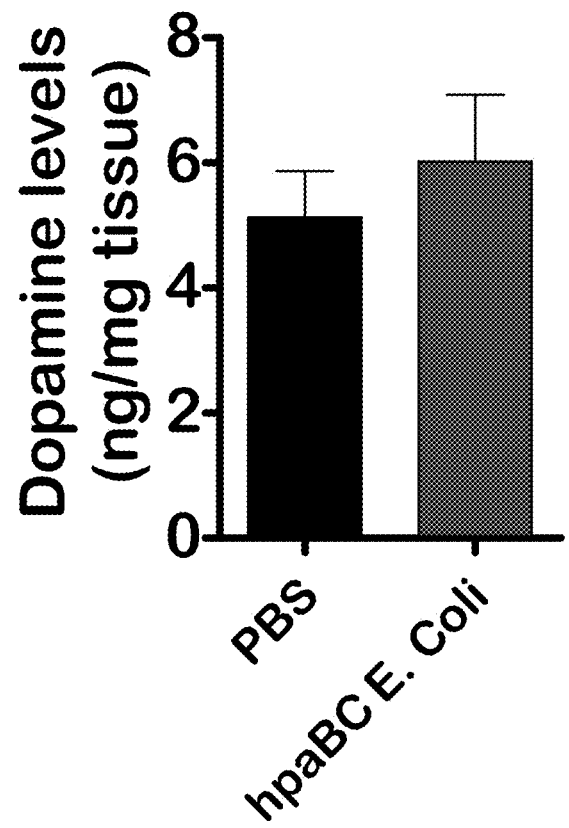

As shown in FIG. 7D, the plasma collected from hpaBC E. coli-treated animals contained significantly higher levels of L-DOPA as compared to that from PBS control animals.

Striatal Dopamine Levels

Dopamine levels in the striatal tissues were increased by at least 50% in mice orally administered with L-DOPA-producing bacteria for 7 days as compared to PBS administered animals, suggesting that microbially delivered L-DOPA is able to cross BBB and is further converted to dopamine (FIG. 7E).

Serum Chemistry Profiling

Results revealed that orally administered E. coli pRSF30-hpaBC bacteria to C57 black mice did not alter serum chemistry profiling, suggesting the safety of using this bacteria for therapeutic purposes (Table 1).

TABLE 1

Blood chemistry analysis results

| Treatment Paradigm | PBS-treated | Ec-LD-treated |
|---|---|---|
| Albumin (Abaxis) | 3 | 3.3 |
| Alk Phos (Abaxis) | 5 | 5 |
| ALT (Abaxis) | 42 | 53 |
| Amylase | 587 | 591 |
| T. Bilirubin (Abaxis) | 0.25 | 0.2 |
| BUN (Abaxis) | 10 | 12 |
| Calcium (Abaxis) | 4 | 4 |
| Creatinine (Abaxis) | 0.25 | 0.3 |
| Glucose (Abaxis) | 190.5 | 190 |
| Sodium (Abaxis) | 151 | 148 |
| Potassium - Abaxis | 8.2 | 2.9 |
| T. Protein (Abaxis) | 3.5 | 3.4 |
| Hemolytic Index (Ab) | 2.5 | 3 |
| Lipemic Index (Abaxis) | 1 | 0 |
| Icteric Index (Abaxis) | 0 | 0 |

Together, these results suggest the orally administered E. coli pRSF30-hpaBC bacteria into the gut of C57 black mice successfully colonize in the GI-tract. Further, L-DOPA that is produced in the gut crosses the intestinal barrier and goes to the blood. Once in the blood, the L-DOPA travels to brain and gets converted to dopamine, resulting in increased striatal dopamine levels. Behavioral assessment and serum chemistry analysis revealed that microbially delivered L-DOPA does not cause any change in behavior or serum chemistry, suggesting it is non-toxic and safe.

Example 7: E. coli Nissle 1917 L-DOPA-Producing Bacteria ($EcN^1_{L-DOPA}$) Successfully Colonize the Gut of Mouse Model As described in FIG. 2E, E. coli Nissle 1917 L-DOPA-producing bacteria ($EcN^1_{L-DOPA}$) were generated by transforming plasmid pRSF1030, which contains the hpaBC gene coding for L-DOPA synthesizing enzymes. We also generated an empty vector strain of E. coli Nissle 1917 by transforming the pRSF plasmid/vector alone for use as a negative control. This vector control will be referred to as $EcN_{Vec}$.

Figure 8:
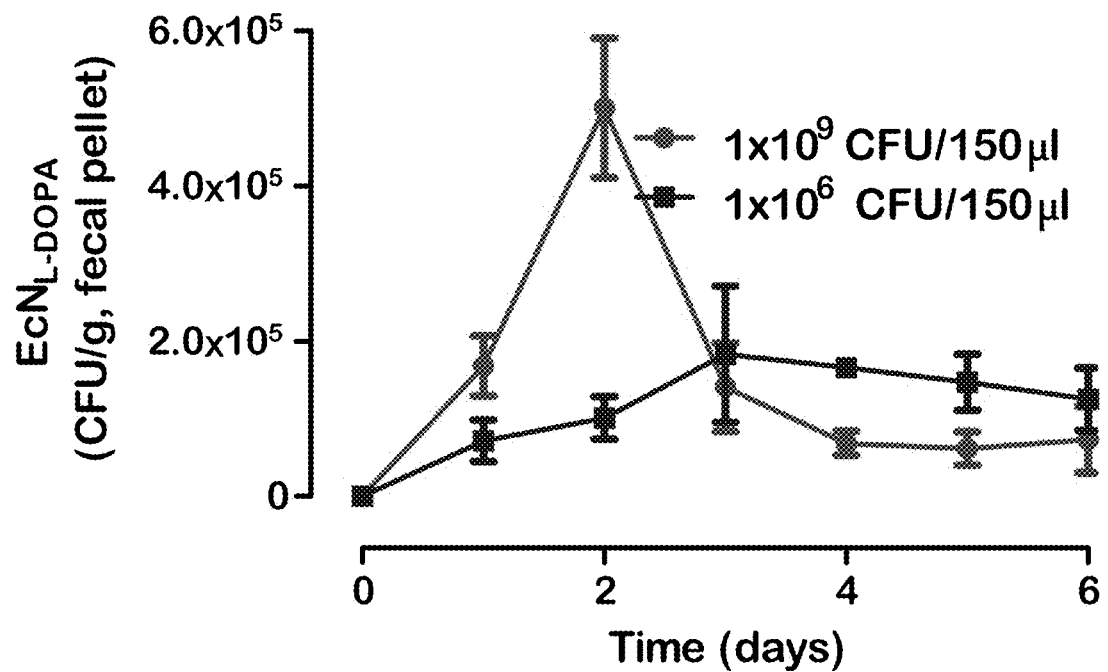
FIG. 8 shows E. coli Nissle 1917 L-DOPA-producing bacteria ($EcN^1_{L\text{-}DOPA}$) successfully colonizes the gut of PD mouse model. Fifteen to seventeen week old C57BL/6 mice received single oral administration of $EcN^1_{L\text{-}DOPA}$ and were co-treated with the decarboxylase inhibitor benserazide. Fecal pellets were collected and kanamycin-resistant colonies were counted and plotted as CFU/g of fecal pellet.

Twelve- to 14-week-old male and female C57BL/6 mice (n=6) were administered a single oral gavage of $10^6$ or $10^9$ CFU/150 µl of $EcN^1_{L-DOPA}$ containing L-Tyrosine (100 mg/kg) plus a single i.p. injection of benserazide (12.5 mg/kg), an L-amino acid decarboxylase inhibitor. Fecal pellets were collected prior to treatment to establish baseline measurements and then daily for six days post-treatment. Fecal pellets were homogenized with a bullet blender and plated in triplicates onto LB agar plates containing kanamycin (50 ug/ml). Kanamycin-resistant colonies representing the $EcN^1_{L-DOPA}$ Nissle 1917 strain were counted and plotted as CFU/g of fecal pellet. Colonization of $EcN^1_{L-DOPA}$ at both doses of $10^6$ and $10^9$ CFU/150 µl occurs in a time- and dose-dependent manner, peaking in 2-3 days, and then slowly decreases closer to baseline levels over a period of six days (FIG. 8). Kanamycin-resistant colonies peaked 2 days after administering $10^9$ CFU/150 µl $EcN^1_{L-DOPA}$ at $0.5 \times 10^6$ CFU/g of fecal pellet, whereas it peaked 3 days after administering $10^6$ CFU/150 µl $EcN^1_{L-DOPA}$ at $0.18 \times 10^6$ CFU/g of fecal pellet. Based on these results, we used $EcN^1_{L-DOPA}$ at a dose of $10^9$ CFU/150 µl for subsequent efficacy studies.

Figure 9A:
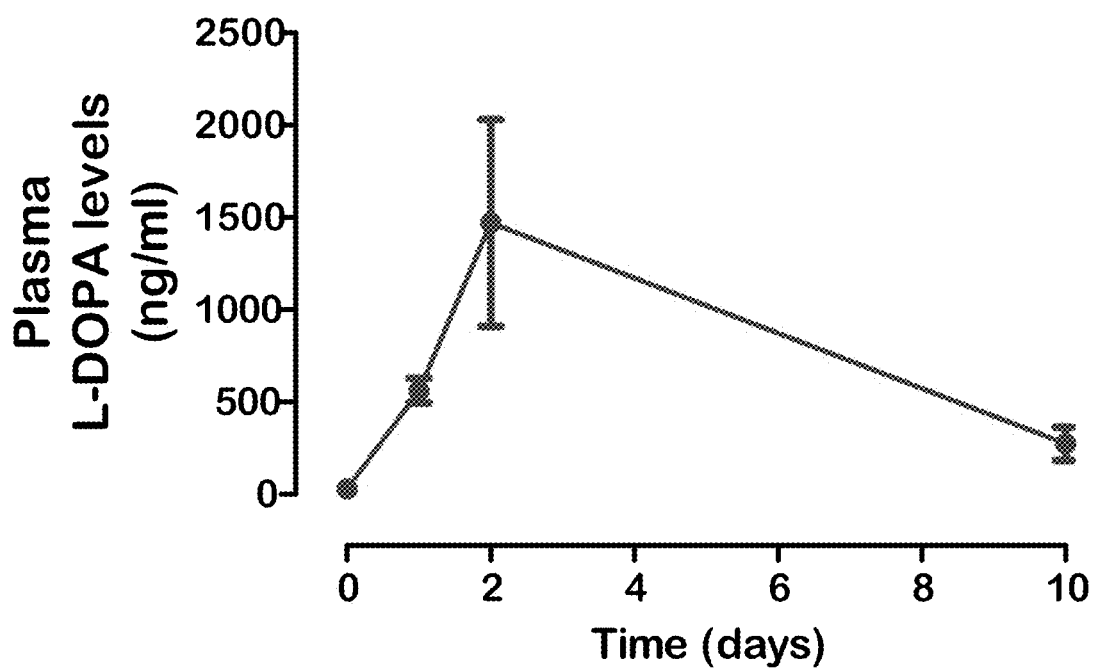
FIGS. 9A-9B show the pharmacokinetic profile of E. coli Nissle 1917 L-DOPA-producing bacteria ($EcN^1_{L\text{-}DOPA}$) in mouse model of PD. C57BL/6 mice received single oral administration of $EcN^1_{L\text{-}DOPA}$ and were co-treated with the decarboxylase inhibitor benserazide.
Figure 9B:
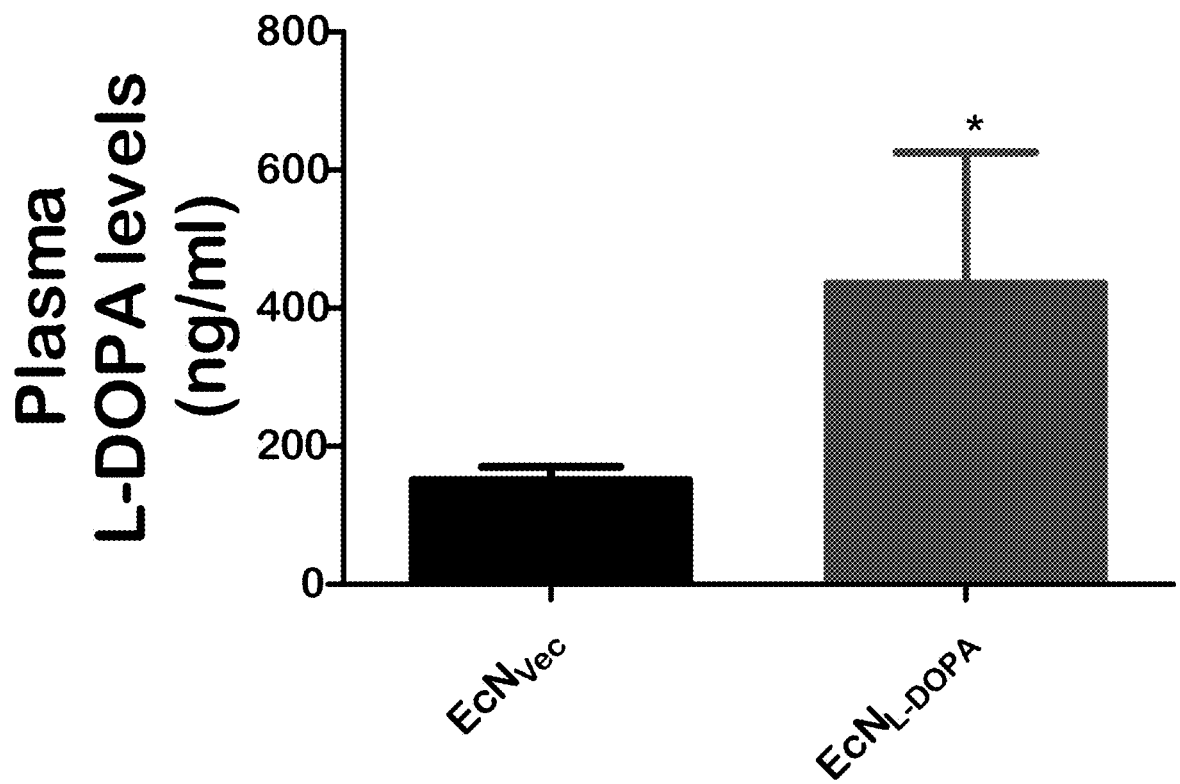

Example 8: *E. coli* Nissle 1917 L-DOPA-Producing Bacteria ($EcN^1_{L-DOPA}$) Increase Plasma L-DOPA Levels to a Therapeutic Level in a Mouse Model of PD Approximately 15-17 week-old male and female C57BL/6 mice (n=6) received a single oral administration of $10^9$ CFU/150 µl of $EcN^1_{L-DOPA}$ or $EcN_{Vec}$ containing L-tyrosine (100 mg/kg) plus a single i.p. injection of benserazide (12.5 mg/kg). Plasma samples collected prior to administration and again on days 1, 2 and 10 were subjected to HPLC analysis for measurements of L-DOPA levels as previously described in our publications. Plasma L-DOPA levels peaked on day 2 after a single oral administration of $EcN^1_{L-DOPA}$ and then declined over a period of ten days (FIG. 9A). Notably, the peak plasma level reached 1500 ng/ml, which is similar to the standard tablet form of L-DOPA treatment in PD patients. In contrast, $EcN_{Vec}$ administration did not increase plasma L-DOPA levels as expected (FIG. 9B). The pharmacokinetic profile also paralleled the colonization profile (FIG. 8). Together the results from the colonization and PK profile reveal that alternate-day administration of $EcN^1_{L-DOPA}$ will provide stable plasma levels of L-DOPA, which may provide great clinical benefits by avoiding the dose fluctuations and dyskinesia associated with current L-DOPA treatment. We adopted an alternate-day $EcN^1_{L-DOPA}$ treatment paradigm for preclinical efficacy studies in the animal models described below.

Example 9: *E. coli* Nissle 1917 L-DOPA-Producing Bacteria ($EcN^1_{L-DOPA}$) Alleviate Parkinsonian Neurological Symptoms, Depressive and Anxiety-Like Behavior in the Chronic, Progressively Degenerative MitoPark Mouse Model of PD MitoPark motor performance at age 8 weeks does not differ from age-matched controls. However, starting at age 12 weeks, these mice display significantly reduced locomotor activity that progressively worsens with age. It is the best progressive degenerative mouse of PD available to date. At 16 weeks, MitoPark mice exhibit a PD phenotype. We treated 16-week-old male and female MitoPark and control mice (n=6/group) via oral administration of $10^9$ CFU/150 µl of $EcN^1_{L-DOPA}$ or $EcN_{Vec}$ containing L-tyrosine (100 mg/kg) and i.p. injection of benserazide (12.5 mg/kg) on alternate days from 16-20 weeks. Wild-type littermate mice from the MitoPark breeding colony were used as control mice. Animals were assessed weekly for a) exploratory locomotor activity via an open-field test (OFT) recorded using the Versamax computerized activity monitoring system, b) vestibulomotor function and motor coordination using the Rotarod, and c) depression- and anxiety-like behavior using the forced swim test (FST) and the Versamax OFT, respectively.

Figure 10A:
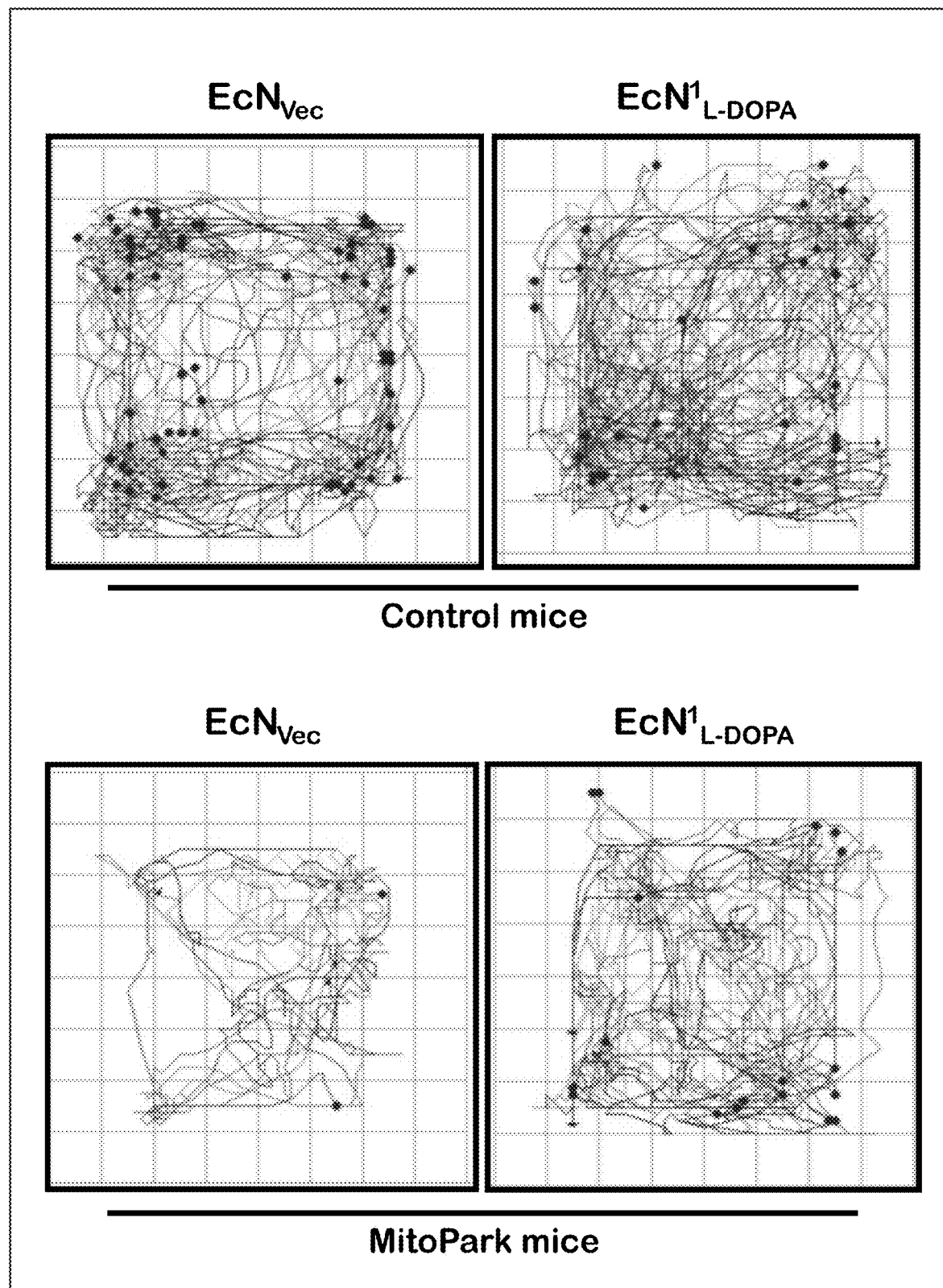
FIGS. 10A-10D show E. coli Nissle 1917 L-DOPA-producing bacteria ($EcN^1_{L\text{-}DOPA}$) alleviates Parkinsonian motor symptoms in the chronic, progressively degenerative MitoPark mouse model of PD. Sixteen-week-old MitoPark (MP) and Littermate control (LM) mice (male and female, n=3) received oral administration of $10^9$ CFU/150 ul of either $EcN^1_{L\text{-}DOP}$ or $EcN_{Vec}$ containing L-Tyrosine (100 mg/kg) and were co-treated with benserazide (12.5 mg/kg i.p.) on alternate days. Animals were assessed weekly for 4 weeks for exploratory locomotor activity via an open-field test recorded using the Versamax computerized activity monitoring system. Representative data shown for age 20 weeks.
Figure 10B:
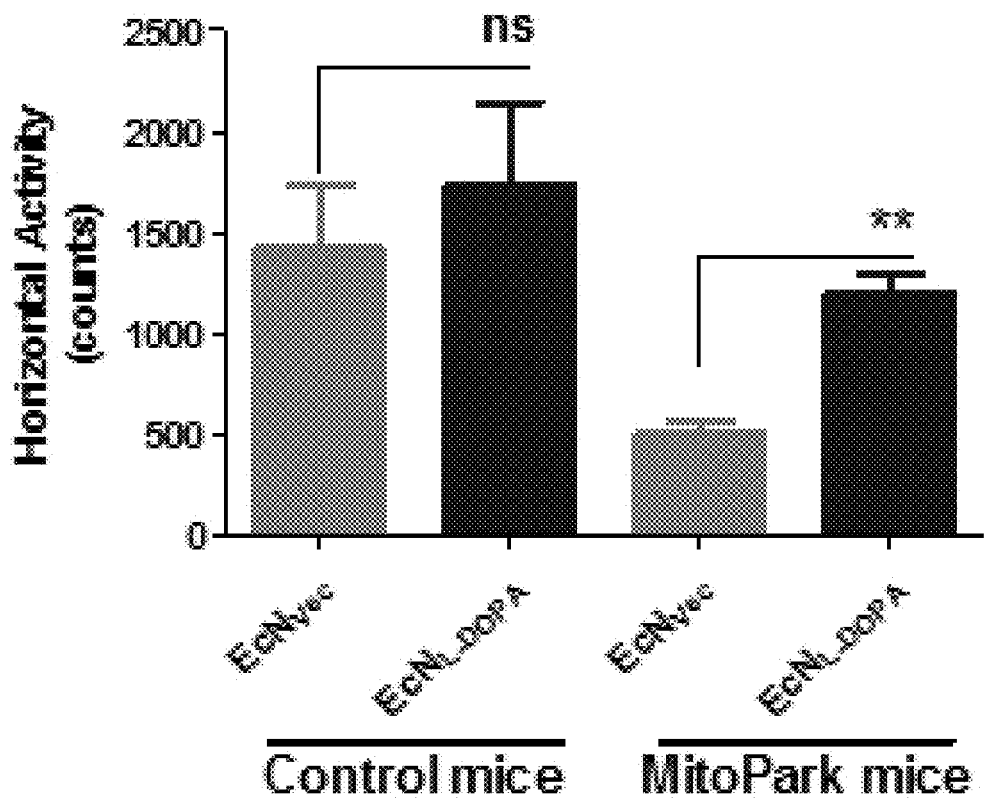
Figure 10C:
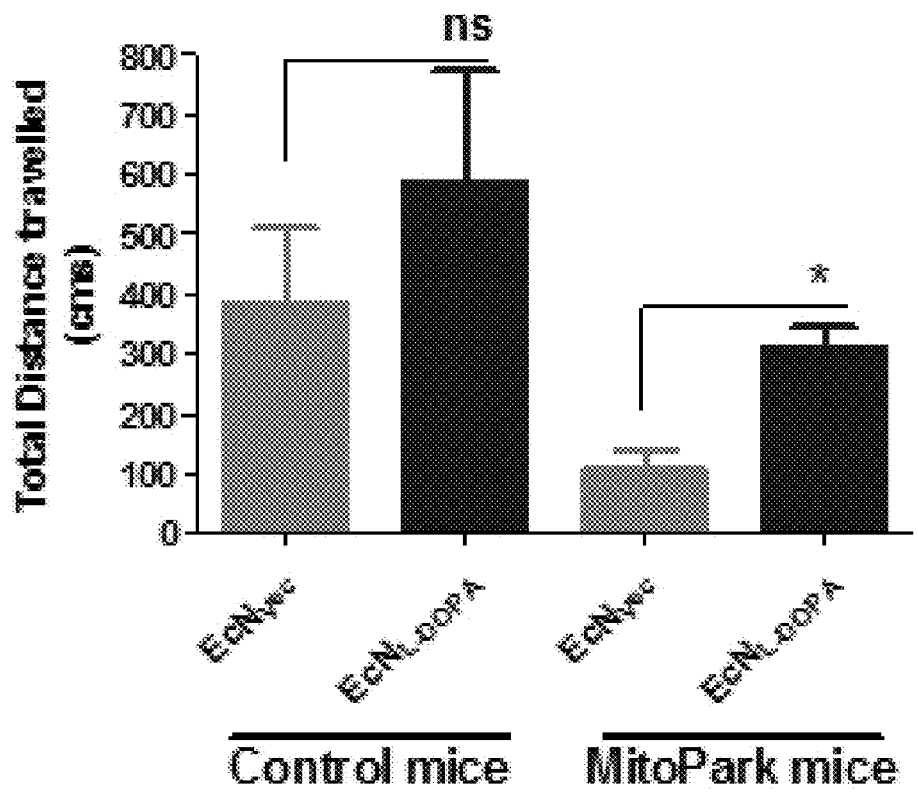
Figure 10D:
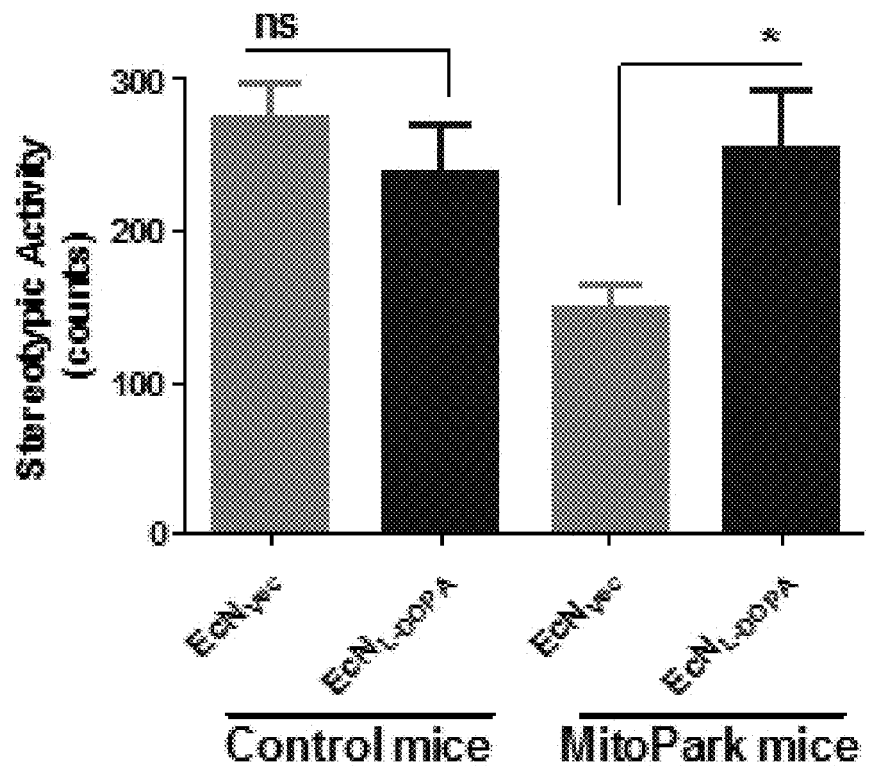

Attenuation of PD-Related Movement Deficits in the MitoPark Transgenic Mouse Model MitoPark mice at age 20 weeks displayed significantly reduced locomotor activity compared to control mice (FIG. 10A-D). Oral administration of $EcN^1_{L-DOPA}$ increased locomotor activity in both MitoPark and control mice as seen in the representative computerized motor activity plots (FIG. 10A). Quantitative analysis of the data embedded in the Versamax motor activity plot revealed that $EcN_{Vec}$-administered 20-week MitoPark mice exhibited decreased horizontal locomotor activity (FIG. 10B), total distance traveled (FIG. 10C), stereotypy (FIG. 10D) compared to $EcN_{Vec}$-administered control mice; in the Versamax, stereotypy arises from grooming and head-bobbing, which are more common in mice that are not physically or behaviorally distressed. Oral administration of $EcN^1_{L-DOPA}$ significantly alleviated the deficits in horizontal activity, total distance traveled and stereotypy in MitoPark mice with no significant effect in control mice. However, oral administration of $EcN_{Vec}$ did not have any significant effects on motor deficits in either MitoPark or control mice (FIG. 10A-D). Together this study suggests that $EcN^1_{L-DOPA}$ alleviates key neurological deficits in the MitoPark mouse model of PD.

Anti-Depressive and Anti-Anxiety Effect of $EcN^1_{L-DOPA}$ in Mouse Model

Figure 11:
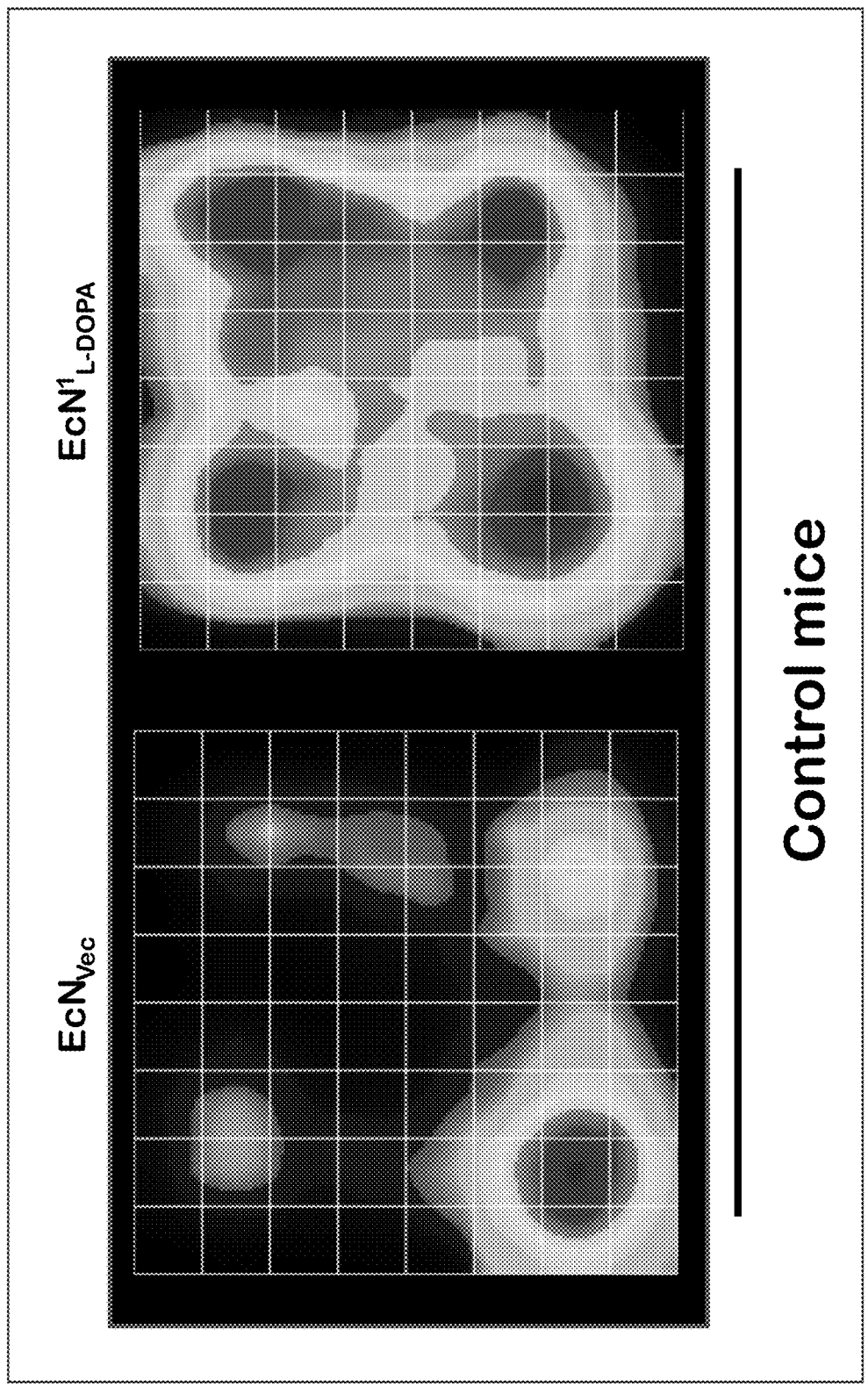
FIG. 11 shows E. coli Nissle 1917 L-DOPA-producing bacteria ($EcN^1_{L\text{-}DOPA}$) reduce anxiety-like behavior in Control mice. Heat map of animal's exploratory behavior in Versamax open-field test. Quadrant 2 (Q2) is the most openly exposed quadrant. Animals were assessed weekly for 4 weeks for anxiety using the Versamax and forced swim test. Representative data shown for age 20 weeks. See brief description of FIG. 10 for animal treatment paradigm.
Figure 12A:
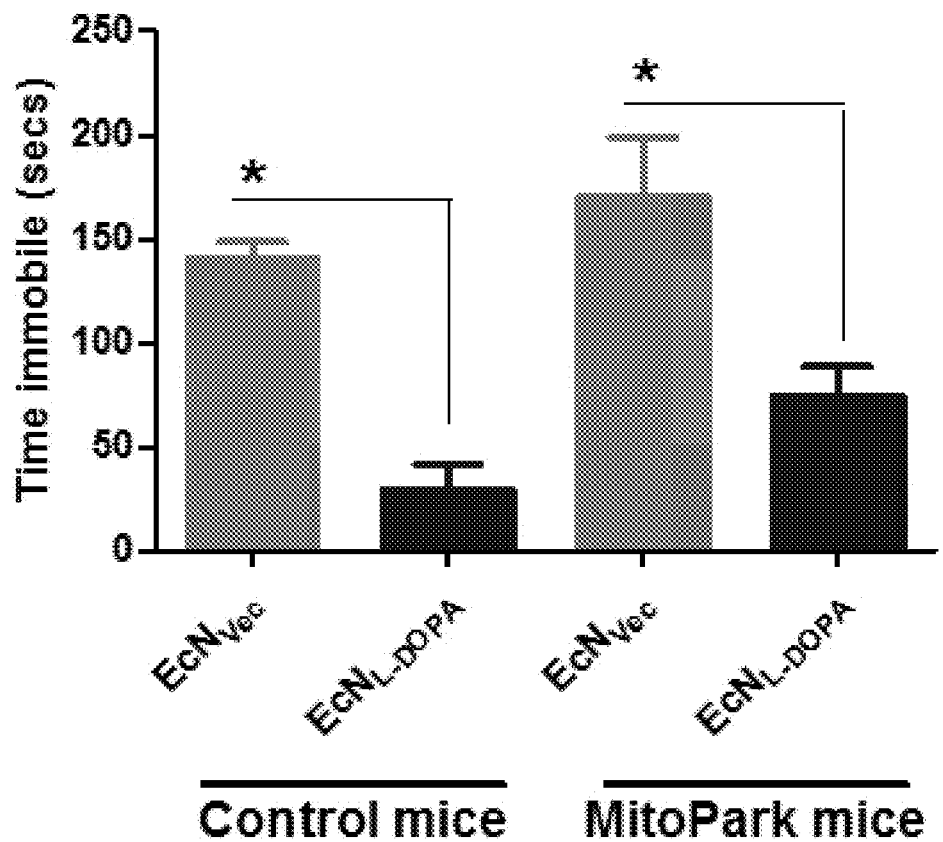
FIGS. 12A-12B show E. coli Nissle 1917 L-DOPA-producing bacteria ($EcN^1_{L\text{-}DOPA}$) reduce depression-like behavior in Control and MitoPark mice in Forced Swim Test.
Figure 12B:
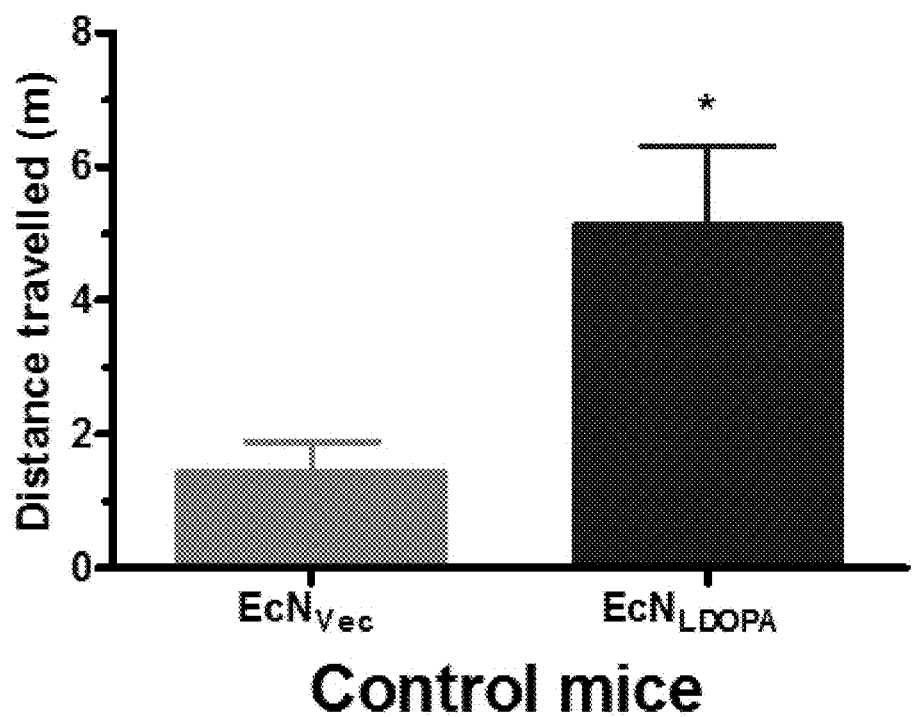

Depression and anxiety assessments were performed using the FST and the Versamax OFT, respectively. To measure anxiety, the OFT exploits a mouse's natural tendency to hug walls, especially opaque ones, and to avoid openly exposed areas when spontaneously exploring a novel environment. Thus, more time spent in zones or quadrants farthest from opaque walls (i.e., most openly exposed) can serve as an index of reduced anxiety. In this unforced locomotor assessment, Control mice receiving $EcN^1_{L-DOPA}$ were significantly less anxious than $EcN_{Vec}$-treated mice (FIG. 11). The FST subjects mice to an inescapable, stress-inducing scenario that invariably leads to episodes of behavioral despair, or giving up, as measured by immobility. Various measures of immobility, including latency, count, cumulative duration, and even distance, can be used to gauge motivational deficits linked to depression. To quantify immobility, we used ANY-maze computerized video-tracking and analysis software, as described in our recent publications, which employs a mobility threshold that allows for only those minor movements necessary to tread water. Thus, higher immobility scores and shorter distances represent a more depressive phenotype, whereas lower immobility and longer distances reflect a more motivated, stress-coping phenotype. In FST, MitoPark mice at age 20 weeks were significantly more immobile than age-matched control mice, suggesting that Parkinsonian mice express a more depressive phenotype than do control mice (FIG. 12A). However, MitoPark mice administered with $EcN^1_{L-DOPA}$ were significantly less immobile compared to $EcN_{Vec}$-administered MitoPark mice. Importantly, when compared to EcN$_{Vec}$-administered control mice, control mice receiving EcN$^1_{L\text{-}DOPA}$ were not only significantly less immobile, their increased activity exceeded the mobility threshold enough to show that their bodies cumulatively moved a significantly greater distance. This suggests the mice were highly motivated to escape rather than just tread water, further indicating that EcN$^1_{L\text{-}DOPA}$ can be an effective treatment for depression and motivational impairments in otherwise healthy individuals. Collectively, our FST and OFT results clearly demonstrate the anti-depressive and anti-anxiety effects of EcN$^1_{L\text{-}DOPA}$ in both control and PD mouse models.

Improvement in Vestibulomotor Function and Motor Coordination

This assessment was performed using an accelerated rotarod paradigm, wherein the latency to falling off the accelerating rod is a measure of vestibulomotor function and motor coordination. MitoPark mice at 20 weeks displayed significantly less time on the rotarod compared to control mice (FIG. 13). However, EcN$^1_{L\text{-}DOPA}$ treatment significantly increased the time spent on the rotarod in MitoPark mice, but the EcN$_{Vec}$ treatment did not (FIG. 13). Neither EcN$^1_{L\text{-}DOPA}$ or EcN$_{Vec}$ had any effect on control mice (FIG. 13). This study suggests that EcN$^1_{L\text{-}DOPA}$ protects against the progressive loss of vestibulomotor function and motor coordination in the MitoPark mouse model of PD.

Collectively, our data support a strong colonization profile of newly developed L-DOPA-producing E. coli Nissle bacteria (EcN$^1_{L\text{-}DOPA}$) and its excellent pharmacokinetics and profile of plasma L-DOPA levels. Notably, EcN$^1_{L\text{-}DOPA}$ treatment alleviates Parkinsonian neurobehavioral symptoms in a preclinical animal model of PD. Furthermore, EcN$^1_{L\text{-}DOPA}$ reduces anxiety and depressive behaviors and enhances motivational behavior in both control and PD mice. Thus E. coli Nissle 1917 L-DOPA-producing bacteria could be a viable therapeutic as a novel L-DOPA delivery mechanism with minimal side effects as well as a new anti-depressant and anxiolytic probiotic for treating PD and other neuropsychiatric disorders.

Example 10: Sequences

```
HpaB gene sequence (SEQ ID NO: 1):
   1 atgaaaccag aagatttccg cgccagtacc caacgtccgt tcaccgggga agagtatctg
  61 aaaagcctgc aggatggtcg cgagatctat atctatggcg agcgagtgaa agacgtcact
 121 actcatccgg catttcgtaa tgcggcagcg tctgttgccc aactgtacga cgcgctgcac
 181 aaaccggaga tgcaggactc tctgtgttgg aacaccgaca ccggcagcgg cggctatacc
 241 cataaattct tccgcgtggc gaaaagtgcc gacgacctgc gccagcaacg cgacgccatc
 301 gctgagtggt cacgcctgag ctatggctga atgggccgta ccccagacta caaagctgct
 361 ttcggttgcg cactgggcgc gaatccgggc ttttacggtc agttcgagca gaacgcccgt
 421 aactggtata cccgtattca ggaaactggc ctctacttta accacgcgat tgttaaccca
 481 ccgatcgatc gtcatttgcc gaccgataaa gtgaaagacg tttacatcaa gctggaaaaa
 541 gagactgacg ccgggattat cgttagcggt gcgaaagtgg ttgccaccaa ctcggcgctg
 601 actcactaca acatggttgg cttcggctcg gcacaagtaa tgggcgaaaa cccggacttc
 661 gcgctgatgt tcgttgcgcc aatggatgct gatggcgtga aattaatctc ccgcgcctct
 721 tatgagatgg tcgcgggtgc taccggctca ccgtatgact acccgctctc cagccgcttc
 781 gatgagaatg atgcgattct ggtgatggat aacgtgctga tcccatggga aaacgtgctg
 841 atctaccgcg attttgatcg ctgccgtcgc tggacgatgg aaggcggttt tgcccgtatg
 901 tatccgctgc aagcctgtgt gcgcctggca gtgaaactcg acttcattac ggcactgctg
 961 aaaaaatcac tcgaatgtac cggcaccctg gagttccgtg gtgtgcaggc cgatctcggt
1021 gaagtggtgg cgtggcgcaa caccttctgg gcattgagtg actcgatgtg ttctgaagcg
1081 acgccgtggg tcaacggggc ttatttaccg gatcatgccg cactgcaaac ctatcgcgta
1141 ctggcaccaa tggcctacgc gaagatcaaa aacattatcg aacgcaacgt taccagtggc
1201 ctgatctacc tcccttccag tgcccgtgac ctgaacaatc cgcagatcga ccagtatctg
1261 gcgaagtatg tgcgcggttc gaatggtatg atcacgtcc agcgcatcaa gatcctcaaa
1321 ctgatgtggg acgccattgg cagcgagttt ggtggtcgcc acgaactgta tgaaatcaac
1381 tactccggta gccaggatga gattcgcctg cagtgtctgc gccaggcaca aagctccggc
1441 aatatggaca agatgatggc gatggttgat cgctgcctgt cggaatacga ccagaacggc
1501 tggactgtgc cgcacctgca caacaacgac gatatccaaca tgctggataa gctgctgaaa
1561 taa
```

The HpaC gene sequence (SEQ ID NO: 2):

```
  1    atgcaattag atgaacaacg cctgcgcttt cgtgacgcga tggccagcct gtcggcagcg 61    gtaaatatta tcaccaccga gggcgacacc ggacaatgcg ggattacggc aacggctgtc 121    tgctcggtca cggatacacc accgtcgctg atggtgtgca ttaacgccaa cagtgcgatg 181    aacccggttt ttcagggcaa cggcaagttg tgcgtcaacg tcctcaacca tgagcaggaa 241    ctgatggcac gccacttcgc gggcatgaca ggcatggcga tggaagagcg ttttagcctc 301    tcatgctggc aaaaaggtcc gctggcgcag ccggtgctaa aaggttcgct ggccagtctt 361    gaaggtgaga tccgcgatgt gcaggcaatt ggcacacatc tggtgtatct ggtggagatt 421    aaaaacatca tcctcagtgc agaaggtcac ggacttatct actttaaacg ccgtttccat 481    ccggtgatgc tggaaatgga agctgcgatt taa
```

Example 11: Re-Engineered EcN²$_{L-DOPA}$ Probiotic

We have cloned the codon-optimized L-DOPA biosynthesis genes 4-hydroxyphenylacetate 3-monooxygenase (HpaB) and its FAD reductase (HpaC) into a re-constructed, BBa_J23111 promoter-based vector and stably transformed EcN to express the HpaB and HpaC enzymes. We chose EcN as the delivery vehicle for continuous in situ production of L-DOPA (EcN²$_{L-DOPA}$) because this commensal strain has proven to be a safe and effective probiotic supplement for therapeutic development in humans. This example demonstrates that: 1) the genetically reengineered, second-generation L-DOPA-producing E. coli Nissle 1917 probiotic strain (EcN²$_{L-DOPA}$) produces and releases L-DOPA in vitro without supplementing L-tyrosine, and 2) oral administration of this highly efficient EcN²$_{L-DOPA}$ strain readily colonizes the mouse gut, achieves a steady-state plasma L-DOPA level that corresponds to the clinically effective plasma level in PD patients, and increases L-DOPA and dopamine levels in the brain.

We confirmed via HPLC that our 2$^{nd}$-generation recombinant E. coli Nissle 1917 strain expressing HpaBC genes (EcN²$_{L-DOPA}$) was more efficient and effective than the 1$^{st}$-generation L-DOPA-expressing system (EcN¹$_{L-DOPA}$) at producing large amounts of L-DOPA in bacterial culture media, even without supplementing with L-tyrosine (FIG. 14). Importantly, we also demonstrated that the genetically re-engineered EcN²$_{L-DOPA}$ colonized the gut of C57BL mice, constitutively produced stable levels of plasma L-DOPA corresponding to clinically effective plasma levels in PD patients, and significantly increased striatal L-DOPA and DA (FIGS. 15-17). We achieved statistical significance using 4-6 mice/group, indicating a robust L-DOPA replacement strategy. Neurochemical and colonization assays were run in blinded triplicates. In addition, a pilot study using a relatively small number of animals indicates that oral treatment with EcN²$_{L-DOPA}$ on alternate days for 1 wk alleviates key motor deficits in MitoPark (MP) mice, a chronically progressive neurodegenerative mouse model of PD.

Characterization and Optimization of Microbial L-DOPA Synthesis in Genetically Engineered Probiotic E. coli.

We optimized the system's translational versatility and flexibility by re-constructing the L-DOPA-expressing plasmid. We used strong synthetic constitutive 6$^{70}$ promoters from the Registry of Standard Biological Parts (parts.i-gem.org/Catalog) and optimized HpaBC gene codons for expression in E. coli. Briefly, the native promoter of a pRham-Kanamycin vector was replaced with the constitutive synthetic promoters BBa_J23100, BBa_J23105, and BBa_J23111, herein referred as P1, P2 and P3, respectively, which are derived from the consensus promoter BBa_J23119 and have relative reported activities tested in the TG1 strain as 1, 0.24, and 0.58 for P1, P2, and P3, respectively. An IDT-synthesized gBlocks gene fragment containing codon-optimized HpaBC genes was inserted into the generated P1, P2 and P3 vectors (FIG. 14A). L-DOPA production from the EcN containing the newly constructed L-DOPA-producing plasmids was quantitatively assayed by HPLC. Surprisingly, even in LB media (normal L-tyrosine 1-1.4 mM) lacking L-tyrosine supplementation, all new systems were able to produce much higher concentrations of L-DOPA than the previous RSF1030-based EcN¹$_{L-DOPA}$ system, resulting in a more gradual L-DOPA production with yield strengths for the P2-, P1-, and P3-based system being 5, 7, and 31 times that of the RSF1030 system (FIG. 14B). Collectively, our optimization strategy has the advantage of allowing more effective and efficient L-DOPA production, even without adding L-tyrosine. Since our optimized P1-P3 EcN L-DOPA system synthesizes a graded level of L-DOPA with a normal L-tyrosine level, this improved system allows us to personalize L-DOPA delivery depending on each patient's DA needs and to fine-tune dose titrations. Since our P3-based L-DOPA-expressing system (referred to as EcN²$_{L-DOPA}$) yielded the highest L-DOPA production (FIG. 14B), we used it for the following in vivo preliminary studies.

EcN²$_{L-DOPA}$ colonization and L-DOPA production in a mouse model

We used C57BL/6NCrl mice to test whether orally administered EcN²$_{L-DOPA}$ colonizes the mouse gut and effectively elevates plasma L-DOPA. For colonization studies, fecal pellets were collected daily from mice for 4 days following a single oral dose of 10$^9$ CFU (colony forming unit) P3-based EcN²$_{L-DOPA}$ or PBS and the peripheral AADC inhibitor benserazide (Bz, 12.5 mg/kg, i.p.) to prevent breakdown of L-DOPA. EcN²$_{L-DOPA}$ colonization of the mouse gut increased rapidly (FIG. 15A), peaking at days 1-2 post-challenge (4.8×10$^7$ cfu/g), and then gradually declined until it dropped to baseline on days 3-4, as revealed by qPCR detection of a unique sequence for the EcN strain present in the fecal pellets following a previous method. The colonization profile suggests that EcN²$_{L-DOPA}$ treatment on alternate days represents a suitable paradigm for achieving stable EcN²$_{L-DOPA}$ gut colonization in mice. Next, we examined whether EcN²$_{L-DOPA}$ treatment on alternate days leads to stable plasma L-DOPA levels. Mice were orally administered a single daily dose of 10$^9$ CFU EcN²$_{L-DOPA}$ or PBS and also Bz (50 mg/kg) 3 times/day for 1 and 2 days. Plasma samples collected through submandibular sampling prior to $EcN^2_{L-DOPA}$ treatment (serving as baseline), and at 4, 8, 16, 24 and 48 h post-$EcN^2_{L-DOPA}$ and Bz (50 mg/kg) treatment, were assayed for L-DOPA production by HPLC. We found that following $EcN^2_{L-DOPA}$ administration, plasma levels of L-DOPA gradually increased over time, reaching 1387.6 ng/ml at 1 day and then remaining relatively stable until 2 days post-treatment (FIG. 15B). We increased the dose and frequency of Bz because of its short half-life. This repeated Bz treatment paradigm prolonged Bz plasma levels up to 30 h as determined by HPLC (FIG. 16A). These results are clinically important since the optimal therapeutic plasma levels of L-DOPA are considered to be in the range of 300-1600 ng/ml in humans. The plasma L-DOPA profiles suggest that therapeutic plasma levels of L-DOPA can be achieved and maintained stably for at least 48 h following oral administration of a single dose of $EcN^2_{L-DOPA}$. Given these results, combined with the colonization profile showing highest colonization at 1-2 days post $EcN^2_{L-DOPA}$ gavage, we believe that treatment with a single dose of $EcN^2_{L-DOPA}$ in mice on alternate days will induce stable colonization and continuous L-DOPA delivery. Analysis of striatal L-DOPA levels revealed that a single dose of $10^9$ CFU $EcN^2_{L-DOPA}$ and repeated Bz (50 mg/kg) treatment significantly increased L-DOPA levels compared to PBS control mice (FIG. 16B). Importantly, DA levels in striatal tissues were also dramatically increased in mice orally administered with $EcN^2_{L-DOPA}$ for 1-2 days as compared to control animals (FIG. 16C, 2.9- and 2.5-fold increase for 24 h and 48 h post-$EcN^2_{L-DOPA}$, respectively). $EcN^2_{L-DOPA}$ colonization at 48 h post-$EcN^2_{L-DOPA}$ was also determined by qPCR detection of EcN's unique sequence after isolating total DNAs from the intestinal content collected from region-specific gut segments, including duodenum, ileum, cecum and colon. The intestinal content collected from all gut segments showed significant levels of EcN bacteria (FIG. 16D), suggesting our genetically reengineered bacterium successfully colonized throughout the mouse gut.

To further evaluate whether $EcN_{L-DOPA}$ adapts well in the gut without producing any significant adverse effect in the target tissue, histopathological and clinical chemistry analyses were performed. We treated animals with a single dose ($10^9$ CFU) of the $1^{st}$-generation system ($EcN^1_{L-DOPA}$) or PBS for 7 days. Histological analyses of the ileum, cecum and colon of $EcN^1_{L-DOPA}$-treated animals and blinded evaluation of histological scores for inflammation, edema, stomal collapse, gland hyperplasia, and distribution revealed no pathological changes (FIG. 17A), suggesting that $EcN^1_{L-DOPA}$ treatment did not induce toxicity, inflammation, or neoplastic processes in the mouse gut. Blood chemistry results consistently showed no significant difference between control and $EcN^1_{L-DOPA}$-treated mice (Table 1). In addition, to further determine if $EcN^1_{L-DOPA}$ induces any dysbiosis or imbalance in the gut microbiota, we performed fecal metagenomic analyses. No significant differences in the key family of bacteria were observed, indicating that $EcN^1_{L-DOPA}$ does not negatively impact gut microbiota (FIG. 17B). Together, these results suggest that colonized $EcN^2_{L-DOPA}$ efficiently produce stable levels of L-DOPA in mice corresponding to clinically effective plasma levels in human subjects without any significant adverse effect, and the microbially delivered L-DOPA crosses the BBB to the brain where it is further converted to enhance levels of DA. $EcN^2_{L-DOPA}$ treatment alleviates locomotor deficits in MP mice.

To examine the effects of $EcN^2_{L-DOPA}$ on locomotor deficits, we performed a pilot study using a small number of 11- to 16-wk-old MP and littermate control mice (n=4-5/group), which were gender-balanced and blindly randomized to groups orally administered a single dose of either $10^9$ CFU $EcN^2_{L-DOPA}$ or PBS in combination with Bz on alternate days for 1 wk. All mice were assessed post-treatment for open-field locomotor activity using the VersaMax computerized activity monitoring system. Representative maps of movement paths (FIG. 18A) and analyses of mean horizontal activity (FIG. 18B) revealed that 12- to 17-wk MP mice displayed significantly reduced locomotor activity compared to littermate control mice and that orally administered $EcN^2_{L-DOPA}$ increased locomotor activity in MP mice. Moreover, MP mice exhibited decreased stereotypy (FIG. 18C) compared to control mice. Importantly, orally administered $EcN^2_{L-DOPA}$ significantly attenuated motor deficits in MP mice while having no significant effect in control mice. Together, these results clearly suggest that alternate-day treatments with $EcN^2_{L-DOPA}$ for 1 wk alleviate key motor deficits in the MP mouse model of PD.

Please note that we used a PBS control only in early experiments, but we have now generated EcN vector control ($EcN_{Vec}$) data showing no significant change in plasma L-DOPA levels compared to PBS controls (FIG. 19).

The newly constructed $2^{nd}$-generation L-DOPA-expressing systems allow a gradual and more efficient L-DOPA production without supplementing the L-tyrosine substrate, providing more flexibility in terms of dose titration than the $1^{st}$-generation (RSF1030-based) system. We have strong prelim data demonstrating our $2^{nd}$-generation $EcN^2_{L-DOPA}$ colonizes the mouse gut, produces stable therapeutic plasma levels of L-DOPA and increases brain DA levels. As an alternate approach, we will consider using inducible control of L-DOPA synthesis as a strategy to achieve better therapeutic efficacy in relieving PD symptoms and preventing LID development. An inducible control of L-DOPA production is also valuable in preventing overmedication and related harmful drug reactions. Although $EcN^2_{L-DOPA}$ has a kanamycin-resistant plasmid, high doses of antibiotics can eliminate the $EcN^2_{L-DOPA}$ bacteria. The combination of antibiotic treatment and transient colonization over 2-3 days offer an adequate mitigation strategy in case of any overmedication or adverse drug reaction with $EcN^2_{L-DOPA}$ treatment. To further improve the versatility and flexibility of our L-DOPA-expressing systems, we will consider developing a chromosomal integration and expression system for L-DOPA production.

We recognize that the clinical utility of $EcN^2_{L-DOPA}$ treatment in PD patients will require further optimization depending on the gut motility rate, dietary factor and severity of the disease. Since our optimized P1-P3 EcN L-DOPA system (FIG. 14) synthesizes a graded level of L-DOPA with normal L-tyrosine level, this improved system can be adopted to personalize the L-DOPA delivery depending on each patient's DA needs and to carry out up- and down-titration of L-DOPA medication in clinical settings. The plasma L-DOPA level can be used as an index for up/down titration to optimize the correct dose needed for patients.

hpaBC Cloning and Expression

To create an E. coli Nissle (EcN) strain to produce elevated levels of L-DOPA we first assembled recombinant plasmids to express a synthetic hpaBC gene construct. The hpaBC genes collectively encode 4-hydroxyphenylacetate-3-hydrolase, which converts L-Tyrosine to L-DOPA and are found naturally in selected E. coli strains. A codon-optimized variant was synthesized (Integrated DNA Technologies, Coralville Iowa). This new hpaBC variant shared 79% nucleotide sequence identity with the original genes and included additional bases on the 5' and 3' ends to facilitate cloning (SEQ ID NO: 3).

The synthetic hpaBC genes were cloned under control of the rhamanose (rha) promoter and operator for expression in EcN. For this, the commercially available pRHAM vector (Lucigen, Madison Wis.) was used. Kanamycin resistant transformants were screened for synthesis of L-DOPA in the presence of 1% rhamnose for dark colonies, indicative of oxidation of L-DOPA to dopachrome with subsequent polymerization to form the pigment melanin (Claus, H., and H. Decker. 2006. Bacterial tyrosinases. Syst. Appl. Microbiol. 29:3-14). Correct insertion of hpaBC into the pRham vector (vector pRham-hpaBC$_{syn}$) was confirmed by characterizing plasmid DNA by restriction enzyme digestion and DNA sequencing.

The pRham-hpaBC$_{syn}$ plasmid was introduced to EcN by chemical transformation for characterization in the experiments described elsewhere. Additional variants of pRham-hpaBC$_{syn}$ were also made to replace the rha promoter with promoters that allow constitutive expression of hpaBC. Three synthetic σ$^{70}$ promoter sequences ("parts" BBa_J23100 [P1], BBa_J23105 [P2], and BBa_J23111 [P3]) from the Anderson Promoter Collection (iGEM.org) were selected based on different levels of transcriptional activity afforded by each sequence. Each promoter sequences were incorporated into PCR primers used for inverse PCR reactions using pRham-hpaBC$_{syn}$ as template DNA. Transformants constitutively expressing rhaBC were identified by colonies that turned dark brown following incubation in the absence of L-rhamnose. As predicted, expression of hpaBC from promoters P1, P2, and P3 (FIG. 20) resulted in different levels of constitutive L-DOPA production.

```
hpaBC_syn nucleotide sequence (SEQ ID NO: 3):
GAAGGAGATATACATATGAAACCCGAAGATTTCCGTGCTTCAACACAGCG CCCTTTCACTGGGGAAGAATACctgAAGAGCCTGCAAGACGGTCGTGAAA

TTTATATTTACGGGGAGCGTGTGAAGGATGTTACGACCCATCCAGCCTTT

CGCAACGCCGCTGCGTCTGTGGCGCAGTTGTATGATGCGTTACACAAACC

TGAGATGCAGGATTCGTTGTGCTGGAACACAGACACGGGTTCGGGAGGAT

ATACTCATAAATTTTTTCGCGTTGCTAAGTCGGCAGACGACCTgCGCCAA

CAACGTGATGCTATTGCTGAGTGGTCACGTCTGTCGTACGGGTGGATGGG

ACGTACACCCGATTATAAAGCGGCGTTTGGATGCGCATTGGGAGCTAACC

CTGGATTCTATGGACAGTTCGAGCAGAATGCCCGCAACTGGTACACACGC

ATTCAAGAAACTGGGTTGTATTTTAATCACGCCATTGTCAATCGCCGAT

CGATCGCCACCTGCCCACGGATAAAGTAAAAGATGTATATATTAAGTTGG

AAAAAGAGACAGACGCAGGGATCATTGTATCAGGCGCCAAGGTGGTTGCG

ACCAATTCTGCCCTGACGCACTACAACATGATCGGCTTTGGATCTGCTCA

AGTGATGGGTGAAAACCCCGATTTTGCACTTATGTTTGTAGCCCCATGG

ACGCTGACGGGGTTAAACTGATTAGCCGCGCATCGTACGAAATGGTCGCC

GGGGCCACAGGCAGTCCGTACGATTATCCTTTATCTAGTCGCTTCGACGA

AAACGACGCGATCTTAGTGATGGATAACGTCCTGATTCCTTGGGAGAACG

TCCTGATCTATCGTGATTTCGACCGCTGCCGTCGTTGGACTATGGAAGGA
```

```
GGCTTCGCTCGCATGTACCCTTTGCAAGCCTGTGTACGCCTTGCTGTCAA

ACTTGATTTCATCACTGCGCTTTTGAAGAAATCGTTAGAGTGTACTGGGA

CGCTGGAGTTCCGTGGTGTCCAAGCCGACCTTGGCGAGGTGGTGGCTTGG

CGTAATACTTTCTGGGCATTATCCGACTCCATGTGCTCGGAAGCAACCCC

CTGGGTCAATGGGGCATACCTTCCCGATCACGCCGCTCTTCAAACCTATC

GCGTACTTGCGCCTATGGCtTATGCTAAGATTAAAAATATTATCGAACGT

AATGTGACTTCCGGCTTAATTTACTTGCCCTCCAGCGCGCGCGATCTGAA

TAATCCTCAAATCGACCAGTATTTAGCGAAGTATGTTCGCGGGAGCAACG

GGATGGATCATGTCCAGCGCATCAAAATCCTTAAGTTAATGTGGGATGCC

ATTGGTTCAGAATTTGGCGGGCGTCATGAACTTTATGAAATTAATTACTC

TGGCTCGCAAGACGAGATCCGTctgCAATGCTTGCGCCAGGCGCAATCCT

CGGGTAATATGGATAAGATGATGGCTATGGTAGACCGCTGCCTGTCCGAG

TACGACCAAAACGGATGGACGGTCCCCCATCTGCATAACAACGATGACAT

TAACATGCTGGATAAGctgctgAAATAACGCAGCAGGAGGTTAAGATGCA

GcTGGACGAACAACGCctgCGCTTTCGTGACGCAATGGCGAGTTTGAGTG

CAGCCGTTAATATCATTACAACAGAAGGGGACGCAGGTCAATGTGGAATC

ACTGCAACGGCCGTGTGCTCAGTTACAGACACTCCGCCTTCATTAATGGT

ATGCATCAATGCTAACTCGGCTATGAATCCTGTCTTCCAAGGCAATGGGA

AATTATGTGTGAACGTCCTGAACCATGAGCAAGAACTGATGGCACGCCAC

TTCGCAGGCATGACAGGTATGGCAATGGAGGAGCGTTTTAGCTTGTCTTG

CTGGCAAAAGGGACCActgGCCCAACCAGTTTTGAAGGGGTCTCTTGCAT

CATTAGAAGGGGAAATCCGCGATGTCCAGGCGATTGGTACACACCTgGTT

TACCTTGTCGAGATCAAGAACATCATTTTATCCGCAGAGGGCCACGGGCT

GATTTACTTTAAACGCCGCTTCCATCCGGTTATGCTGGAAATGGAAGCTG

CAATTTAAGTAAGGAAACATTTATGCGCCTGCATCATCACCACCATCAC

BBa_J23100
                                              (SEQ ID NO: 4)
TTGACGGCTAGCTCAGTCCTAGGTACAGTGCTAGC

BBa_J23105
                                              (SEQ ID NO: 5)
TTTACGGCTAGCTCAGTCCTAGGTACTATGCTAGC

BBa_J23111
                                              (SEQ ID NO: 6)
TTGACGGCTAGCTCAGTCCTAGGTATAGTGCTAGC
```

Example 12: Re-Engineered L-DOPA Microbiome Therapy for Depression and Anxiety

Major depressive disorder (MDD) is a recurrent or chronic mood disorder characterized by experiencing a depressed mood or loss of interest that is present across most situations for at least two weeks. This disorder results in severe psychosocial dysfunction that commonly leads to feelings of hopelessness, helplessness, anxiety and negativity, thus affecting a person's daily activities and general health. Severe depression may lead some people to feel as if life isn't worth living. As one of the most common mental disorder in the world, almost one in five people experiences one episode at some point in their lifetime and over 350 million people of all ages around the world and 17 million American adults are estimated to suffer this disease. As exposure to highly stressful life experiences is one of the most consistently documented risk factors for depression, deployment to combat zones and exposure to combat have long been associated with increased risk of depression and other mental health problems. Several lines of evidence indicate that depression is as common as, or perhaps even more common than posttraumatic stress disorder (PTSD) among combat veterans. Epidemiological studies estimated the prevalence of depression among U.S. military personnel to be 12% among currently deployed, 13.1% among previously deployed, and 5.7% among never deployed. Due to its various presentations, unpredictable course and prognosis, and variable response to treatment, depression often pose huge challenges for clinicians.

The pathophysiology of depression is not yet known, but considerable evidence supports that insufficient activity of monoamine neurotransmitters, increased inflammation, and hypothalamic-pituitary-adrenal (HPA) axis abnormalities contribute to depression. Depression has been shown to integrate circuitry from several neuronal pathways including the noradrenergic, dopaminergic and serotonergic for which it is likely that each unique circuit is involved in the presentation of its symptoms. Traditionally, dysfunction of the highly complex integrated noradrenergic and serotonergic circuitry was associated with the disorder. However, with recent development in neuroimaging and electrophysiological technology, depression modelled in chronic stress rodents indicated that damage within the mesolimbic and corticolimbic dopaminergic circuits leads to MDD symptoms (loss of motivation arousal, impairment in reward prediction, and anhedonia). Reduced concentrations of dopamine metabolites have been detected in postmortem investigation. In mesolimbic pathway, dopaminergic neurons originate from the ventral tegmental area (VTA) and project its axon to nucleus accumbens (NAc). In animal models of depression, depletion of DA from VTA dopaminergic neurons showed an altered activation of its limbic targets. Optogenetic stimulation of VTA resulted in a reduction of behavioral deficits and dopaminergic neuronal cell firing. These effects were reversed when blocking with dopamine receptor antagonists in the NAc. In the corticolimbic pathway, the VTA primarily projects to the prefrontal cortex (PFC) and the anterior cingulate cortex (ACC). Studies in stress-induced rat models have shown that PFC DA neurotransmission exerts an inhibitory control of DA activity in NAc during stress. The corticolimbic DA system dulls DA release in the mesolimbic pathways leading to maintenance of depression-like behavior, for which effects were reversed with depletion of DA in PFC and the anti-depressant therapy. Similarly, the neuroendocrine system is highly influenced by the integrated circuit of the noradrenergic and dopaminergic pathway. In chronic stress rodents, activation of the HPA-axis triggers the release of glucocorticoids, corticotrophin releasing hormones (CRH) and pro-inflammatory cytokines (TNF, IL-1, IL-6). It was proven that under stress and depression, DA, NE and 5-HT transmission is disrupted leading to imbalance and impairment of regulatory feedback loop responsible for turning off the stress response.

The antidepressants selective serotonin reuptake inhibitors (SSRI) followed by the noradrenaline reuptake inhibitors (NRI) that boost serotonin and/or noradrenaline neurotransmission, respectively, are the most commonly medications prescribed. However, both groups of drugs take time—usually four to eight weeks—to work, and show efficacy in only 60-70% of patients. Several strategies have been developed to increase the efficacy of the SSRI and NRI, including using concomitantly an antidepressant with a substance from another drug class, such as those acting on the dopaminergic system. Growing evidence supports the use of dopamine receptor agonist as antidepressant. Currently, manipulation of dopamine contractions in the brain is primarily achieved through the dopamine precursor L-3,4-dihydroxyphenylalanine (L-DOPA) treatment. L-DOPA readily enters the brain, where it is converted into dopamine by the enzyme DOPA decarboxylase (DDC). Evidence has suggested that co-administration with L-DOPA enhances the anti-depressive effects of NRIs. Furthermore, the L-DOPA-converted dopamine can be further converted to noradrenaline by the enzyme dopamine β-monooxygenase, and L-DOPA itself can also be stored by serotonergic afferents, suggesting that L-DOPA acts in the context of depression via various mechanisms. Regrettably, the use of orally tablet dosing of L-DOPA over time results in diminished production of endogenous L-DOPA. More importantly, due to its chronically non-continuous delivery of L-DOPA to the brain, long-term conventional L-DOPA treatment often induces an array of motor fluctuations and other severe complications including dyskinesia. We demonstrated that the $EcN_{L-DOPA}$ colonized the gut of C57BL mice, and constitutively produced plasma L-DOPA. Importantly, the neurotransmitter levels of NE, 5-HT and DA in the frontal cortex dramatically increased for 2-16 h in mice orally administered with a single dose of $10^9$ CFU $EcN_{L-DOPA}$ and Bz (FIG. 21A-C). Surprisingly, administration of $EcN_{L-DOPA}$ improved depression- and anxiety-like behavior in control C57BL mice (FIG. 22).

Antidepressant and Anxiolytic Effects of $EcN_{L-DOPA}$ in Mice

Depression and anxiety were assessed in mice using the forced swim test (FST), open-field test (OFT) and elevated plus maze (EPM). FST subjects mice to an inescapable, stress-inducing task that invariably leads to behavioral despair as measured by lower mobility. The OFT relies on a mouse's natural tendency to hug opaque walls, avoiding openly exposed areas when spontaneously exploring novel areas. More time spent in the most openly exposed areas serves as an index of reduced anxiety. The EPM measures anxiety based on the mouse's positive thigmotactic aversion to open spaces, with reduced anxiety indicated by more time spent in the open arms and higher total distance traveled. C57BL/6NCrl mice orally receiving a single dose of $10^9$ CFU $EcN_{L-DOPA}$ and 12.5 mg/kg Bz on alternate days for one month were significantly less anxious than or PBS vehicle-treated control mice as evidenced by the representative heat map showing more time spent in the most openly exposed OFT quadrant (Q2) relative to the least exposed, opposite corner and increased overall horizontal activity (FIG. 22A) and by increased time spent in open arms and total distances in EPM (FIG. 22B). When compared to control mice, mice receiving $EcN_{L-DOPA}$ were significantly more mobile and cumulatively moved a significantly greater distance in the FST (FIG. 22C), suggesting the mice were highly motivated to escape rather than just tread water, indicating that $EcN_{L-DOPA}$ effectively treats depression-like motivational impairments in otherwise healthy individuals. Our behavior results clearly demonstrate the antidepressant and anxiolytic effects of $EcN_{L-DOPA}$ in a mouse model.

What is claimed is:

1. A method for treating Parkinson's disease comprising: administering to a subject in need thereof an effective amount of a composition comprising a recombinant microbial cell capable of producing L-DOPA, wherein said recombinant microbial cell colonizes the gut of said subject; and
providing L-DOPA in a sustained manner, wherein L-DOPA produced by the recombinant microbial cell in the gut crosses the blood-brain barrier and increases dopamine levels in the brain to alleviate neurological symptoms of Parkinson's disease.

2. The method of claim 1, wherein said recombinant microbial cell is a probiotic.

3. The method of claim 2, wherein said probiotic is *E. coli* Nissle 1917.

4. The method of claim 1, wherein said composition is administered orally.

5. The method of claim 1, wherein said composition is administered on alternate days.

6. The method of claim 1, wherein said subject is a mammal.

7. The method of claim 6, wherein said mammal is a human.

8. The method of claim 1, wherein said effective amount comprises from about $10^6$ colony forming units (CFU) to about $10^{12}$ CFU of said recombinant microbial cell.

9. The method of claim 8, wherein said effective amount comprises about $10^9$ CFU of said recombinant microbial cell.

10. The method of claim 1 further comprising: co-administering to said subject an effective amount of an aromatic amino acid- or DOPA-decarboxylase inhibitor.

11. The method of claim 10, wherein said DOPA decarboxylase inhibitor is carbidopa or benserazide.

12. The method of claim 1, wherein said composition further comprises L-Tyrosine.

13. The method of claim 1, wherein said recombinant microbial cell comprises a hpaB and hpaC nucleotide sequence as set forth in SEQ ID NO: 1 and 2 or as set forth in SEQ ID NO: 3.

14. The method of claim 13, wherein said hpaB and hpaC nucleotide sequence is operably linked to promoter sequence comprising one or more of SEQ ID NOs: 4-6.

15. A method of treating depression and/or anxiety and improving motivational performance comprising: administering to a subject in need thereof an effective amount of a composition comprising a recombinant microbial cell capable of producing L-DOPA, wherein said recombinant microbial cell colonizes the gut of said subject; and
providing L-DOPA in a sustained manner, wherein L-DOPA produced by the recombinant microbial cell in the gut crosses the blood-brain barrier and increases dopamine levels in the brain to alleviate symptoms of depression and/or anxiety or improve motivational performance.

16. The method of claim 15, wherein said recombinant microbial cell is a probiotic.

17. The method of claim 16, wherein said probiotic is *E. coli* Nissle 1917.

18. The method of claim 15, wherein said composition is administered orally.

19. The method of claim 15, wherein said composition is administered on alternate days.

20. The method of claim 15, wherein said subject is a mammal.

21. The method of claim 20, wherein said mammal is a human.

22. The method of claim 15, wherein said effective amount comprises from about $10^6$ CFU to about $10^{12}$ CFU of said recombinant microbial cell.

23. The method of claim 22, wherein said effective amount comprises about $10^9$ CFU of said recombinant microbial cell.

24. The method of claim 15 further comprising: co-administering to said subject an effective amount of an aromatic amino acid- or DOPA-decarboxylase inhibitor.

25. The method of claim 24, wherein said DOPA decarboxylase inhibitor is carbidopa or benserazide.

26. The method of claim 15, wherein said composition further comprises L-Tyrosine.

27. The method of claim 15, wherein said recombinant microbial cell comprises a hpaB and hpaC nucleotide sequence as set forth in SEQ ID NO: 1 and 2 or as set forth in SEQ ID NO: 3.

28. The method of claim 27, wherein said hpaB and hpaC nucleotide sequence is operably linked to promoter sequence comprising one or more of SEQ ID NOs: 4-6.

29. The method of claim 15, wherein said depression and/or anxiety is associated with Parkinson's disease.

* * * * *